US009244041B2

(12) United States Patent
Gallippi et al.

(10) Patent No.: US 9,244,041 B2
(45) Date of Patent: Jan. 26, 2016

(54) METHODS, SYSTEMS AND COMPUTER READABLE MEDIA FOR APPLYING MULTI-PUSH ACOUSTIC RADIATION FORCE TO SAMPLES AND MONITORING A RESPONSE TO QUANTIFY MECHANICAL PROPERTIES OF SAMPLES

(75) Inventors: Caterina Gallippi, Cary, NC (US); Mallory Scola, Carrboro, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 809 days.

(21) Appl. No.: 13/597,011

(22) Filed: Aug. 28, 2012

(65) Prior Publication Data
US 2013/0024136 A1 Jan. 24, 2013

Related U.S. Application Data

(63) Continuation-in-part of application No. 12/607,986, filed on Oct. 28, 2009, now Pat. No. 9,043,156.

(60) Provisional application No. 61/109,102, filed on Oct. 28, 2008.

(51) Int. Cl.
*G01N 29/04* (2006.01)
*G01N 29/06* (2006.01)
*G01N 29/34* (2006.01)
*A61B 8/08* (2006.01)

(52) U.S. Cl.
CPC ............. *G01N 29/045* (2013.01); *A61B 8/485* (2013.01); *G01N 29/0654* (2013.01); *G01N 29/343* (2013.01); *A61B 8/08* (2013.01); *G01N 2291/02475* (2013.01); *G01N 2291/02827* (2013.01)

(58) Field of Classification Search
CPC .................. G01N 29/045; G01N 2291/02475
See application file for complete search history.

(56) References Cited

U.S. PATENT DOCUMENTS

| 4,817,015 | A | 3/1989 | Insana et al. |
|---|---|---|---|
| 4,982,339 | A | 1/1991 | Insana et al. |
| 5,265,612 | A | 11/1993 | Sarvazyan et al. |
| 6,277,074 | B1 | 8/2001 | Chaturvedi et al. |
| 6,770,033 | B1 | 8/2004 | Fink et al. |
| 2010/0138163 | A1 | 6/2010 | Gallippi et al. |
| 2010/0191110 | A1* | 7/2010 | Insana .................. A61B 8/0825 600/438 |

OTHER PUBLICATIONS

Yamakoshi et al., "Ultrasonic Imaging of Internal Vibration of Soft Tissue under Forced Vibration," IEEE Trans. Ultrason., Ferroelec., Freq. Contr. 17(2), pp. 45-53 (1990).*
Notice of Allowance for U.S. Appl. No. 12/607,986 (Jan. 22, 2015).

(Continued)

*Primary Examiner* — Phuong Huynh
(74) *Attorney, Agent, or Firm* — Jenkins, Wilson, Taylor & Hunt, P.A.

(57) ABSTRACT

A method for evaluating mechanical properties of a sample includes applying a plurality of pulses of acoustic energy to a sample to apply a mechanical force to the sample and induce a non-steady-state displacement in the sample. The method further includes monitoring a response of the sample caused by the application of the mechanical force. The method further includes determining a quantitative value for a mechanical property of the sample based on the response.

24 Claims, 32 Drawing Sheets

(56) References Cited

OTHER PUBLICATIONS

Applicant-Initiated Interview Summary for U.S. Appl. No. 12/607,986 (Dec. 22, 2014).
Final Office Action for U.S. Appl. No. 12/607,986 (Sep. 17, 2014).
Notice of Allowance and Fee(s) Due for U.S. Appl. No. 12/607,986 (Aug. 16, 2012).
Interview Summary for U.S. Appl. No. 12/607,986 (Aug. 3, 2012).
Restriction and/or Election Requirement for U.S. Appl. No. 12/607,986 (Jul. 2, 2012).
Non-Final Official Action for U.S. Appl. No. 12/607,986 (Feb. 16, 2012).
Restriction and/or Election Requirement for U.S. Appl. No. 12/607,986 (Jan. 9, 2012).
"Exposure criteria for medical diagnostic ultrasound: II. Criteria based on all known mechanisms," National Council on Radiation Protection and Measurements, Bethesda, MD, NCRP Publications, Report No. 140 (Dec. 31, 2002).
Asbach et al. "Assessment of liver viscoelasticity using multifrequency mr elastography," Magnetic resonance in medicine : official journal of the Society of Magnetic Resonance in Medicine / Society of Magnetic Resonance in Medicine 60, pp. 373-379 (2008).
Bacon, "Finite amplitude distortion of the pulsed fields used in diagnostic ultrasound," Ultrasound Med. Biol. 10, pp. 189-195 (1984).
Baldewsing et al., "Local Elasticity Imaging of Vulnerable Atherosclerotic Coronary Plaques," Atherosclerosis, Large Arteries and Cardiovascular Risk, Advance Cardiology, vol. 44, pp. 35-61 (Copyright 2007).
Baldewsing, et al., "Young's Modulus Reconstruction of Vulnerable Atherosclerotic Plaque Components Using Deformable Curvers," Ultrasound Med. Biol., vol. 32, No. 2, pp. 201-210 (2006).
Barton et al., "The rational clinical examination. Does this patient have breast cancer? The screening clinical breast examination: Should it be done? How'?," JAMA: the Journal of the American Medical Association 282, pp. 1270-1280 (1999).
Bassett et al., "Breast sonography," Am. J. Radiol. 156, pp. 449-455 (1991).
Behler et al., "A rigid wall approach to physiological motion rejection in arterial ARFI imaging: Simulation and in vivo demonstration," Proc IEEE Ultrasonics Symp, pp. 359-364 (2007).
Behler et al., "ARFI ultrasound for in vivo hemostasis assessment post cardiac catheterization, part I: preclinical studies," Ultrason Imaging, pp. 153-158 (2009).
Bercoff, et al., "Supersonic Shear Imaging: A New Technique for Soft Tissue Elasticity Mapping," IEEE Transactions on Ultrasonics, Ferroelectrics, and Frequency Control, vol. 51, No. 4, pp. 396-409 (Apr. 2004).
Bercoff et al., "The role of viscosity in the impulse diffraction field of elastic waves induced by the acoustic radiation force," IEEE transactions on ultrasonics, ferroelectrics, and frequency control 51, pp. 1523-1536 (Nov. 2004).
Bilgen, et al., "Elastostatics of a Spherical Inclusion in Homogeneous Biological Media," Physics in Medicine and Biology, vol. 43, No. 1, pp. 1467-1473 (1998).
Booi et al., "Diagnosing cysts with correlation coefficient images from 2-dimensional freehand elastography," J Ultrasound Med. 26, pp. 1201-1207 (2007).
Burns at al., "Ultrasonic Doppler studies of the breast," Ultrasound Med. Biol. 8, pp. 127-143 (1982).
Carey et al., "Complications of femoral artery closure devices," Catheter Cardiovasc Interv. 52(1), pp. 3-7, discussion 8 (2001).
Catheline et al., "Measurement of viscoelastic properties of homogeneous soft solid using transient elastography: An inverse problem approach," J Acoust Soc Am 116, pp. 3734-3741 (2004).
Center for Devices and Radiological Health (CDRH), "510(k) guide for measuring and reporting acoustic output of diagnostic ultrasound medical devices," U S Dept of Health and Human Services 1985, Rev. 1993, 1994 (1985).
Cespedes et al., "Theoretical bounds on strain estimation in elastography," IEEE Transactions on Ultrasonics, Ferroelectrics and Frequency Control 42(5), pp. 969-971 (1995).
Chen et al., "Shearwave dispersion ultrasound vibrometry (sduv) for measuring tissue elasticity and viscosity," IEEE transactions on ultrasonics, ferroelectrics, and frequency control 56, pp. 55-62 (2009).
Chen et al., "Quantifying elasticity and viscosity from measurement of shear wave speed dispersion," J Acoust Soc Am 115, pp. 2781-2785 (2004).
Coussot, et al., "Fractional Derivative Models for Ultrasonic Characterization of Polymer and Breast Tissue Viscoelasticity," IEEE, vol. 45, No. 4, pp. 715-726 (Apr. 2009).
Dangas et al., "Vascular complications after percutaneous coronary interventions following hemostasis with manual compression versus arteriotomy closure devices," J Am Coll Cardiol. 38(3), pp. 638-641 (2001).
Dauerman et al., "Vascular closure devices," Journal of the Americal College of Cardiology 50(17), pp. 1617-1626 (2007).
Doyle et al., "Ambulation 1 hour after diagnostic cardiac catheterization: a prospective study of 1009 procedures," Mayo Clinic Proc. 81(12), pp. 1537-1540 (2006).
Dymling et al., "A new ultrasonic method for fluid property measurements," Ultrasound Med. Biol. 17, pp. 497-500 (1991).
El-Fallah et al., "Ultrasonic measurement of breast tissue motion and the implications for velocity estimation," Ultrasound in Medicine and Biology 23(7), pp. 1047-1057 (1997).
Fatemi et al., "Probing the dynamics of tissue at low frequencies with the radiation force of ultrasound," Phys. Med. Bio. 45(6), pp. 1449-1464 (2000).
Fatemi et al., "Ultrasound-stimulated vibroacoustic spectrography," Science, vol. 280, pp. 82-85 (1998).
Fu, et al., "Non-Invasive Quantitative Reconstruction of Tissue Elasticity Using an Iterative Forward Approach," Physics in Medicine and Biology, vol. 45, No. 6, pp. 1495-1509 (2000).
Fung, "Biomechanics: Mechanical Properties of Living Tissues," 2nd ed. New York: Springer (1993).
Gallippi et al., Complex BSS for acoustic radiation force impulse imaging in the peripheral vasculature, in vivo, Proc IEEE Ultrasonics Symp, v1, pp. 596-601 (2004).
Gao et al., "Imaging of the elastic properties of tissue—a review," Ultrasound in medicine & biology 22, pp. 959-977 (1996).
Germing et al., "Large femoral aneurysm as late complication after vessel closure device application," Clin Res Cardiol 95, pp. 334-337 (2006).
Goodman, "Introduction to Fourier Optics," New York: McGraw-Hill Companies, Inc. (1996).
Greenleaf, et al., "Selected Methods for Imaging Elastic Properties of Biological Tissues," Annual Review of Biomedical Engineering, vol. 5, pp. 57-78 (2003).
Greenleaf, et al., "Ultrasound-Stimulated Vibro-Acoustic imaging in vivo," IEEE Ultrasonics Symposium, pp. 1635-1638 (1998).
Hall, at al., "In Vivo Real-Time Freehand Palpation Imaging," Ultrasound in Medicine and Biology, vol. 29, No. 3, pp. 427-435 (2003).
Hartley, "Characteristics of acoustic streaming created and measured by doppler ultrasound," IEEE Trans. Ultrason., Ferroelec., Freq. Contr. 44(6), pp. 1278-1285 (1997).
Hilton et al., "Realtime breast sonography: Application in 300 consecutive patients," Am. J. Radiol. 165, pp. 479-486 (1986).
Hoffman et al., "Translating mighty mice into neuromuscular therapeutics: Is bigger muscle better?," The American journal of pathology 168, pp. 1775-1778 (Jun. 2006).
Huang et al., "Assessment of blood coagulation under various flow conditions with ultrasound backscattering," IEEE Transactions on Biomedical Engineering 54(12), pp. 2223-2230 (2007).
Huwart et al., "Liver fibrosis: Non-invasive assessment with mr elastography," NMR in biomedicine 19, pp. 173-179 (2006).
Insana et al., "Viscoelastic imaging of breast tumor microenvironment with ultrasound," J Mammary Gland Biol 9, pp. 393-404 (2004).
Insana, et al., "Acoustic Backscattering from Ultrasonically Tissue-like Media," Medical Physics Department, University of Wisconsin, Madison, vol. 9, No. 6, pp. 848-855 (1982).

(56) References Cited

OTHER PUBLICATIONS

Konofagou, et al., "A Focused Ultrasound Method for Simultaneous Diagnostic and Therapeutic Applications—A Simulation Study," Physics in Medicine and Biology, vol. 46, No. 11, pp. 2967-2984 (Oct. 17, 2001).
Koreny et al., "Arterial puncture closure devices compare with standard manual compression after cardiac catheterization: Systematic review and meta-analysis," JAMA 291(3), pp. 350-357 (2004).
Kornegay et al., "The cranial sartorius muscle undergoes true hypertrophy in dogs with golden retriever muscular dystrophy," Neuromuscular disorders: NMD 13, pp. 493-500 (2003).
Krouskop et al., "A pulsed doppler ultrasonic system for making noninvasive measurements of the mechanical properties of soft tissue," J. Rehabil. Res. Dev. 24, pp. 1-8 (1987).
Ledoux et al., "Experimental verification of the correlation behavior of analytic ultrasound radiofrequency signals received from moving structures," Ultrasound in Med. & Bio. 24(9), pp. 1383-1396 (1998).
Lerner et al., "Sonoelasticity images derived from ultrasound signals in mechanically vibrated tissues," Ultrasound Med. Biol. 16, pp. 231-239 (1990).
Levinson, "Ultrasound propagation in anisotropic soft tissues, the application of linear elastic theory," J. Biomech. 20, pp. 251-260 (1987).
Li et al., "Temproal correlation of blood scattering signals in vivo from radiofrequency intravascular ultrasound," Ultrasound in Med. & Bio. 22(5), pp. 583-590 (1996).
Machado et al., "Evaluation of an ultrasonic method applied to the evaluation of blood coagulation time," Physiol. Meas. 18, pp. 129-143 (1997).
Madsen, et al., "Tissue Mimicking Materials for Ultrasound Phantoms," Medical Physics, vol. 5, No. 5, pp. 391-394 (Sep./Oct. 1978).
Mauldin et al., "Monitored steady-state excitation and recovery (msser) radiation force imaging using viscoelastic models," IEEE transactions on ultrasonics, ferroelectrics, and frequency control 55, pp. 1597-1610 (2008).
Maurice, et al., "Non-Invasive High-Frequency Vascular Ultrasound Elastography," Physics in Medicine and Biology, vol. 50, pp. 1611-1628 (Mar. 22, 2005).
McKnight, et al., "MR Elastography of Breast Cancer: Preliminary Results," American Journal of Roentgenology, vol. 178, No. 6, pp. 1411-1417 (Jun. 2002).
McNicholas et al., "Color doppler sonography in the evaluation of breast masses," Am. J. Radiol. 161, pp. 765-771 (1993).
Mendias et al., "Tendons of myostatin-deficient mice are small, brittle, and hypocellular," Proceedings of the National Academy of Sciences of the United States of America 105, pp. 388-393 (2008).
Muller et al., "Quantitative viscoelasticity mapping of human liver using supersonic shear imaging: Preliminary in vivo feasability study," Ultrasound in Medicine and Biology 35, pp. 219-229 (2009).
Muthupillai et al., "Magnetic resonance elastography by direct visualization of propagating acoustic strain waves," Science 269, pp. 1854-1857 (1995).
Nader at al., "Clinical evaluation of SyvekPatch in patients undergoing interventional, EPS and diagnostic cardiac catheterization procedures," J Invasive Cardiol. 14(6), pp. 305-307 (2002).
Najjar et al., "Evaluation of poly-n-acetyl glucosamine as a hemostatic agent in patients undergoing cardiac catheterization: A double-blind, randomized study," J Trauma. 57, pp. S38-S41 (2004).
Nehler et al., "Iatrogenic vascular injuries from percutaneous vascular suturing devices," J Vasc Surg. 33(5), pp. 943-947 (2001).
Nightingale et al, "Observations of Tissue Response to Acoustic Radiation Force: Opportunities for Imaging," Ultrasonic Imaging, vol. 24, No. 3, pp. 100-108 (2002).
Nightingale, et al., "Shear Wave Velocity Estimation Using Acoustic Radiation Force Impulsive Excitation in Liver In Vivo, " in Proc. IEEE Ultrason. Symp., vol. 1, pp. 1156-1160 (2006).
Nightingale, et al., "Shear-Wave Generation Using Acoustic Radiation Force: In vivo and ex vivo Results," Ultrasound in Medicine and Biology, vol. 29, No. 12, pp. 1715-1723 (2003).
Nightingale et al., "On the feasibility of remote palpation using acoustic radiation force," J. Acoust. Soc. Am. 110(1), pp. 625-634 (2001).
Nightingale et al., "A finite element model of remote palpation of breast lesions using radiation force: Factors affecting tissue displacement," Ultrasonic Imaging 22(1), pp. 35-54 (2000).
Nightingale et al., "The use of acoustic streaming in breast lesion diagnosis: a clinical study," Ultrasound Med. Biol. 25(1), pp. 75-87 (1999).
Nightingale et al., "A novel ultrasonic technique for differentiating cysts from solid lesions: Preliminary results in the breast," Ultrasound Med. Biol. 21(6), pp. 745-751 (1995).
Nikolsky et al., "Vascular complications associated with arteriotomy closure devices in patients undergoing percutaneous coronary procedures: a meta-analysis," J Am Coll Cardiol. 44(6), pp. 1200-1209 (2004).
Nyborg, "Solutions of the bio-heat transfer equation," Phys. Med. Biol. 33, pp. 785-792 (1988).
Nyborg, "Acoustic streaming," in Physical Acoustics. vol. IIB, W. Mason, Ed. New York: Academic, ch. 11, pp. 265-331 (1965).
O'Donnell et al., "Internal displacement and strain imaging using ultrasonic speckle tracking," IEEE Trans. Ultrason., Ferroelec., Freq. Contr. 41, pp. 314-325 (1994).
Oliphant, et al., "Complex-Valued Stiffness Reconstruction From Magnetic Resonance Elastography by Algebraic Inversion of the Differential Equation," Magnetic Resonance in Medicine, vol. 45, pp. 299-310 (2001).
Ophir, et al., "Elastography: Ultrasonic Estimation and Imaging of the Elastic Properties of Tissue," in Proc. Inst. Mech. Eng. [H], vol. 213, pp. 203-233 (1999).
Ophir et al., "Elastography: A quantitative method for imaging the elasticity of biological tissues," Ultrasonic Imaging 13, pp. 111-134 (1991).
Orescanin, et al., "Material Properties From Acoustic Radiation Force Step Response," Acoustical Society of America, vol. 125, No. 5, pp. 2928-2936 (May 2009).
Palmeri, et al., "Dynamic Mechanical Response of Elastic Spherical Inclusions to Impulsive Acoustic Radiation Force Excitation," IEEE Trans. Ultrason., Ferroelect., Freq. Contr., vol. 53, No. 11, pp. 2065-2079 (2006).
Palmeri, et al., "Ultrasonic Tracking of Acoustic Radiation Force-Induced Displacements in Homogeneous Media," IEEE Transactions on Ultrasonics, Ferroelectrics, and Frequency Control, vol. 53, No. 7, pp. 1300-1313 (Jul. 2006).
Palmeri, et al., "A Finite-Element Method Model of Soft Tissue Response to Impulsive Acoustic Radiation Force," IEEE Transactions on Ultrasonics, Ferroelectrics, and Frequency Control, vol. 52, No. 10, pp. 1699-1712 (Oct. 2005).
Palmeri et al., "On the thermal effects associated with radiation force imaging in soft tissue," Ultrasound in Medicine and Biology 26, pp. 551-565 (2004).
Parker et al., "Tissue response to mechanical vibrations for sonoelasticity imaging," Ultrasound Med. Biol. 16, pp. 241-246 (1990).
Pennes, "Analysis of tissue and arterial blood temperatures in the resting human forearm," J. Appl. Physiol. 1, pp. 93-122 (1948).
Plewes, et al., "Visualization and Quantification of Breast Cancer Biomechanical Properties With Magnetic Resonance Elastography," Physics in Medicine and Biology, vol. 45, No. 1, pp. 1591-1610 (2000).
Qiu, et al., "Ultrasonic Viscoelasticity Imaging of Nonpalpable Breast Tumors: Preliminary Results," Academic Radiology, vol. 15, No. 12, pp. 1526-1533 (Dec. 2008).
Ruygrok et al., "Initial experience with a new femoral artery closure device following percutaneous coronary intervention with glycoprotein 11b/IIIa inhibition," Catheterization and Cardiovascular Interventions 66, pp. 185- 191 (2005).
Salameh et al., "Early detection of steatohepatitis in fatty rat liver by using mr elastography," Radiology 253, pp. 90-97 (Oct. 2009).
Sarvazyan, et al., "Shear Wave Elasticity Imaging: A New Ultrasonic Technology of Medical Diagnostics," Ultrasound med. Biol., vol. 24, No. 9, pp. 1419-1435 (1998).

(56) References Cited

OTHER PUBLICATIONS

Scheinert et al., "The safety and efficacy of an extracellular water-soluble sealant for vascular closure: initial clinical results for Mynx™," Catheterization and Cardiovascular Interventions 70, pp. 627-633 (2007).
Shi et al., "Color doppler imaging of acoustic streaming in blood and clot," IEEE Ultrason. Symp., pp. 1315-1318 (1999).
Sinkus, et al., "High-Resolution Tensor MR Elastography for Breast Tumor Detection," Physics in Medicine and Biology, vol. 45, No. 6, pp. 1649-1664 (2000).
Sohail et al., "Infectious complications of percutaneous vascular closure devices," Mayo Clin Proc. 80(8), pp. 1011-1015 (2005).
Sridhar, et al., "Ultrasonic Measurements of Breast Viscoelasiticty," American Association of Physics and Medicine, vol. 34, No. 12, pp. 4757-4767 (Nov. 20, 2007).
Sridhar, et al., "Viscoelasticity Imaging Using Ultrasound: Parameters and Error Analysis," Physics in Medicine and Biology, vol. 52, pp. 2425-2443 (Apr. 10, 2007).
Starritt et al., "Forces acting in the direction of propagation in pulsed ultrasound fields," Phys. Med. Biol. 36, pp. 1465-1474 (1991).
Starritt et al., "An experimental investigation of streaming in pulsed diagnostic ultrasound beams," Ultrasound Med. Biol. 15, pp. 363-373 (1989).
Steele, et al., "Three-Dimensional Static Displacement, Stimulated Echo NMR Elasticity Imaging," Physics in Medicine and Biology, vol. 45, No. 1, pp. 1633-1648 (2000).
Sugimoto et al., "Tissue hardness measurement using the radiation force of focused ultrasound," In: Proceedings of the 1990 Ultrasonics Symposium, pp. 1377-1380 (1990).
Tanter et al., "Quantitative assessment of breast lesion viscoelasticity: Initial clinical results using supersonic shear imaging," Ultrasound in medicine & biology 34, pp. 1373-1386 (2008).
Taylor, et al., "Three-Dimensional Sonoelastography: Principles and Practices," Physics in Medicine and Biology, vol. 45, pp. 1477-1494 (2000).
Torr, "The acoustic radiation force," Am. J. Phys. 52, pp. 402-408 (1984).
Trahey, et al., "Acoustic Radiation Force Impulse Imaging of the Mechanical Properties of Arteries: In vivo and ex vivo Results," Ultrasound in Medicine and Biology, vol. 30, No. 9, pp. 1163-1171 (2004).
Trahey et al., "Angle independent ultrasonic blood flow detection by frame-to-frame correlation of B-mode images," Ultrasonics, vol. 26, pp. 271-276 (1987).
Van Houten, et al., "Elasticity Reconstruction From Experimental MR Displacement Data: Initial Experience With an Overlapping Subzone Finite Element Inversion Process," Medical Physics, vol. 27, No. 1, pp. 101-107 (Jan. 2000).
Vappou et al., "Quantitative viscoelastic parameters measured by harmonic motion imaging," Phys Med Biol 54, pp. 3579-3594 (2009).
Varghese, et al., "Elastographic Imaging of Thermal Lesions in the Liver in vivo Following Radiofrequency Ablation: Preliminary Results," Ultrasound in Medicine and Biology, vol. 28, pp. 1467-1473 (2002).
Viola et al., "Sonrheometry: A noncontact method for the dynamic assessment of thrombosis," Annals of Biomedical Engineering, 32(5), pp. 696-705 (2004).
Viola, et al, "Radiation Force Imaging of Viscoelastic Properties With Reduced Artifcats," IEEE Trans. Ultrason., ferroelect., Freq. contr., vol. 50, No. 6, pp. 736-742 (2003).
Voleisis et al., "Ultrasonic method for the whole blood coagulation analysis," Ultrasonics 40, pp. 101-107 (2002).
Wagner et al., "A phase i/iitrial of myo-029 in adult subjects with muscular dystrophy," Annals of neurology 63, pp. 561-571 (2008).

Walker, et al., "A Method of Imaging Viscoelastic Parameters With Acoustic Radiation Force," Phys. Med, Biol., vol. 45, No. 6, pp. 1437-1447 (2000).
Walker et al., "A fundamental limit on delay estimation using partially correlated speckle signals," IEEE Trans. Ultrason., Ferroelec., Freq. Contr. 42(2), pp. 301-308 (1995).
Wu et al., "Acoustic streaming generated by a focused Gaussian beam and finite amplitude tonebursts," Ultrasound Med. Biol. 19, pp. 167-176 (1993).
Yamakoshi et al., "Ultrasonic imaging of internal vibration of soft tissue under forced vibration," IEEE Trans. Ultrason., Ferroelec., Freq. Contr. 17(2), pp. 45-53 (1990).
Zauhar et al., "Studies of acoustic streaming in biological fluids with an ultrasound doppler technique," British Journal of Radiology 71, pp. 297-302 (1998).
Zderic et al., "Intra-operative hemostasis of punctured femoral artery using HIFU: a survival study," 4th International Symp on Therapeutic Ultrasound, pp. 71-73 (2005).
Zhu et al., "Strain imaging with a deformable mesh," Ultrasonic Imaging 21(2), pp. 127-146 (1999).
Non-Final Office Action for U.S. Appl. No. 12/607,986 (May 5, 2014).
Dalecki, "Mechanisms of Interaction of Ultrasound and Lithotripter Fields with Cardiac and Neural Tissues," Ph.D. thesis, University of Rochester (1993).
Deffieux et al., "Shear wave spectroscopy for in vivo quantification of human soft tissues visco-elasticity," IEEE Trans Med Imaging 28, pp. 313-322 (2009).
Duck et al., "The output of pulse-echo ultrasound equipment: A survey of powers, pressures and intensities," Br. J. Radiol. 58, pp. 989-1001 (1985).
Garra et al., "Elastography of breast lesions: Initial clinical results," Radiology 202, pp. 79-86 (1997).
Khaleghian, "Breast cysts: Pitfalls in sonographic diagnosis," Australas. Radio. 37, pp. 192-194 (1993).
Mitri et al., "Shear wave dispersion ultrasonic vibrometry for measuring prostate shear stiffness and viscosity: An in vitro pilot study," IEEE transactions on bio-medical engineering 58, pp. 235-242 (2011).
NCRP, "Report No. 113: Exposure Criteria for Medical Diagnostic Ultrasound: I. Criteria Based on Thermal Mechanisms," NCRP Publications, Bethesda, MD 20814: National Council on Radiation Protection and Measurements (1992).
NCRP, "Report No. 74: Biological Effects of Ultrasound: Mechanisms and Clinical Implications," NCRP Publications, Bethesda, MD 20814: National Council on Radiation Protection and Measurements (1983).
Palmer et al., "Effectiveness and safety of manual hemostasis facilitated by the SyvekPatch with one hour of bedrest after coronary angiography using six-French catheters," Am J Cardiol. 93(1), pp. 96-97 (2004).
Pan, et al., "Ultrasound low-velocity flow estimation using cross-correlation and decorrelation: a thread phantom study," Medical Engineering and Physics. 19, pp. 602-614 (2007).
Park, et al., "Strain Imaging Using Conventional and Ultrafast Ultrasound Imaging: Numerical Analysis," IEEE Transactions on Ultrasonics, Ferroelectrics, and Frequency Control, vol. 54, No. 5, pp. 987-995 (May 2007).
Samani, et al., "An Inverse Problem Solution for Measuring the Elastic Modulus of Intact ex vivo Breast Tissue Tumours," Physics in Medicine and Biology, vol. 52, No. 5, pp. 1247-1260 (Feb. 1, 2007).
Sarvazyan et al., "Biophysical bases of elasticity imaging," Acoustical Imaging 21, pp. 223-240 (1995).
Stavros et al., "The ultrasound of breast pathology," In: Percutaneous breast biopsy. New York: Raven Press, pp. 111-115 (1993).
Wille et al., "Acute leg ischemia: the dark side of a percutaneous femoral artery closure device," Ann Vasc Surg. 20(2), pp. 278-281 (2006).

\* cited by examiner

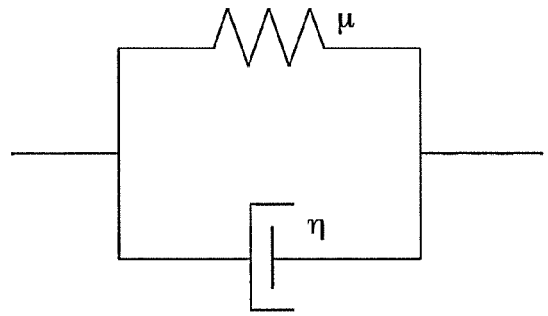
FIG. 1A
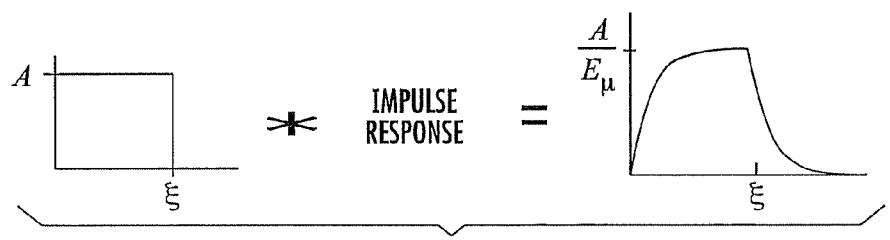
FIG. 1B
FIG. 1C

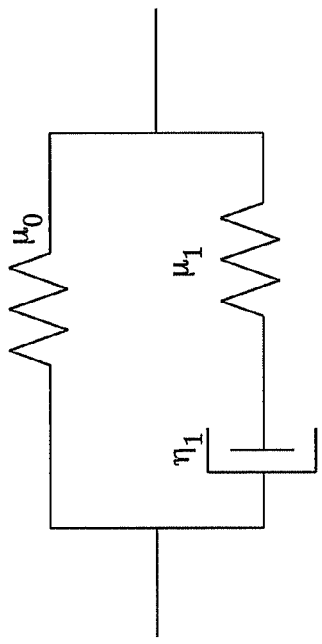
FIG. 2A
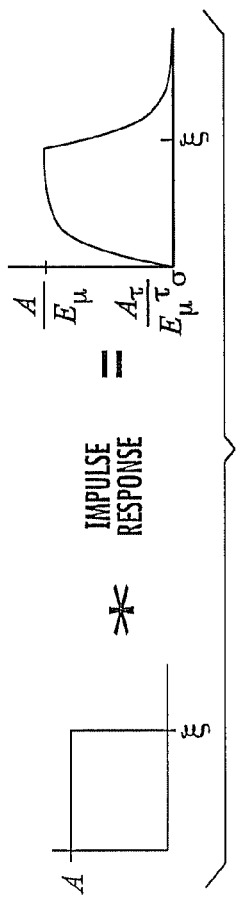
FIG. 2B
FIG. 2C

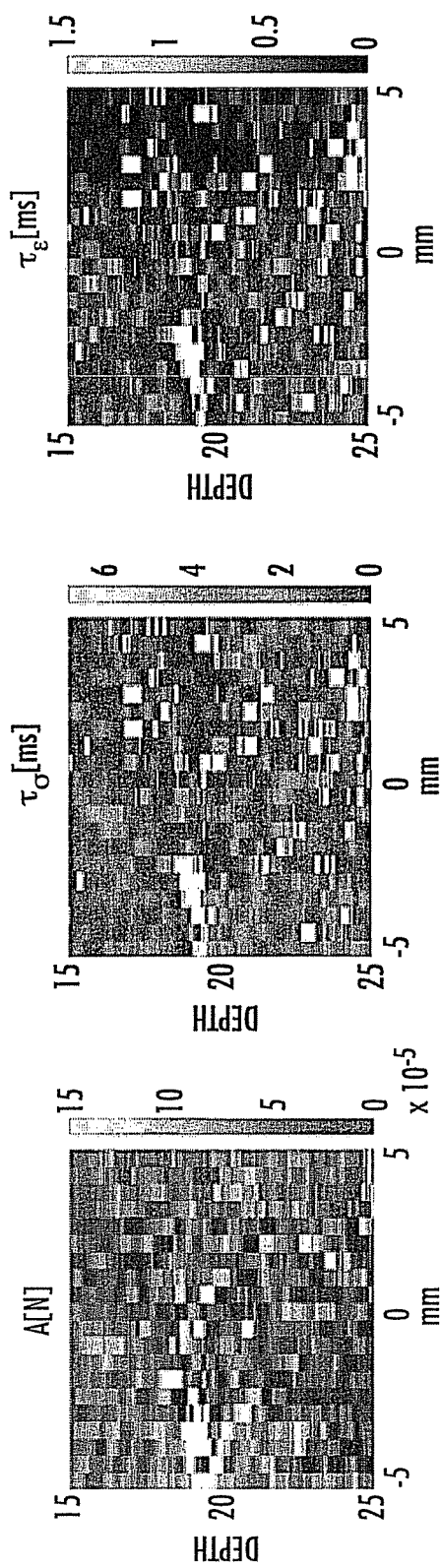

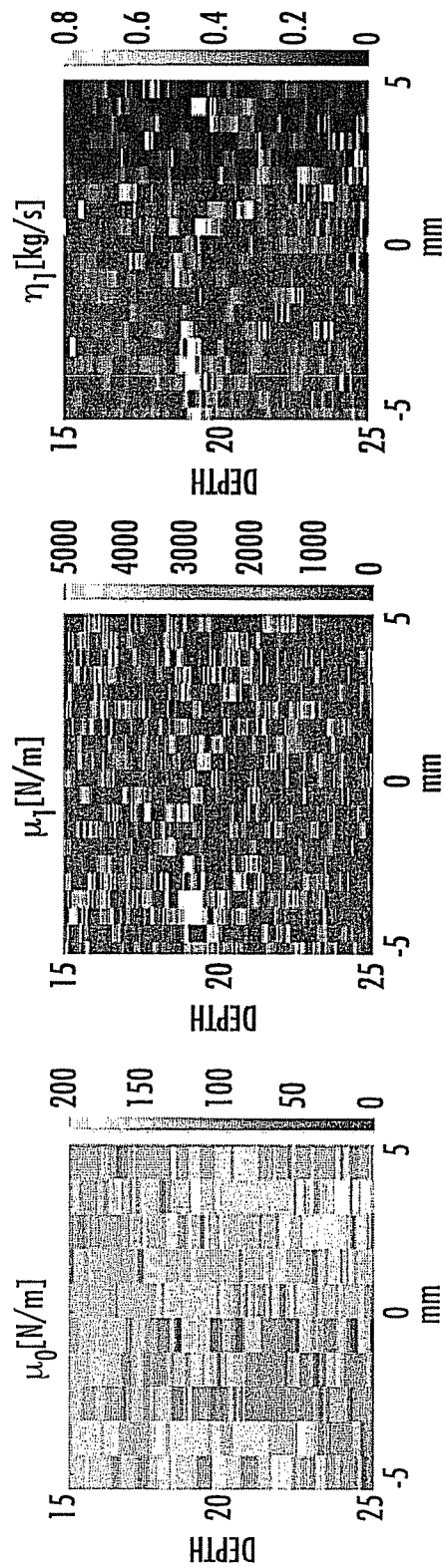

METHODS, SYSTEMS AND COMPUTER READABLE MEDIA FOR APPLYING MULTI-PUSH ACOUSTIC RADIATION FORCE TO SAMPLES AND MONITORING A RESPONSE TO QUANTIFY MECHANICAL PROPERTIES OF SAMPLES

PRIORITY CLAIM

This application is a continuation-in-part of U.S. patent application Ser. No. 12/607,986, filed Oct. 28, 2009, which claims the benefit of U.S. Provisional Patent Application Ser. No. 61/109,102, filed Oct. 28, 2008, the disclosures of which are incorporated herein by reference in their entireties.

GOVERNMENT INTEREST

This invention was made with government support under Grant Nos. HL092944 and NS074057 awarded by the National Institutes of Health. The government has certain rights in the invention.

TECHNICAL FIELD

The subject matter disclosed herein relates generally to methods for determining mechanical properties of samples. More particularly, the subject matter described herein relates to methods, systems and computer readable media for applying multi-push acoustic radiation force to samples and monitoring a response to quantify mechanical properties of samples.

BACKGROUND

Ultrasonic techniques for the mechanical characterization of viscoelastic materials such as soft tissue have grown in interest due to their clinical relevance to monitoring the progression of various diseases [1]. These techniques include ultrasound elastography monitoring of strain in response to both extrinsic and intrinsic forces. Several researchers have developed elastography methods to render images of local strains by applying a relatively uniform, external compression to tissue and tracking subsequent tissue displacements [2]-[16]. The elastic modulus of tissue can be estimated using these methods with minimal complexity, providing an intrinsic measurement of the tissue's material properties. However, because direct compression of tissue is required, elastography can be challenging when attempting to access tissue superficial to boundaries such as organ or vascular layers. Elastographic methods that monitor tissue response to intrinsic forces, such as cardiac pulsation have also been developed but with small strains associated with poor contrast in parametric images [17]-[19].

One possible alternative method that has been explored involves tracking local strains in tissue through acoustic radiation force imaging. Rather than relying on external compression, acoustic radiation force methods use high-intensity ultrasound pulses to transfer momentum to tissue [20]-[31]. By direct application of focused radiation force at the point of interest, these methods allow for measurement of tissue responses superficial to boundary layers. Several techniques involve monitoring the dynamic response of tissue to impulsive radiation force. In acoustic radiation force impulse (ARFI) imaging, tissue displacements are generally tracked axially after the transmission of a temporally short (e.g., <1 ms), focused acoustic radiation force excitation. Resulting tissue displacement data are typically illustrated through a set of parametric images that include peak displacement and time to recovery. Although these parameters have been shown to be inversely related to the Young's modulus in homogeneous elastic media [30], only the relative stiffness or compliance of tissue can be assessed from ARFI imaging because the magnitude of radiation force is generally unknown. That being said, the generation of impulsive tissue excitation also results in the initiation of shear wave propagation traveling perpendicular to the applied force. Shear wave elasticity imaging (SWEI) produces force-independent images of the reconstructed shear moduli of tissue by monitoring shear wave speed [28], [32].

Other applications of acoustic radiation force imaging include monitoring of the resonant response to excitation as in vibro-acoustography [20] or harmonic motion imaging [24]. In kinetic acoustic vitroretinal examination (KAVE) as developed by Walker et al. [22], [23], multiple acoustic pulses per lateral location are generated with a single element piston transducer to observe the steady-state response of tissue to acoustic radiation force. Assuming that the forcing function is a temporal step function and tissue can be described discretely as a Voigt model, images can be generated of force-free parameters depicting the time constant, damping ratio, and natural frequency of the examined homogeneous tissue mimicking material.

Although these techniques can be useful in identifying certain characteristics of the tissue, most of the results obtained are qualitative rather than quantitative. For example, using existing ultrasound measurement techniques, elasticity and viscosity of a sample can be determined relative to that of other samples, and not in absolute numbers. Other existing viscoelastic measurement techniques involve applying acoustic radiation force to tissue that pushes tissue to a steady state of displacement or that allows full recovery of the tissue between successive applications of acoustic radiation force. While such mechanisms may be useful, pushing to steady state and/or allowing full recovery between successive pushes can increase the time required to evaluate samples. Accordingly, in light of these difficulties with associated with conventional acoustic radiation force measurement techniques, there exists a need for improved methods, systems, and computer readable media for methods, systems and computer readable media for applying multi-push acoustic radiation force to samples and monitoring a response to quantify mechanical properties of samples.

SUMMARY

The subject matter described herein includes methods, systems, and computer readable media for methods, systems and computer readable media for applying multi-push acoustic radiation force to samples and monitoring a response to quantify mechanical properties of samples. According to one aspect of the subject matter described herein, a method for evaluating mechanical properties of a sample is provided. The method includes applying a plurality of pulses of acoustic energy to a sample to apply a mechanical force to the sample and to induce non-steady-state displacement in the sample. The method further includes monitoring a response of the sample caused by the application of the mechanical force. The method further includes determining a quantitative value for a mechanical property of the sample based on the response. In at least some of the examples described above, acoustic radiation force may be applied to tissues so that the tissue is displaced to less than the steady state displacement and recovery response may be measured following the displacement without allowing full recovery before the next non-steady state displacement of the tissue.

According to another aspect of the subject matter described herein, a system for determining a quantitative value for a mechanical property of a sample is provided. The system includes at least one acoustic transducer for applying a plurality of pulses of acoustic energy to a sample to apply a mechanical force to the sample and induce a non-steady-state displacement in the sample and for monitoring a response of the sample caused by the application of the mechanical force. The system further includes a mechanical properties estimator for determining a quantitative value for a mechanical property of the sample based on the response.

The subject matter described herein can be implemented using a non-transitory computer readable medium having stored thereon executable instructions that when executed by the processor of a computer control the computer to perform steps. Exemplary computer readable media suitable for implementing the subject matter described herein may include chip memory devices, disk memory devices, programmable logic devices, and application specific integrated circuits. In addition, a computer readable medium that implements the subject matter described herein may be located on a single device or computing platform or may be distributed across multiple devices or computing platforms.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which:

FIG. 1A is a schematic of a Voigt model for use by the systems and methods according to embodiments of the presently disclosed subject matter;

FIG. 1B is a time-domain linear systems block diagram associated with the Voigt model shown in FIG. 1A;

FIG. 1C is a graphical illustration of a forcing function input and resulting viscoelastic response associated with the Voigt model shown in FIG. 1A;

FIG. 2A is a schematic of a standard linear viscoelasticity model for use by the systems and methods according to embodiments of the presently disclosed subject matter;

FIG. 2B is a time-domain linear systems block diagram associated with the standard linear model shown in FIG. 2A;

FIG. 2C is a graphical illustration of a forcing function input and resulting viscoelastic response associated with the standard linear model shown in FIG. 2A;

FIGS. 11A through 11I illustrate parametric images of excised pig muscle from B-mode, conventional ARFI, SWEI, and a combined SWEI and MSSER approach;

DETAILED DESCRIPTION

Overview of Steady State Excitation Techniques

Figure 3A:
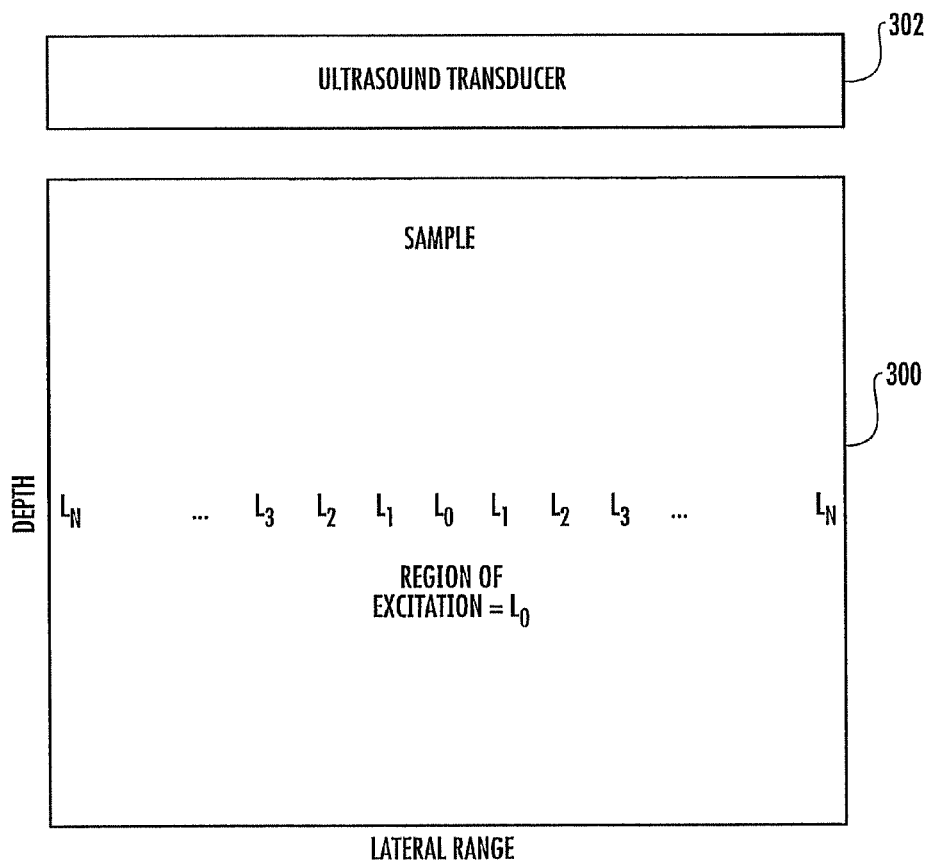
FIG. 3A is a schematic diagram of an exemplary experimental setup for monitored steady-state excitation and recovery (MSSER) and SWEI imaging according to an embodiment of the presently disclosed subject matter.

One aspect of the subject matter described herein includes methods, systems, and computer readable media for monitored application of mechanical force to samples using acoustic energy and mechanical parameter value extraction using mechanical response models. In one exemplary implementation a combined approach to radiation force imaging can be used. The combined approach includes measuring the tissue response to steady state acoustic force excitation and the tissue response after cessation of the excitation. The subject matter described herein includes modeling the viscoelastic tissue response to radiation force excitation discretely through the application of the Voigt and standard linear models and determining model parameter values using measured tissue response values. In addition, although the subject matter disclosed herein is disclosed primarily with a focus on viscoelastic materials, it is to be understood that the principles described can be applied to determine the mechanical parameter values for any material that can be accurately modeled using a mechanical model that models the mechanical response of the material when excited by a forcing function and whose displacement settles to an equilibrium value under application of the forcing function.

The imaging technique described herein is a noninvasive radiation force based method using a commercially available ultrasound scanner and linear array transducer to monitor steady-state tissue response during extended force application and also the transient or recovery response following cessation of force application. In this way, the present technique mimics a materials creep test by applying a constant load while observing the material "creep" or slow movement to steady state displacement but then also observing the transient response after force termination. This combined imaging technique is referred to herein as monitored steady-state excitation and recovery (MSSER) imaging. The imaging technique is described below first to obtain an estimate of Young's modulus to confirm that MSSER imaging approximates viscoelastic tissue response to uniaxial mechanical compression. It will then be demonstrated that the radiation force imaging methods described herein, in conjunction with SWEI, discern all parameters of the viscoelastic model in quantitative terms or numeric values. The numeric values determined for the parameters in the experiments described herein are not in terms of the applied 1 radiation force magnitude. Experimental data are collected in homogeneous gelatin phantoms of different stiffness and in excised pig muscle.

Viscoelastic Models

The mechanical properties of viscoelastic materials, particularly soft tissue, have been widely studied in the field of biomechanics with several viscoelastic models describing material response to external mechanical stimuli [33]. Two such models that predict a similar mechanical response to a constant stress application are the Voigt and standard linear models. Either model can serve as a viable predictor of response of a material sample to acoustic radiation force excitation. For instance, referring to FIG. 1 (A, a schematic of the mechanical model for the Voigt model is provided, the model consisting of a linear spring with spring constant $\mu$ in parallel with a dashpot with coefficient of viscosity, $\eta$. The linear spring produces instantaneous displacement proportional to the applied force while the dashpot produces velocity proportional to the applied force. Therefore, if an applied force F acts on the linear spring to produce an instantaneous displacement x(0) then, $F=\mu x(0)$. Similarly, if the same applied force acts on a dashpot, the result will be a velocity through time t so that $F=\eta(dx(t)/dt)$. The differential equation describing the Voigt model is as follows:

$$F(t) = E_\mu x(t) + E_\mu \tau_\sigma \frac{dx(t)}{dt} \tag{1}$$

where F(t) [N] is the applied force, x(t) [m] is displacement, $E_\mu$ [N/m] is the relaxed elastic modulus, and $\tau_\sigma$ [s] is the relaxation time constant for constant stress. The constants from Equation (1) can be described in terms of the spring and damper constants in FIG. 1A:

$$E_\mu = \mu, \tag{2}$$

$$\tau_\sigma = \frac{\eta}{\mu}$$

In FIG. 1B, a time-domain linear systems block diagram of the Voigt model is illustrated, where force F(t) is the input, the system impulse response is listed inside the box, and displacement through time x(t) is the output. In addition, a graphical representation of the input forcing function and subsequent viscoelastic response is illustrated in FIG. 1C in the instance where $\xi$ is sufficiently large so that the response approaches the steady-state value $A/E_\mu$. If the forcing function for this model is described as a temporal unit step function U(t) of force magnitude A [N] from time zero to $\xi$ the Voigt output given the mechanical properties $E_\mu$ and $\tau_\sigma$ of the sample predicts an exponential behavior with time constant $\tau_\sigma$ and a steady-state displacement in creep loading, $x_{ss}$ achieving the following relationship:

$$x(t) = \frac{A}{E_\mu}\left(1 - e^{-\frac{t}{\tau_\sigma}}\right); \tag{3}$$

for $0 < t < \xi$ $$x_{ss} = \frac{A}{E_\mu} \tag{4}$$

In FIG. 2A, a schematic of the linear spring, dashpot system governing the standard linear model is illustrated. The standard linear model is also referred to as the Kelvin model. In this model, there is an additional linear spring in series with the dashpot, which accounts for an immediate initial deflection in displacement in response to force excitation. The differential equation describing the Standard Linear model is as follows:

$$F(t) = \tau_\varepsilon \frac{F(t)}{dt} = E_\mu \left( x(t) + \tau_\sigma \frac{x(t)}{dt} \right) \quad (5)$$

where $\tau_\varepsilon$ [s] is the relaxation time constant for constant strain. The material constants from Equation (5) can be defined in terms of the spring, damper system from FIG. 2A:

$$E_\mu = \mu_0, \quad (6)$$
$$\tau_\sigma = \frac{\eta_1}{\mu_0}\left(1 + \frac{\mu_0}{\mu_1}\right),$$
$$\tau_\varepsilon = \frac{\eta_1}{\mu_1}$$

Considering a temporal unit step forcing function input, the time-domain linear-systems block diagram for the standard linear model is illustrated in FIG. 2B along with a graphical representation of the input and viscoelastic response in FIG. 2C:

$$x(t) = \frac{A}{E_\mu} - \frac{A(\tau_\sigma - \tau_\varepsilon)}{E_\mu \tau_\sigma} e^{-\frac{t}{\tau_\sigma}}; \quad (7)$$
$$\text{for } 0 < t < \xi$$

The illustration in FIG. 2C depicts the instance where $\xi$ is sufficiently large so that the response approaches the steady-state value $A/E_\mu$. It is noted that both the standard linear and Voigt models share the same relaxation time constant for constant stress $\tau_\sigma$ and the same steady-state response as described in Equation (4). There are two primary differences between the impulse responses and displacements predicted by the Voigt and standard linear models. First, the standard linear model incorporates an additional relaxation time constant for constant strain. $\tau_\varepsilon$, into the model, which is not required by the Voigt model. Second, while the Voigt model predicts zero instantaneous displacement, the standard linear model predicts an instantaneous deflection with force application, and the amount of deflection is determined by the mechanical properties of the sample:

$$x(0) = \frac{A\tau_\varepsilon}{E_\mu \tau_\sigma} \quad (8)$$

By developing an acoustic radiation force technique to mimic the constant temporal unit step stress inputs shown in FIG. 1 or FIG. 2, and assuming that the sample of interest is composed of a viscoelastic material, the displacement solutions to either system can be modeled and material parameters of interest can be extracted from the model. As will be described in more detail below, the applied radiation force magnitude, A, can be determined from the elastic modulus E and MSSER data. The mechanical properties of interest can then be determined in quantitative terms (i.e., numeric values). A is related to the magnitude of radiation force per unit volume (the body force magnitude), $|\vec{F}|$ [N/m$^3$], by the following relationship:

$$A = |\vec{F}| \times L_{Lat} \times L_{Elev} \times L_{Axial} \quad (9)$$

where $L_{Lat}$ [m], $L_{Elev}$ [m], and $L_{Axial}$ [m] are the lateral, elevational, and axial spans over which the acoustic radiation body force acts. $|\vec{F}|$ has been described [31], [34] as:

$$|\vec{F}| = \frac{2\alpha I}{c} \quad (10)$$

where c [m/s] is the speed of sound, $\alpha$ [Np/m] is the absorption coefficient of the media, and I [W/m$^2$] is the temporal average intensity at a given spatial location. Variations in $\alpha$ and c from sample to sample and even within a single sample structure yield uncertainty in delivered body force magnitude and, therefore, in A. One approach to approximating A is to measure $\alpha$, c, and I directly to estimate $|\vec{F}|$ by using Equation (10). However, this approach is generally not clinically relevant. An alternative approach is to measure the elastic modulus (e.g., Young's modulus) of the material sample E [N/m$^2$] by SWEI to estimate A using Equations (9) and (14).

First, regarding the approach that involves approximating E from an estimated body force magnitude, $|\vec{F}|$, the elastic modulus E [N/m$^2$] of a viscoelastic material sample at equilibrium deformation can be determined by the slope of its stress versus strain relationship:

$$E = \frac{\Delta\sigma}{\Delta\varepsilon} \quad (11)$$

where $\sigma$ [N/m$^2$] is the applied stress and E is a unitless measure of the resulting strain. To estimate the elastic modulus in Equation (11), the magnitude of radiation force $|\vec{F}|$ [N/m$^3$] is adapted to units of stress [N/m$^2$] while steady state displacement $\chi_{ss}$ [m] is adapted to unitless strain. The estimated stress $\tilde{\sigma}$ [N/m$^2$] can be approximated as the magnitude of the radiation body force multiplied by the axial length $L_{Axial}$ [m] over which the body force acts. Estimated stress represents the applied force per area spanning the lateral and elevational dimensions:

$$\tilde{\sigma} = |\vec{F}| \times L_{Axial} \quad (12)$$

Similarly, the estimated strain $\tilde{\varepsilon}$ can be defined as the steady state displacement normalized by the original axial length $L_0$ [m] of material over which the body force acts:

$$\tilde{\varepsilon} = \frac{\tilde{x}_{ss}}{L_0} \quad (13)$$

By substituting Equations (12) and (13) into Equation (11) and introducing a correction factor C, an estimated elastic modulus $\tilde{E}$ [N/m$^2$] can be calculated:

$$\tilde{E} = \frac{\Delta\tilde{\sigma}}{\Delta\tilde{\varepsilon}} \times C = \frac{\Delta(|\vec{F}|L_{Axial}L_0)}{\Delta x_{ss}} \times C \quad (14)$$

where $\Delta\tilde{\sigma}/\Delta\tilde{\varepsilon}$ is the slope of estimated stress versus estimated strain. The correction factor C is predominantly implemented because of system-dependent factors that lead to underestimation of steady-state displacement as well as error in estimation of $L_{Axial}$ and $L_0$. These factors contributing to C are addressed more specifically hereinbelow. Note that the correction factor can be globally determined, and its established value can be used consistently across all samples.

Second, regarding the case of the elastic modulus being determined by SWEI, Equation (14) can be used to measure an estimated body force magnitude, $|\vec{F}|$. This estimated body force magnitude can then be related back to A in discrete viscoelastic models through Equation (9). That is, the applied radiation force magnitude for a tissue sample can be calculated by multiplying the estimated body force by the dimensions over which the force is applied using Equation (9). Once the value for A is determined in this way, values for additional mechanical properties can be determined based on the relationships between those mechanical properties and the applied force magnitude (See, e.g., Equations (3) through (8) above). As a result, the mechanical properties of the tissue sample can be described in absolute rather than comparative terms.

Methods

A. Radiation Force Imaging

Figure 3B:
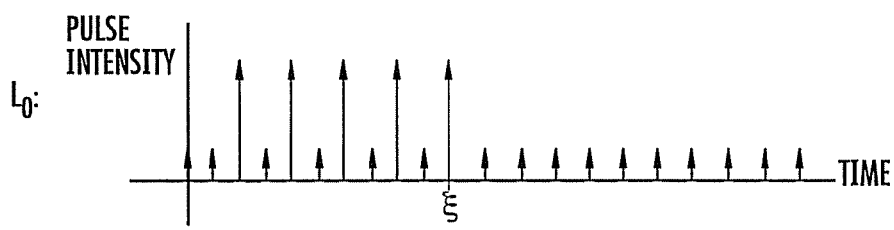
FIG. 3B is graph of exemplary excitation and reference pulse sequences utilized in the region of acoustic excitation for MSSER imaging according to an embodiment of the presently disclosed subject matter.
Figure 3C:
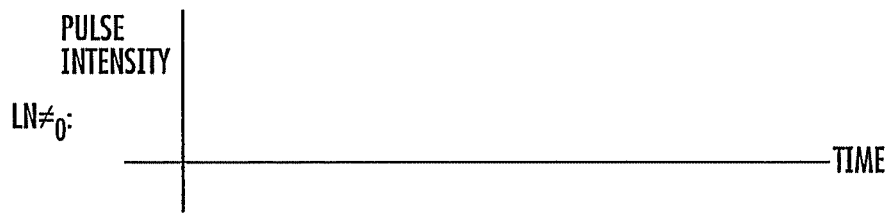
FIG. 3C is a graph illustrating the absence of excitation and reference pulses outside the region of acoustic excitation for MSSER imaging according to an embodiment of the present disclosed subject matter.

In the experiments described herein, a Siemens SONOLINE Antares ultrasound scanner produced by Siemens Medical Solutions USA, Inc., Ultrasound Division, with a VF7-3 transducer was used. Imaging was performed at an axial focal distance of 20 mm with an F/1.5 focal configuration. Similar to conventional ARFI imaging, MSSER used two types of beams that included higher intensity 6-, 8-, 10-, or 12-cycle pushing beams and conventional two-cycle B-mode tracking beams. Two reference-tracking beams were fired first to establish initial position. The reference tracking beams were then followed by a sequence of 30 pushing beams interspersed with single-tracking beams, which served to monitor displacement during force application. This single push-single track sequence was implemented to mimic a temporal unit step forcing function while still allowing for displacement tracking throughout the pushing period. Finally, 60 additional tracking beams followed force cessation monitored displacement relaxation. FIG. 3A is a schematic diagram illustrating a sample and lateral ranges over which pushing and tracking beams were applied. In FIG. 3A, sample 300 represents a sectional slice of a sample being imaged by an ultrasound transducer 302. The region of acoustic excitation by ultrasound transducer 302 is illustrated by location $L_0$. The regions $L_{-1}$-$L_{-N}$ and $L_{-1}$-$L_{-N}$ are locations lateral to the region of acoustic excitation. As illustrated in FIGS. 3B and 3C, MSSER imaging involves excitation with pushing pulses (represented by the taller arrows) and reference pulses (represented by the shorter arrows) in the region of acoustic excitation $L_0$ and no reference pulses outside the region of acoustic excitation. It should be noted that the region of acoustic excitation $L_0$, although shown in the center of sample 300 in FIG. 3A, can be at any location in the sample.

Tracking and pushing beams were administered at center frequencies of 6.15 MHz and 4.21 MHz, respectively. The pulse repetition frequency (PRF) for the technique was 6.65 kHz for pushing pulses and 7.39 kHz for tracking pulses. The total duration of the pushing sequence in this configuration, including intermittent tracking beams, was 8.6 ms, and the total data acquisition time in each lateral position was 17.0 ms. Radiation force-induced displacement was monitored in 20 lateral locations spaced 0.53 mm apart and spanning a total lateral field of view (FOV) of 10.6 mm. The image acquisition time for the entire field of view under these operating parameters was 0.339 s.

Four different pushing beams were used for MSSER imaging during separate image acquisitions, including 6-cycle (1.4 μs), 8-cycle (1.9 μs), 10-cycle (2.4 μs), and 12-cycle (2.9 μs) pulses. By increasing the pulse length of pushing beams, the effective magnitude of the mimicked temporal unit step forcing function was increased. In this way, MSSER imaging allowed control of the magnitude of force application A [N] through pushing pulses of variable duration. Similarly, it is possible to vary the duration of force application by varying the total number of pushing pulses. In the experiments described herein, 30 pushing pulses per lateral location were consistently used. Axial displacements were calculated using the acquired tracking lines and conventional one-dimensional cross correlation.

Figure 3D:
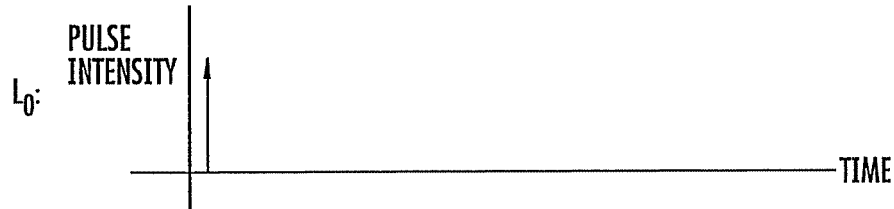
FIG. 3D is a graph of an exemplary excitation or pushing pulse used in the region of acoustic excitation for SWEI imaging according to an embodiment of the presently disclosed subject matter.
Figure 3E:
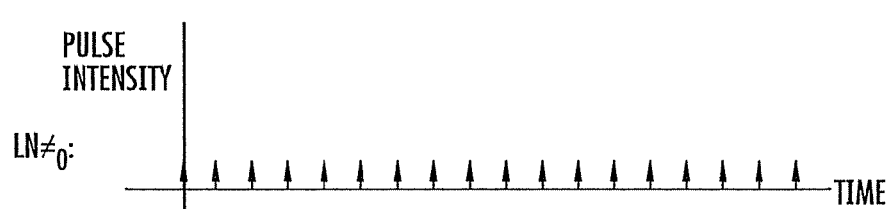
FIG. 3E is a graph of an exemplary reference pulse sequence used outside the region of acoustic excitation for SWEI imaging according to an embodiment of the presently disclosed subject matter.
Figure 4A:
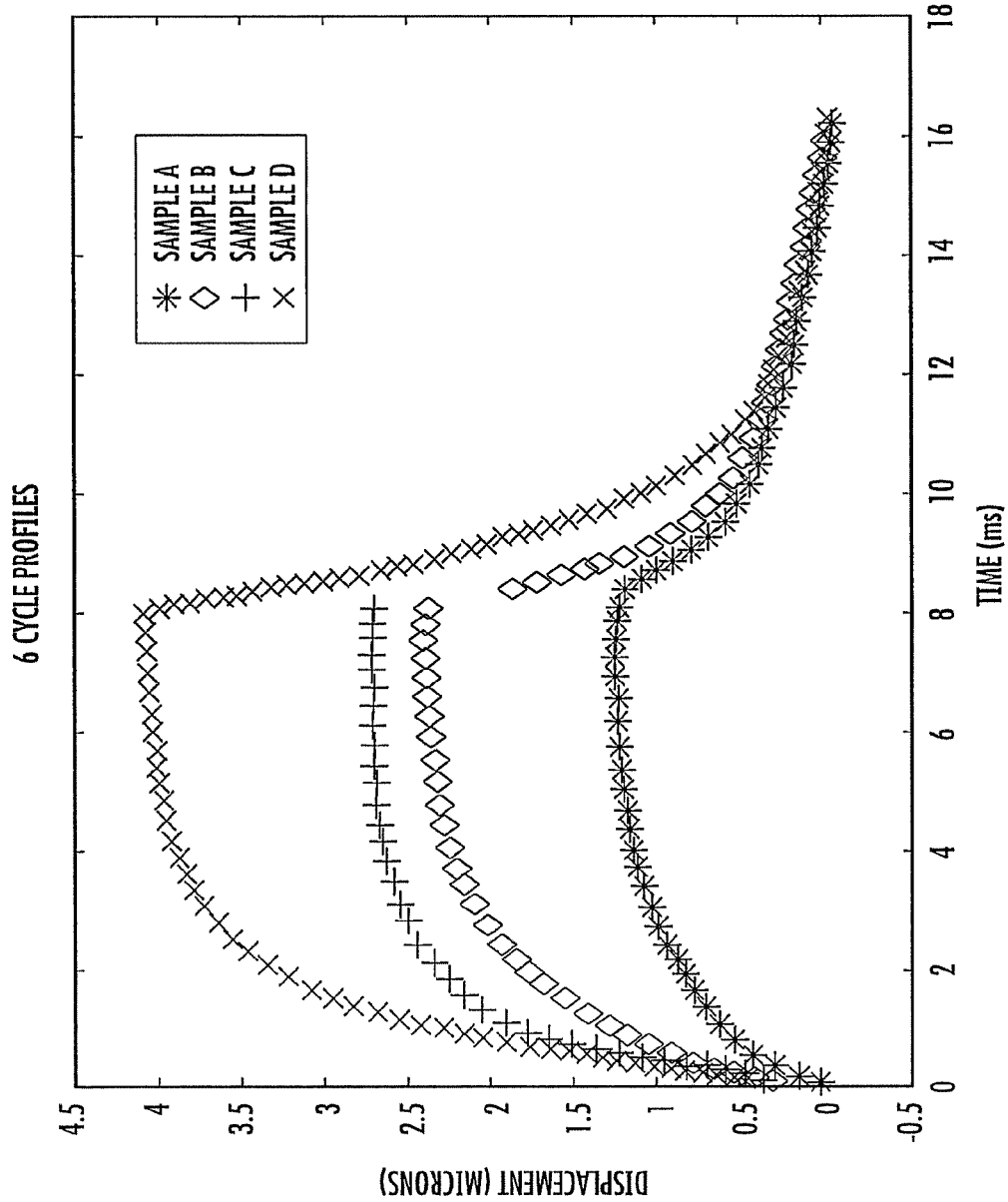
FIGS. 4A through 4D are representative displacement profiles with fitted model for gelatin phantoms of different elastic modulus values from 6-cycle, 8-cycle, 10-cycle, and 12-cycle MSSER imaging beam sequences, respectively.
Figure 4B:
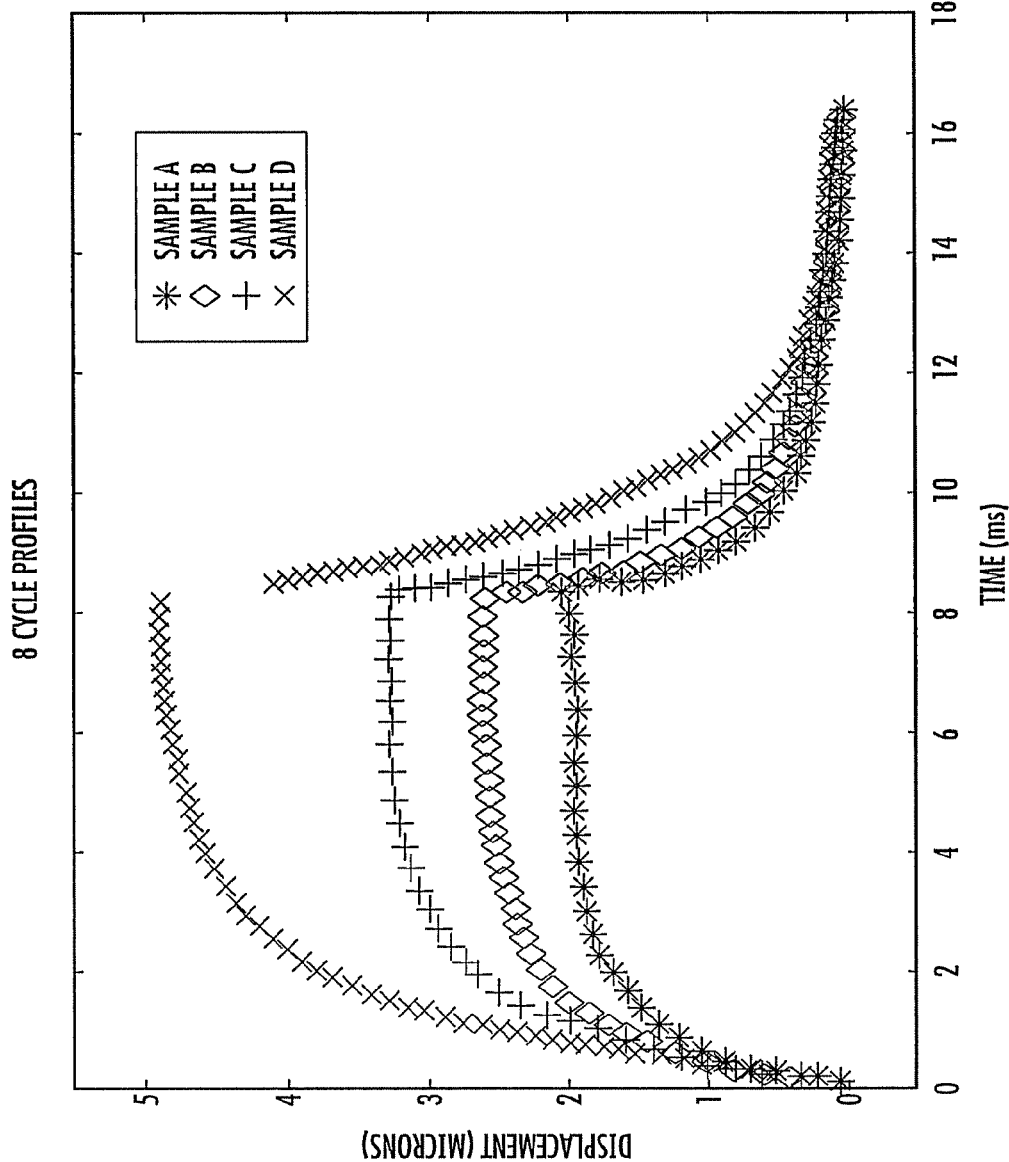
Figure 4C:
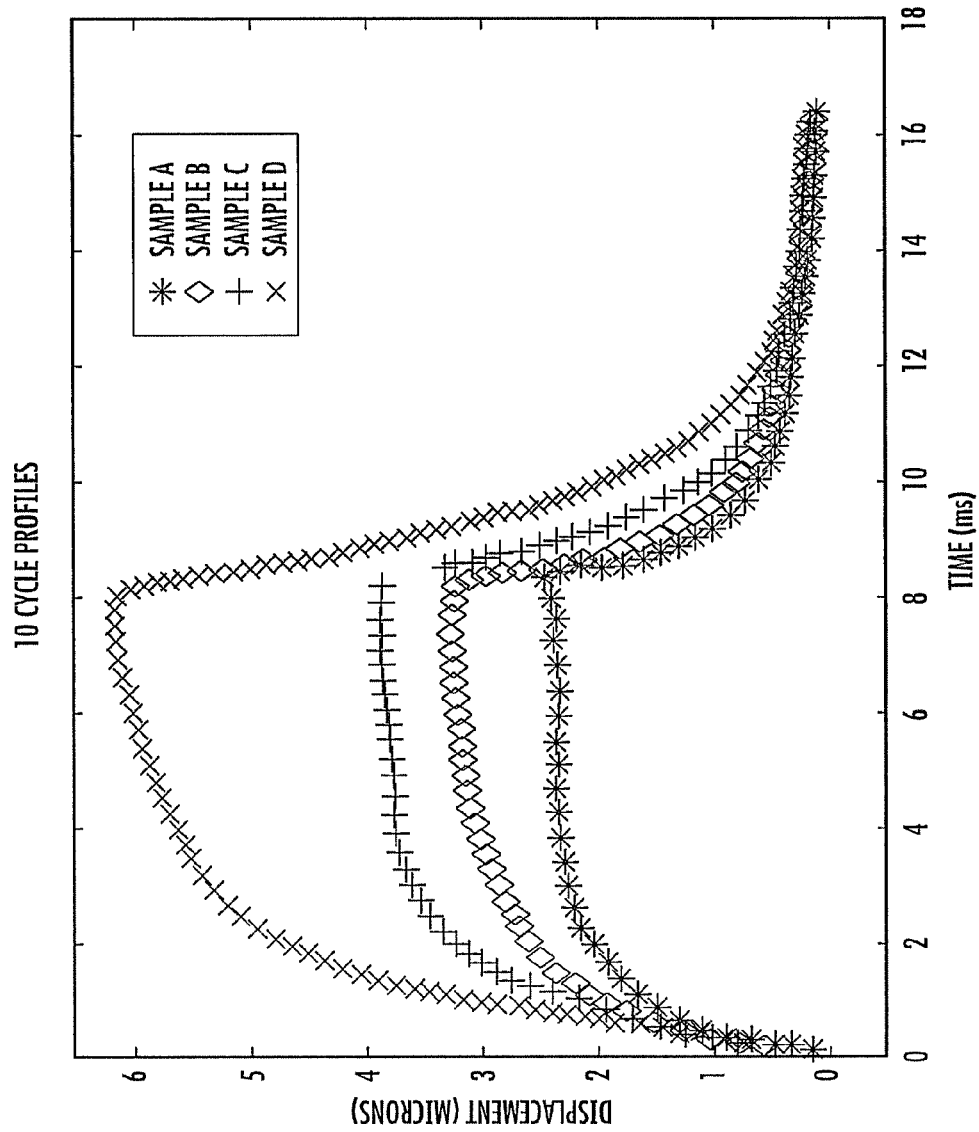
Figure 4D:
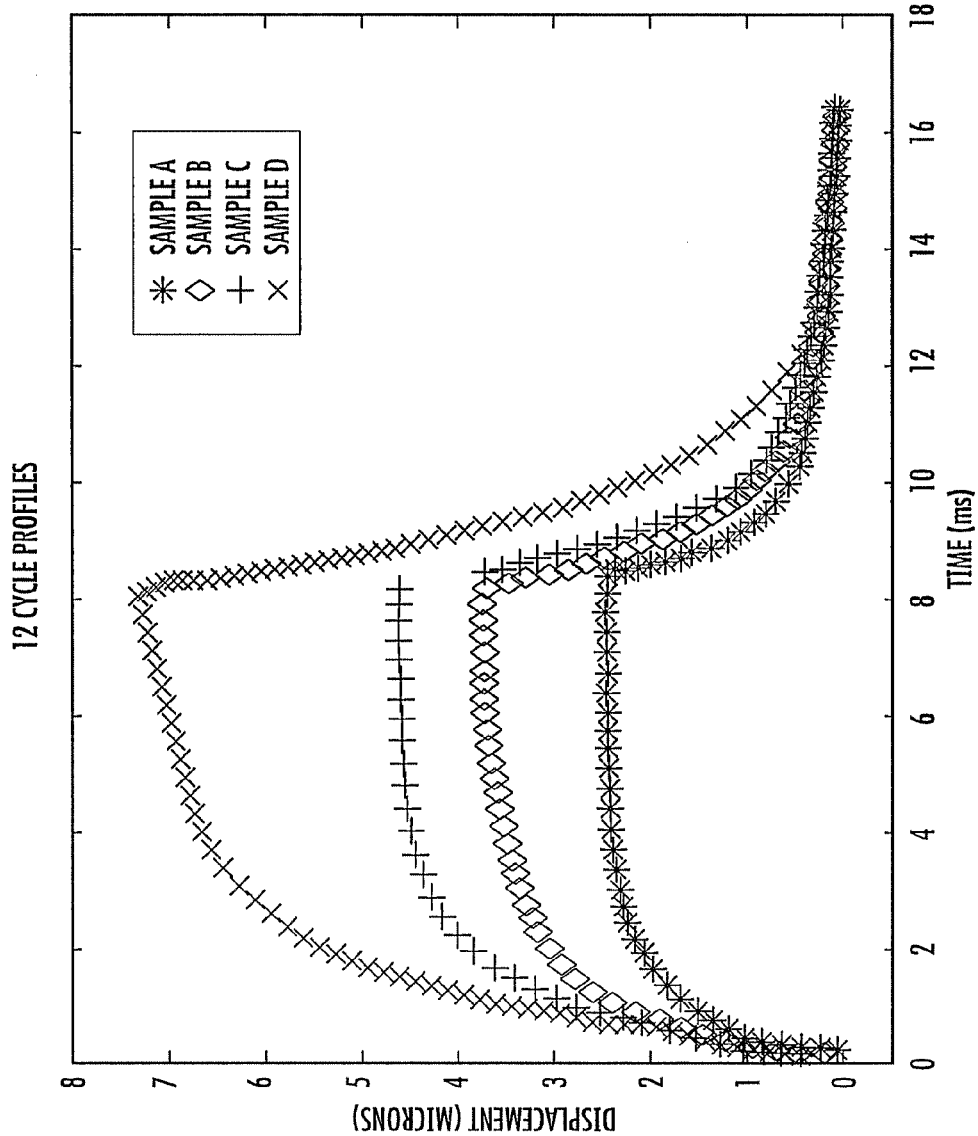

SWEI was performed using the same transducer, focal configuration, axial focus, frequencies, and number of lateral locations. The distance between lateral locations was 1.06 mm, twice that of MSSER. The SWEI beam sequence fired two reference tracking pulses, one 300-cycle (52 μs) pushing pulse, and then 123 tracking pulses to monitor induced displacements in positions lateral to the region of radiation force excitation. FIGS. 3D and 3E illustrate exemplary excitation and reference pulses used for SWEI imaging. In FIG. 3D, it can be seen that in SWEI imaging, only the pushing pulse occurs at location $L_0$. From FIG. 3E, the reference pulses occur at locations lateral to location $L_0$. Unlike conventional ARFI imaging beam sequences, the SWEI pushing pulse location remained stationary while tracking locations were translated across the FOV. The same one-dimensional cross-correlation methods were used to calculate axial displacements. At each spatial location in the FOV, a shear wave velocity was calculated as lateral distance from the excitation focus divided by time to peak displacement. Assuming a linear, elastic solid and constant density, the shear wave speed ($c_T$) can be related to Poisson's ratio (v), density (ρ), and elastic modulus (E) [31]:

$$c_T = \sqrt{\frac{E}{2(1+v)\rho}} \quad (15)$$

Conventional ARFI imaging was performed with generally the same imaging parameters as for SWEI. The number of lateral locations was increased to 40, while lateral spacing for conventional ARFI was 0.531 or half of the lateral spacing for SWEI. Conventional ARFI sequences used two reference tracking pulses, one 300-cycle (52 μs) pushing pulse, and then 60 tracking pulses.

B. Homogeneous Gelatin Phantoms

Four tissue mimicking, gelatin-based phantoms made with different concentrations of gelatin to vary stiffness were used to test the methods and systems described herein. Elastic modulus values resulting from mechanical testing for each of four gelatin samples are shown in Table I below. Methods for determining the elastic modulus values are described below. MSSER imaging was performed on each gelatin sample with separate acquisitions using 6-cycle, 8-cycle, 10-cycle, or 12-cycle pushing pulses.

TABLE I

Measured Elastic Modulus Values from Mechanical Testing for Different Homogeneous Gelatin Phantom Materials

| Gelatin Phantom | Elastic Modulus (kPa) |
|---|---|
| Sample A | 18.7 ± 0.4 |
| Sample B | 13.6 ± 0.4 |

TABLE I-continued

Measured Elastic Modulus Values from Mechanical Testing
for Different Homogeneous Gelatin Phantom Materials

| Gelatin Phantom | Elastic Modulus (kPa) |
| --- | --- |
| Sample C | 10.6 ± 0.3 |
| Sample D | 4.7 ± 0.1 |

To implement the first approach to approximating E (by estimating c, α, and I to calculate |F|), speeds of sound and attenuation coefficients in the phantoms were measured. The measured values agreed with published values [35], [36]. Because nonlinear propagation of MSSER pushing pulses in water did not allow measurement of the acoustic intensity directly, measures of temporal averaged intensity were made using the comparison method described in Palmeri et al. [31]. $I_{SPTA}$ of low amplitude MSSER imaging pulses was measured with an Onda HGL-0200 hydrophone produced by Onda Corporation, Sunnyvale, Calif. Displacements at the focus of a compliant gelatin phantom were then observed for low- and high-power radiation force application. By assuming a linear relationship between intensity and displacement, the ratio of the displacements from high-power to low-power settings represented the ratio of $I_{SPTA}$ between high-power and low-power settings. Using the speed of sound, attenuation, and intensity measurements, the force magnitude for each pushing pulse in the gelatin phantoms was estimated. Equation (12) was than used to translate estimated body force magnitude to units of estimated stress $\tilde{\sigma}$. The axial length over which the body force acts $L_{Axial}$ [m] from Equation (12) was estimated as the −6 dB (full width at half maximum) (FWHM) width of the MSSER pushing pulse.

To implement the second approach of approximating A discussed above from an independent estimate of the elastic modulus, SWEI was performed immediately after MSSER data acquisition without moving the transducer with respect to the sample. The resulting displacement profiles from radiation force imaging were fit to the Voigt function (Equation (3)), which was defined in custom MATLAB (Mathworks Inc., Natick, Mass.) code. In particular, the fitting between the model function and actual data was performed using MATLAB function 'fminsearch'. Parameter values were extracted directly from the output of the 'fminsearch' function.

To estimate strain from Equation (13) for a given MSSER acquisition, the steady-state displacement of the average representative displacement profile was measured. Representative displacement profiles were displacement profiles with a correlation coefficient greater than 0.975 to the nonlinear least squares fit to the Voigt model and were located within an axial region directly above the focus (e.g., a 2.5 mm region). The original length of tissue that was displaced by radiation force excitation $L_0$ was estimated as the FWHM width of the force distribution across the axial range in all samples. Equations (14) and (9) were then used to estimate A.

Within 24 hours of ARFI and SWEI imaging, the gelatin phantoms were mechanically tested using a BOSE EnduraTEC ELF 3200 produced by BOSE Corporation, ElectroForce Systems Groups, Eden Prairie, Minn. to quantify the elastic modulus of the samples (Table I). The load frame was fitted with a 225 N load cell and stainless steel axial compression platens. The force resolution for the load cell was 0.01 N. Cylindrical phantoms approximately 20 mm in diameter and 10 mm in height were placed between the stainless steel plates and coated with mineral oil to allow for unconfined and approximately frictionless compression. Strains up to 15% were achieved at strain rates of less than 1.0% per second. This mechanical testing was performed at slightly slower strain rates than those estimated from MSSER (greater than 1.5% per second) to ensure that steady-state displacement was reached between incremental levels of compressive force. A linear least-squares regression was performed on the stress versus strain profiles, and the slope of the regression indicated the elastic modulus of each material sample.

Each material sample was then associated with a measured elastic modulus E, and an estimated stress versus estimated strain $\Delta\tilde{\sigma}/\Delta\tilde{\epsilon}$ was determined from MSSER. The correction coefficient C was determined using MSSER data from all gelatin samples simultaneously by fitting a least-squares linear regression of E versus $\Delta\tilde{\sigma}/\Delta\tilde{\epsilon}$ and determining the slope with a y-intercept value of zero. Using Equation (14), estimated elastic modulus $\tilde{E}$ values were determined. Similarly, by spatially registering SWEI measures of E to MSSER data, Equations (14) and (9) were used to estimate force magnitude, A. Other viscoelastic parameters were determined by fitting MSSER data to the Voigt model described by Equation (3), and parametric images were rendered. It is noted that although this approach discloses fitting the displacement profiles to the Voigt function, this approach can be used to fit the collected date with other material models (e.g., the standard linear model).

C. Excised Pig Muscle

In another experimental example, an excised pig muscle sample was imaged using 6-cycle, 8-cycle, 10-cycle, and 12-cycle pushing pulse MSSER. SWEI and conventional ARFI imaging were also performed without moving the transducer with respect to the sample. The speed of sound and attenuation were assumed to be consistent with typical values for human tissue at 1540 m/s and 0.3 dB/cm/MHz, respectively. The mechanical testing, slope of the estimated stress versus estimated strain curve, and determination of the elastic modulus for the tissue sample were acquired using the same methods described above with respect to the testing of the homogeneous gelatin phantoms. An estimated elastic modulus $\tilde{E}$ from MSSER imaging was determined using Equation (14), and the same correction coefficient C value was determined from the gelatin phantoms. Because an initial deflection was observed from MSSER imaging, the pig tissue sample displacement profiles were fit to the standard linear model as described in Equations (5) through (8) using the 'fminsearch' function in MATLAB, as described herein above for the Voigt model.

Results

A. Homogeneous Gelatin Phantoms

Representative displacement profiles from MSSER imaging are shown in FIG. 4 for acquisitions using 6-cycle (FIG. 4A), 8-cycle (FIG. 4B), 10-cycle (FIG. 4C), and 12-cycle (FIG. 4D) pushing modulus values described in Table I. Representative profiles corresponded to the average displacement profile within a 2.5 mm axial region directly above the imaging focus that had a correlation coefficient greater than 0.975 to the nonlinear least squares fit of the profile to the Voigt model. The fitted model is presented as a dashed line, while representative displacement data from each sample are displayed in open symbols.

Figure 5:
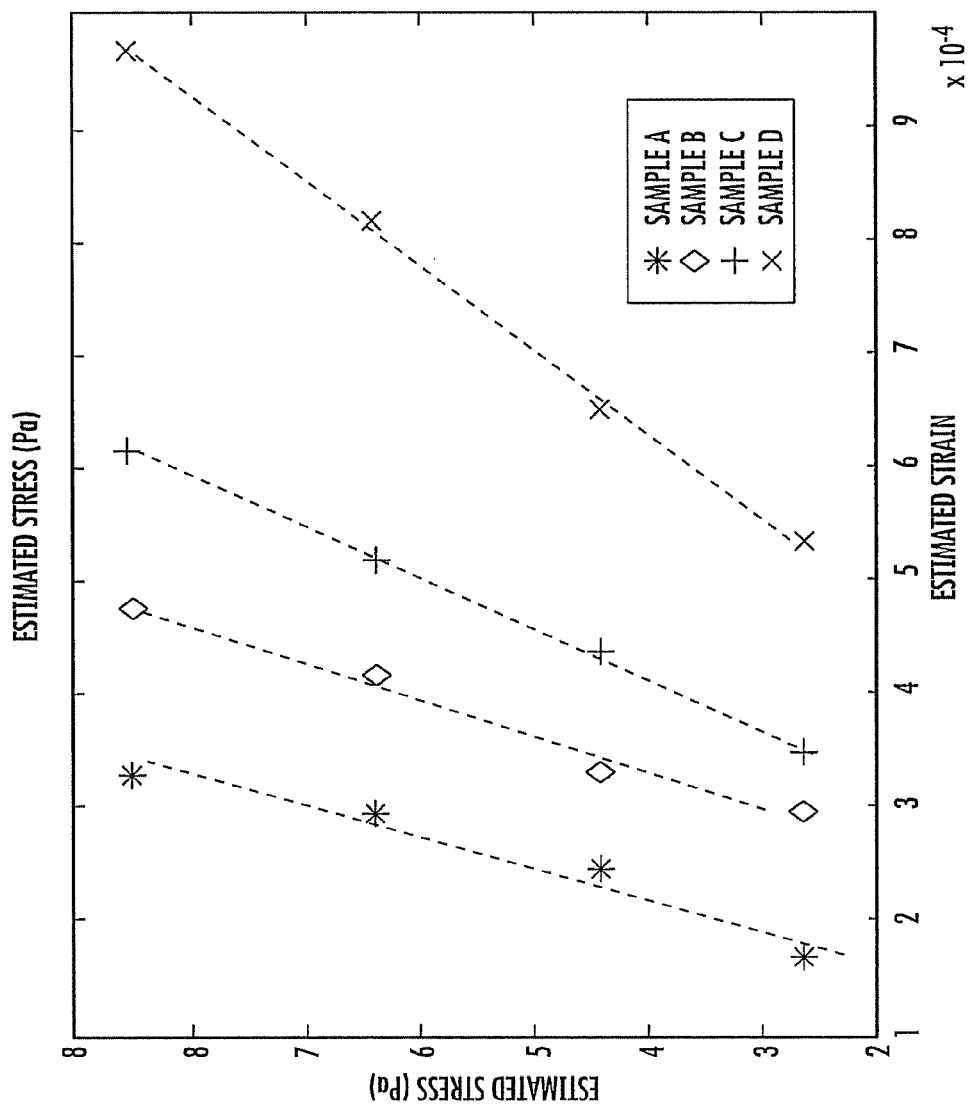
FIG. 5 is a graph of estimated stress versus estimated strain values for gelatin phantom materials with linear fits.

FIG. 5 shows the estimated stress versus estimated strain data for each gelatin sample. Estimated stress values were calculated from Equations (10) and (12) for each of the 6-cycle, 8-cycle, 10-cycle, and 12-cycle MSSER imaging acquisitions. A linear least-squared fit is illustrated as dashed lines while estimated stress and strain data are shown as open symbols. Estimated strains were computed from Equation (13) where the steady-state displacement for each acquisition is taken from the representative profile data shown in FIG. 4.

Figure 6:
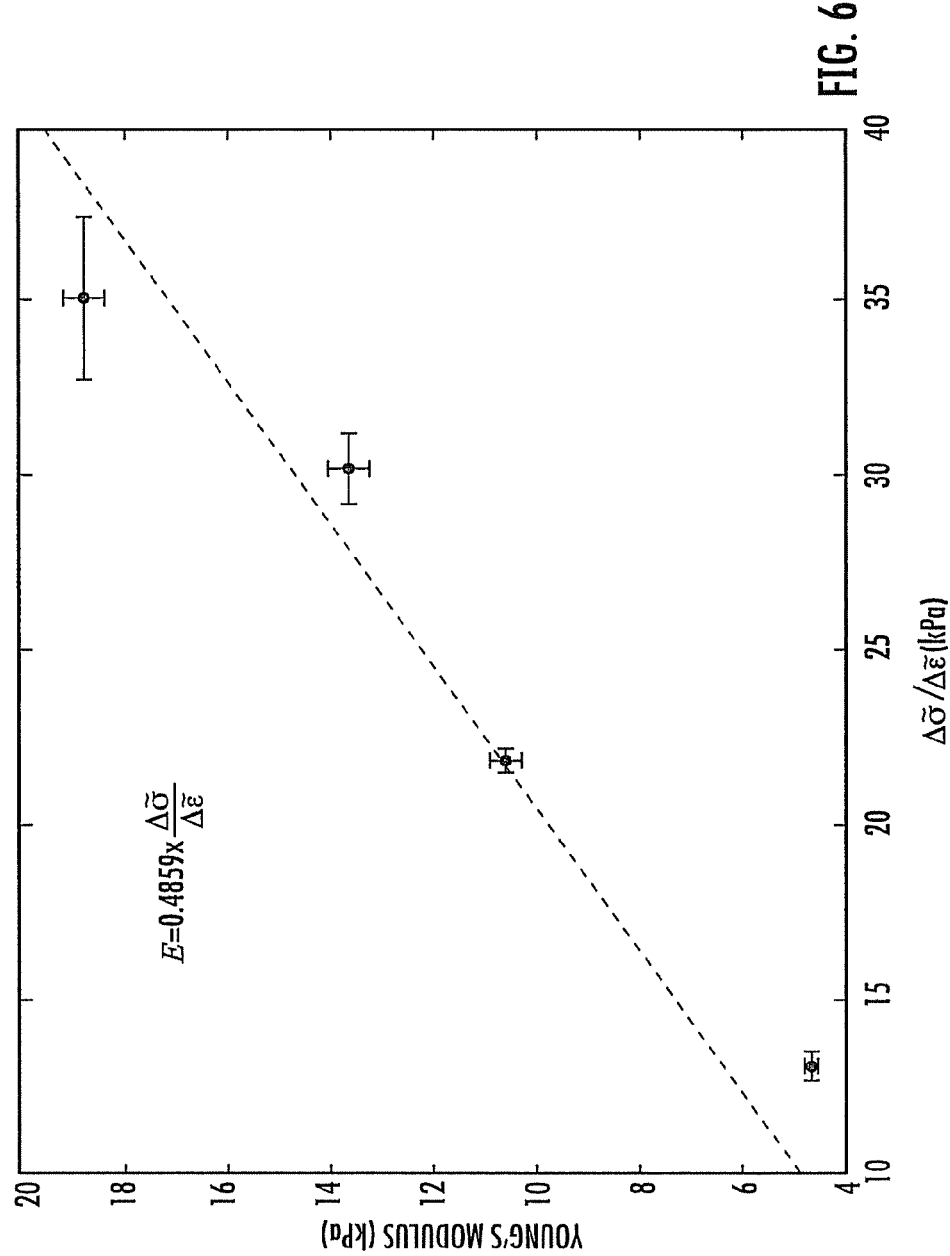
FIG. 6 is a graph of the measured elastic modulus values from uniaxial compression and estimated stress versus estimated strain data from MSSER imaging for gelatin phantom materials.

FIG. 6 shows the elastic modulus values from mechanical testing (Table I) plotted against the slope of the least-squared fits to the estimated stress and strain data from FIG. 5. The dashed line represents a linear least-squared fit with y-intercept of zero while the elastic modulus data are represented as points with standard deviation bars. The slope of the linear least-squared fit was 0.4859 and represented the value for the correction coefficient C in Equation (14). Using this value and the estimated stress and strain data from FIG. 5, estimated elastic modulus values $\tilde{E}$ were calculated from Equation (14) and are reported in Table II. Also included in Table II are elastic modulus values determined from mechanical testing and average elastic modulus values determined from SWEI.

TABLE II

Comparison of Elastic Modulus Values from Mechanical Testing and Radiation Force Methods

| Gel Phantom | Enduratec E (kPa) | SWEI E (kPa) | MSSER $\tilde{E}$ (kPa) |
|---|---|---|---|
| Sample A | 18.7 ± 0.4 | 18.4 ± 2.2 | 17.1 ± 2.3 |
| Sample B | 13.6 ± 0.4 | 12.6 ± 1.3 | 14.7 ± 1.0 |
| Sample C | 10.6 ± 0.3 | 8.5 ± 0.8 | 10.6 ± 0.3 |
| Sample D | 4.7 ± 0.1 | 5.5 ± 0.6 | 6.3 ± 0.4 |

Figure 7:
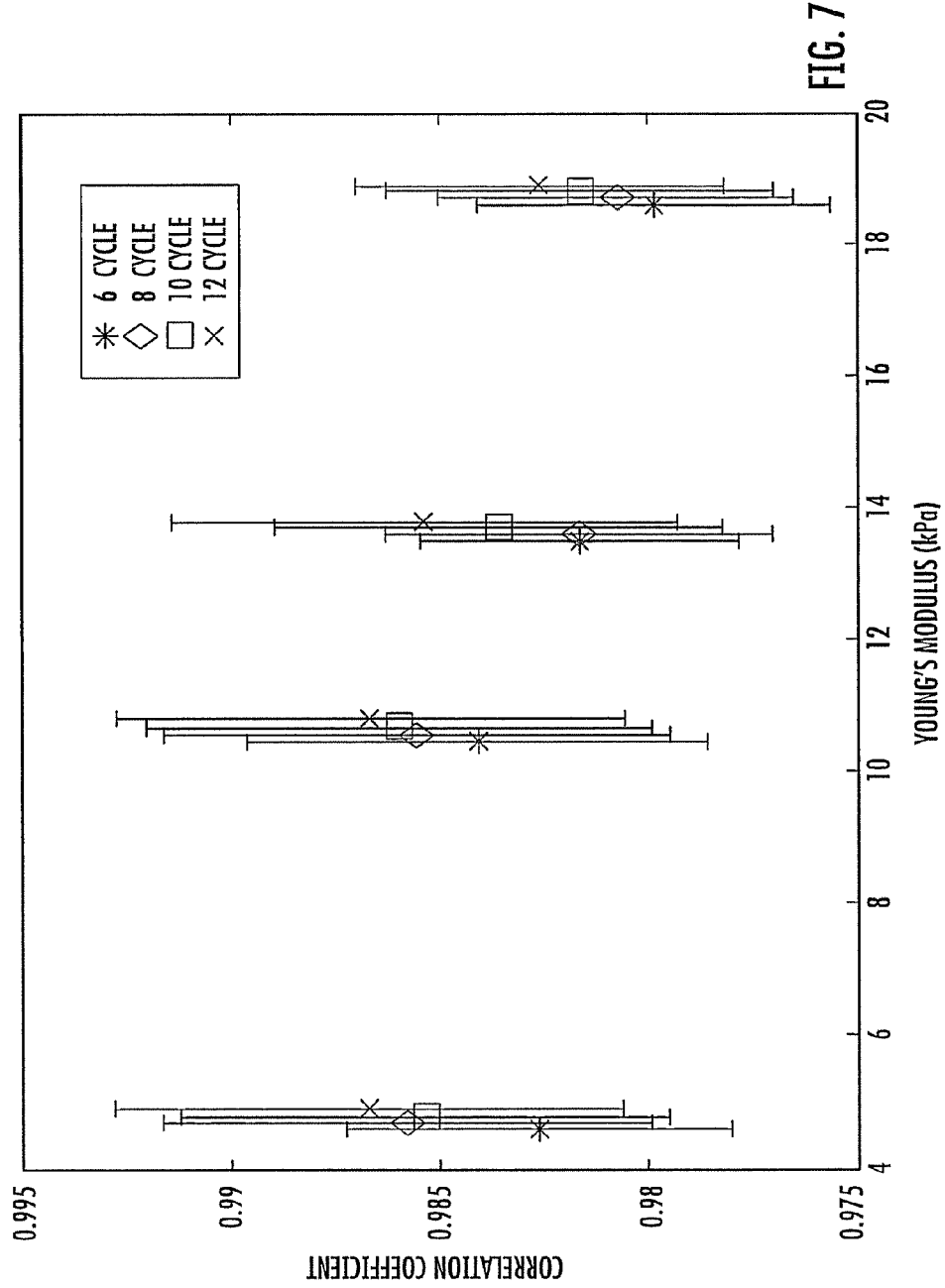
FIG. 7 is a graph of correlation coefficients±standard deviation compared with elastic modulus for gelatin phantom material displacement profile data fitted to the Voigt model.
Figure 8A:
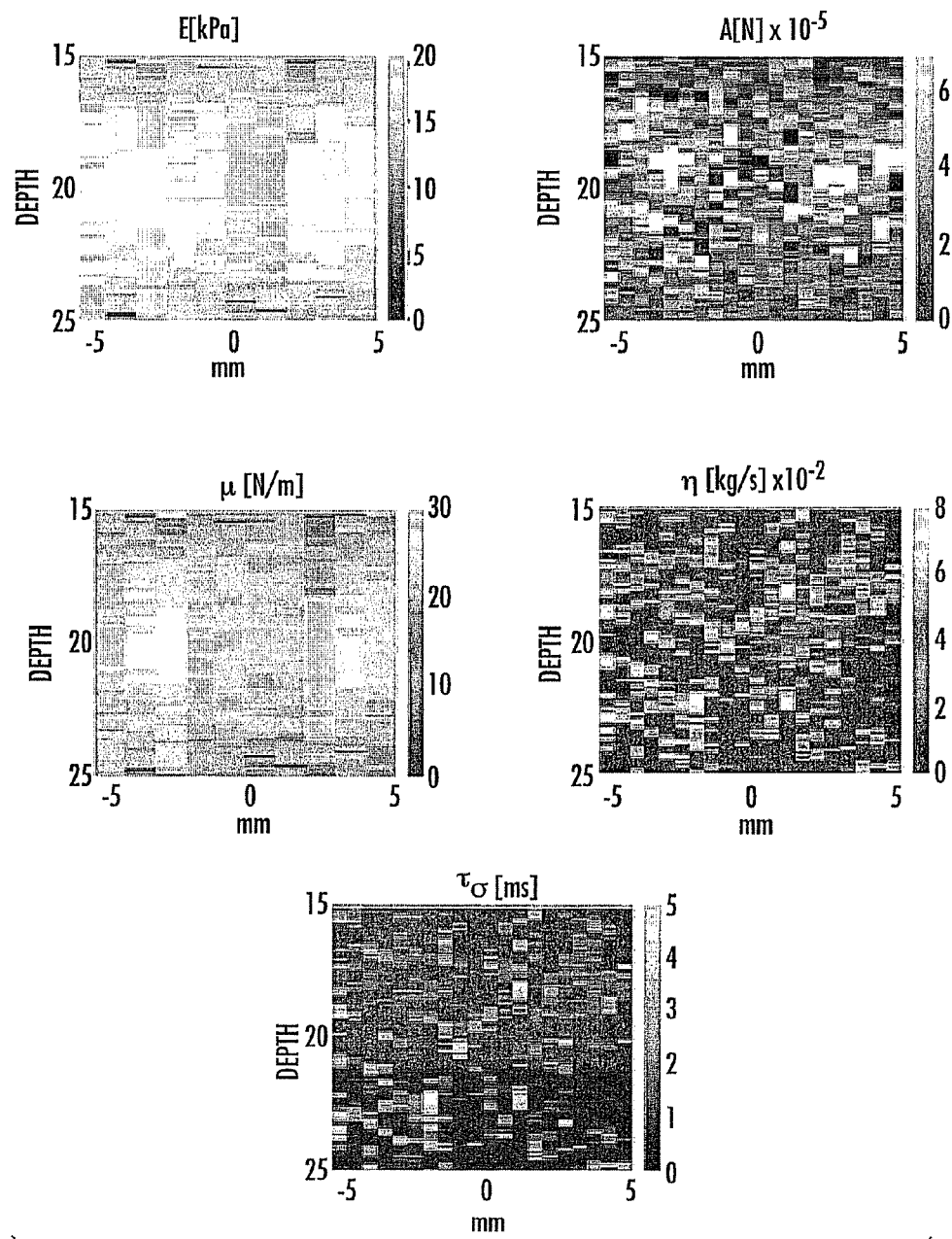
FIG. 8 illustrates parametric images of homogeneous gelatin phantom materials from SWEI and a combined SWEI and MSSER approach according to an embodiment of the presently disclosed subject matter.
Figure 8B:
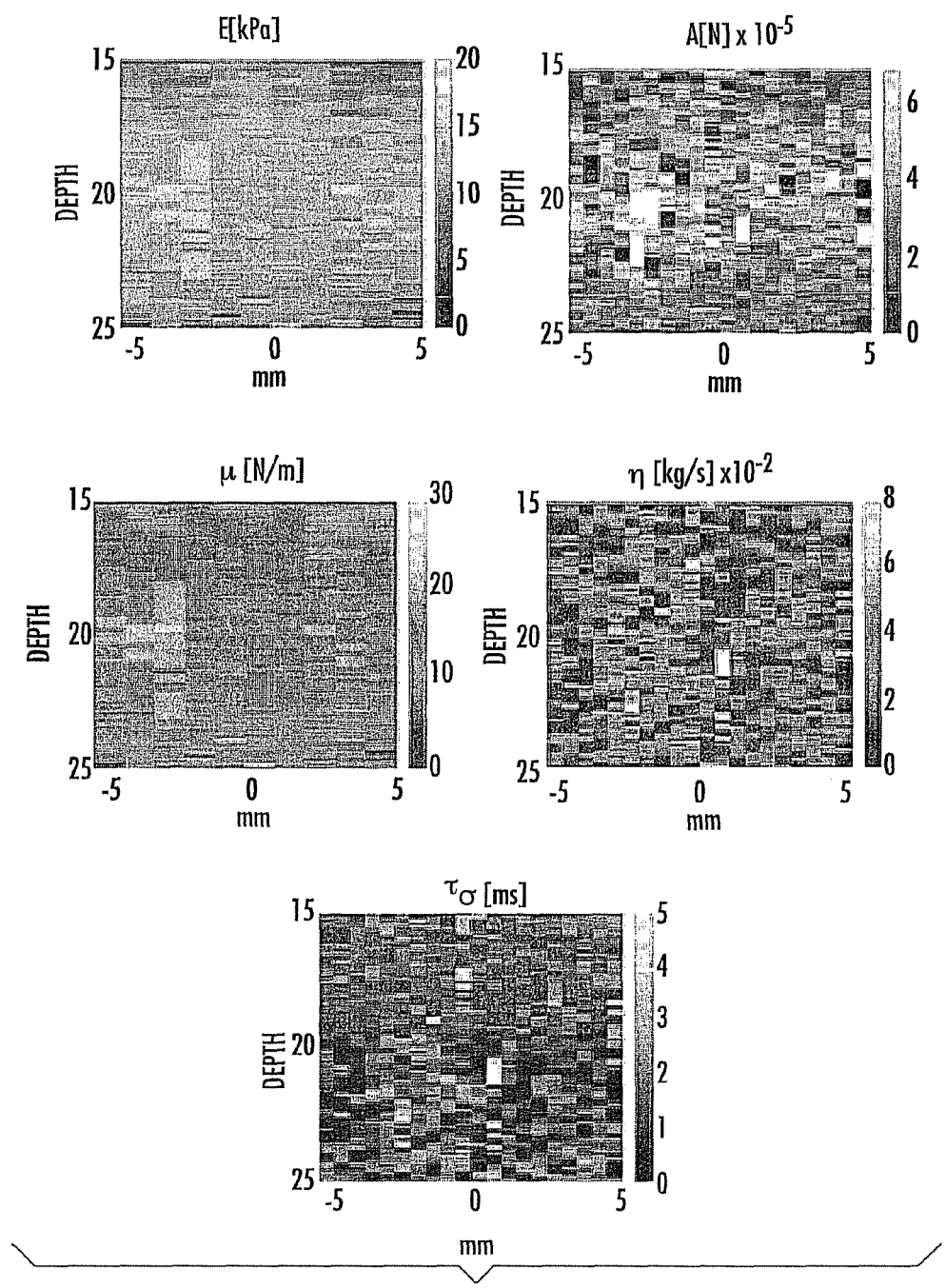
Figure 8C:
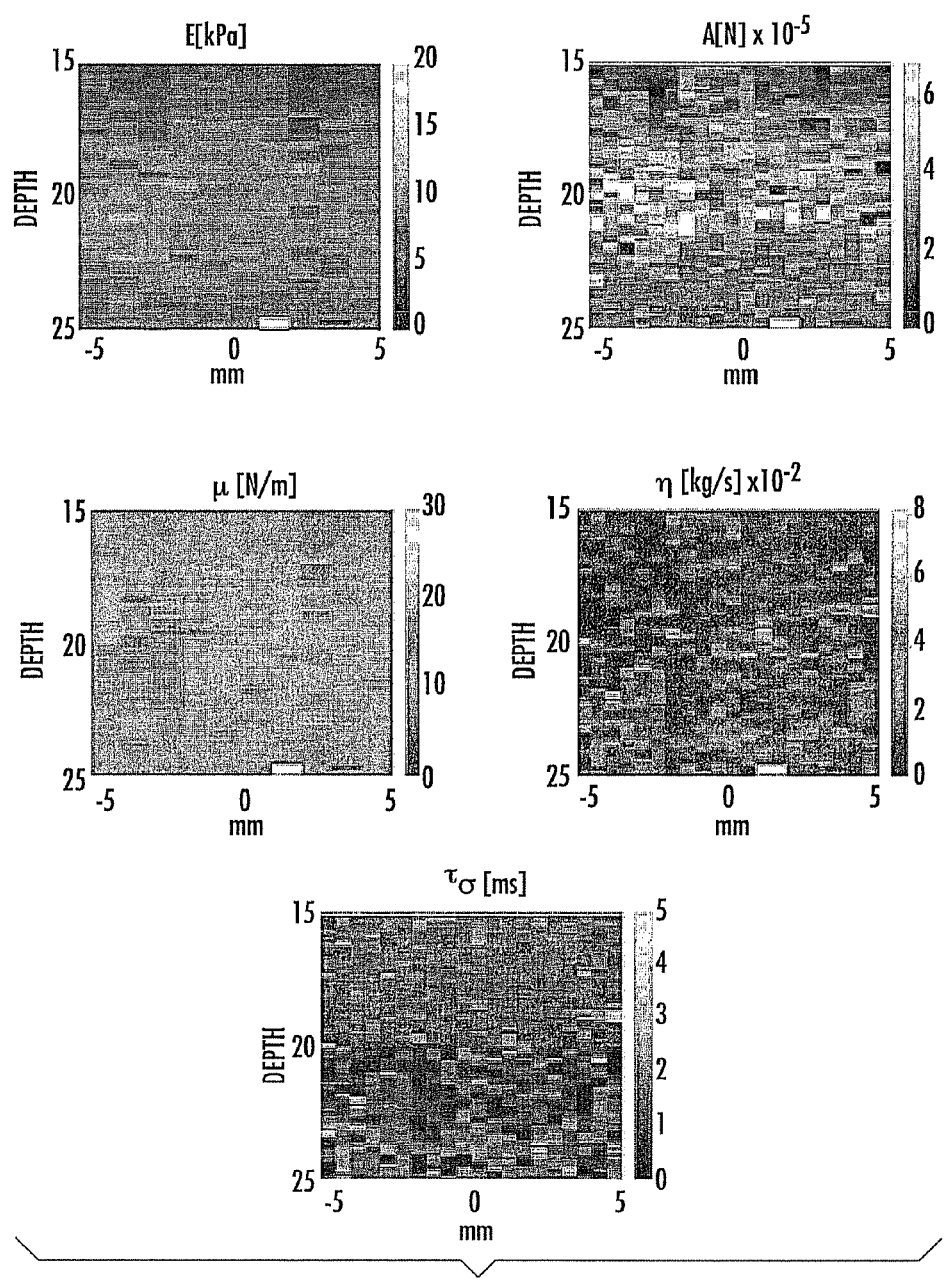
Figure 8D:
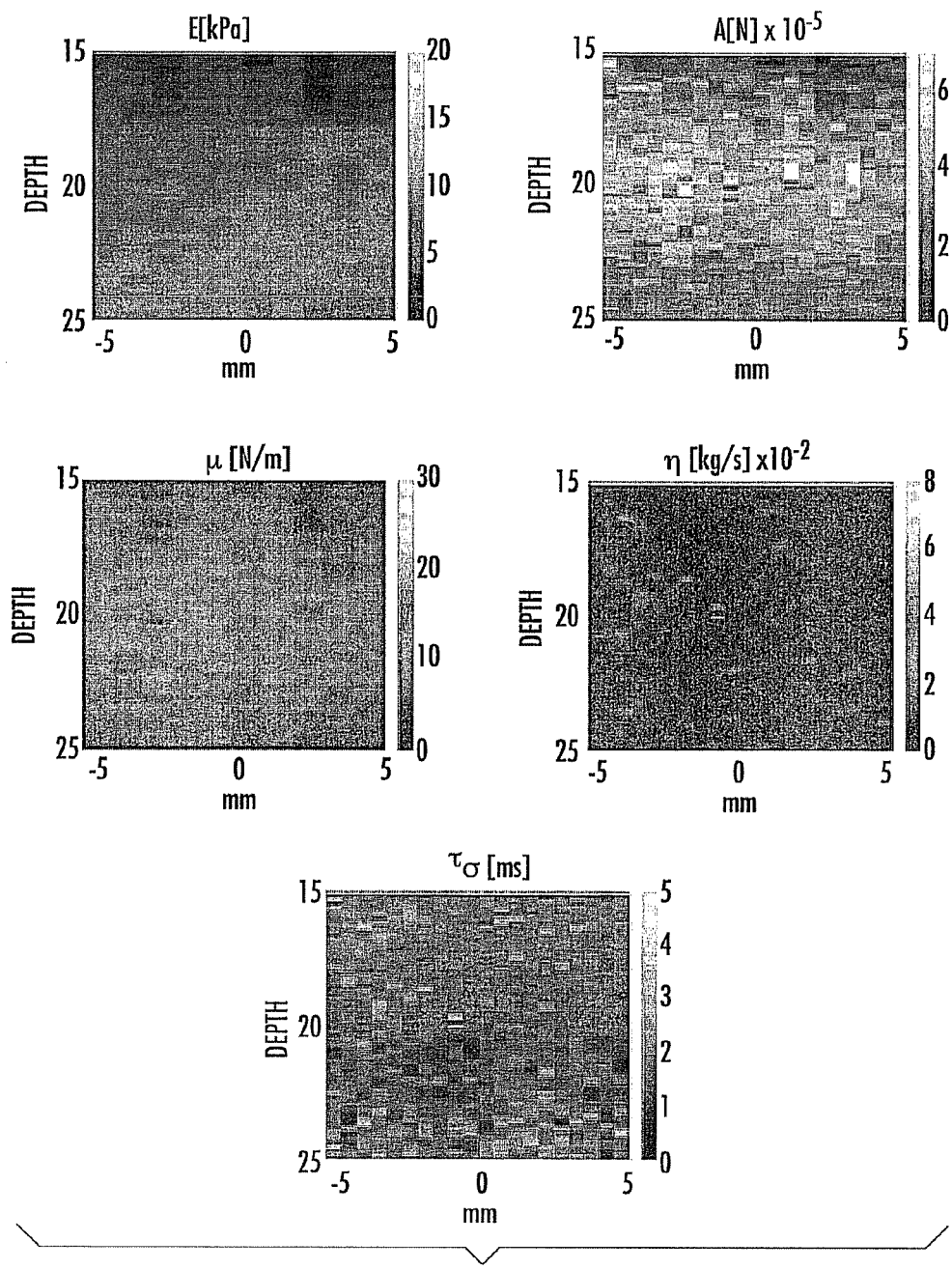
Figure 9A:
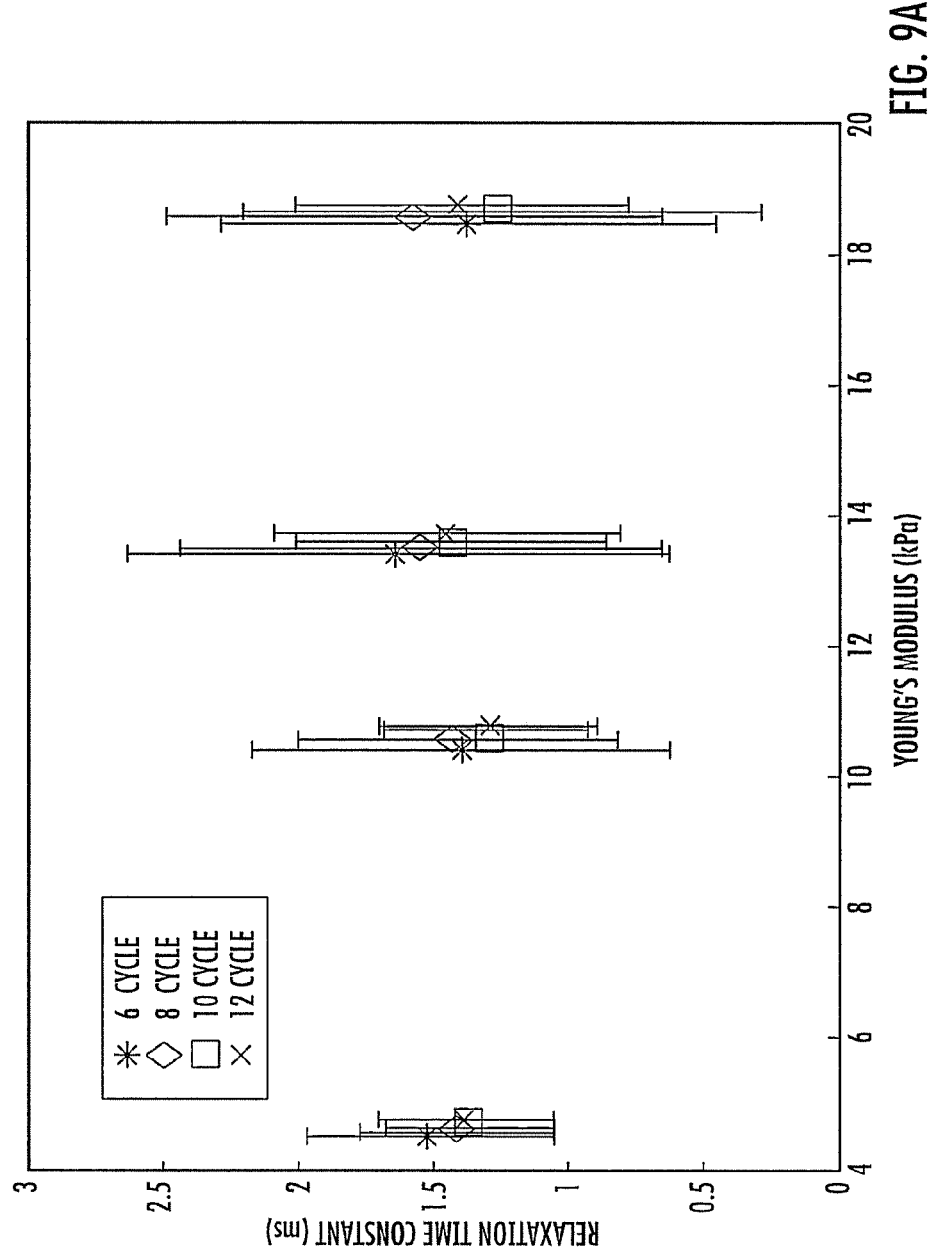
FIGS. 9A through 9D are graphs of parameters of the Voigt model calculated from SWEI measures of elastic modulus and MSSER displacement profiles over a 2.5 mm range directly above the imaging focus for gelatin phantom samples according to an embodiment of the presently disclosed subject matter.
Figure 9B:
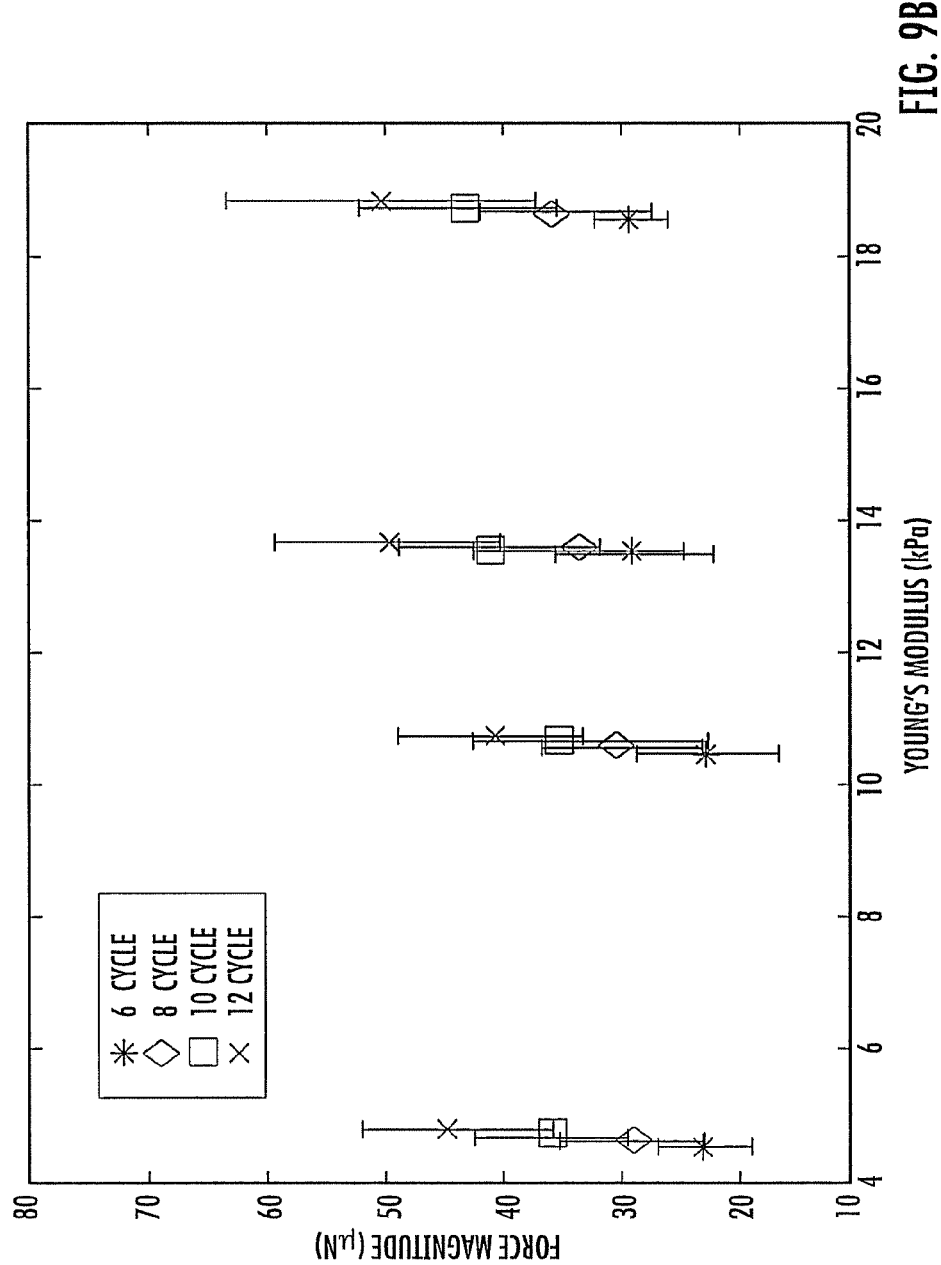
Figure 9C:
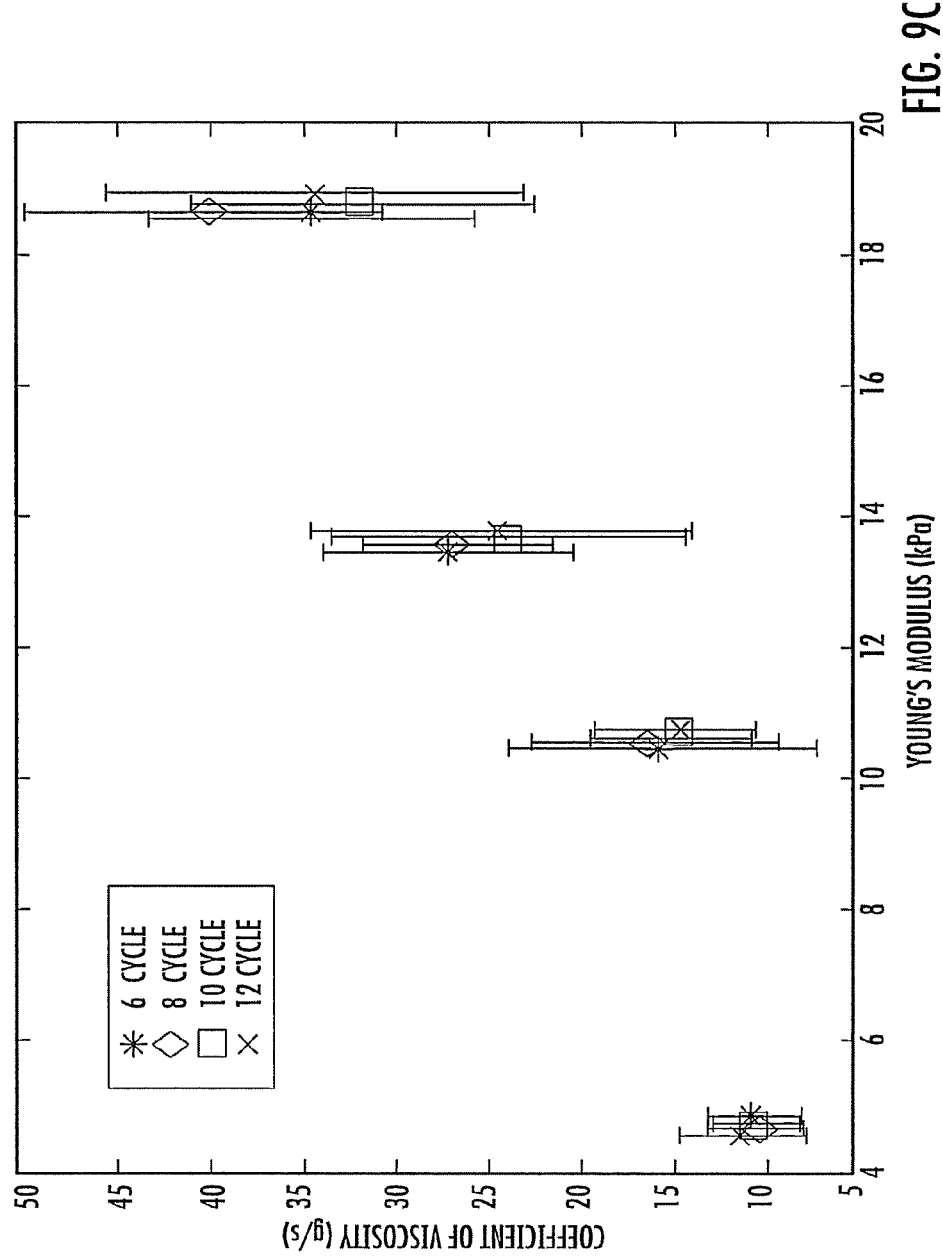
Figure 9D:
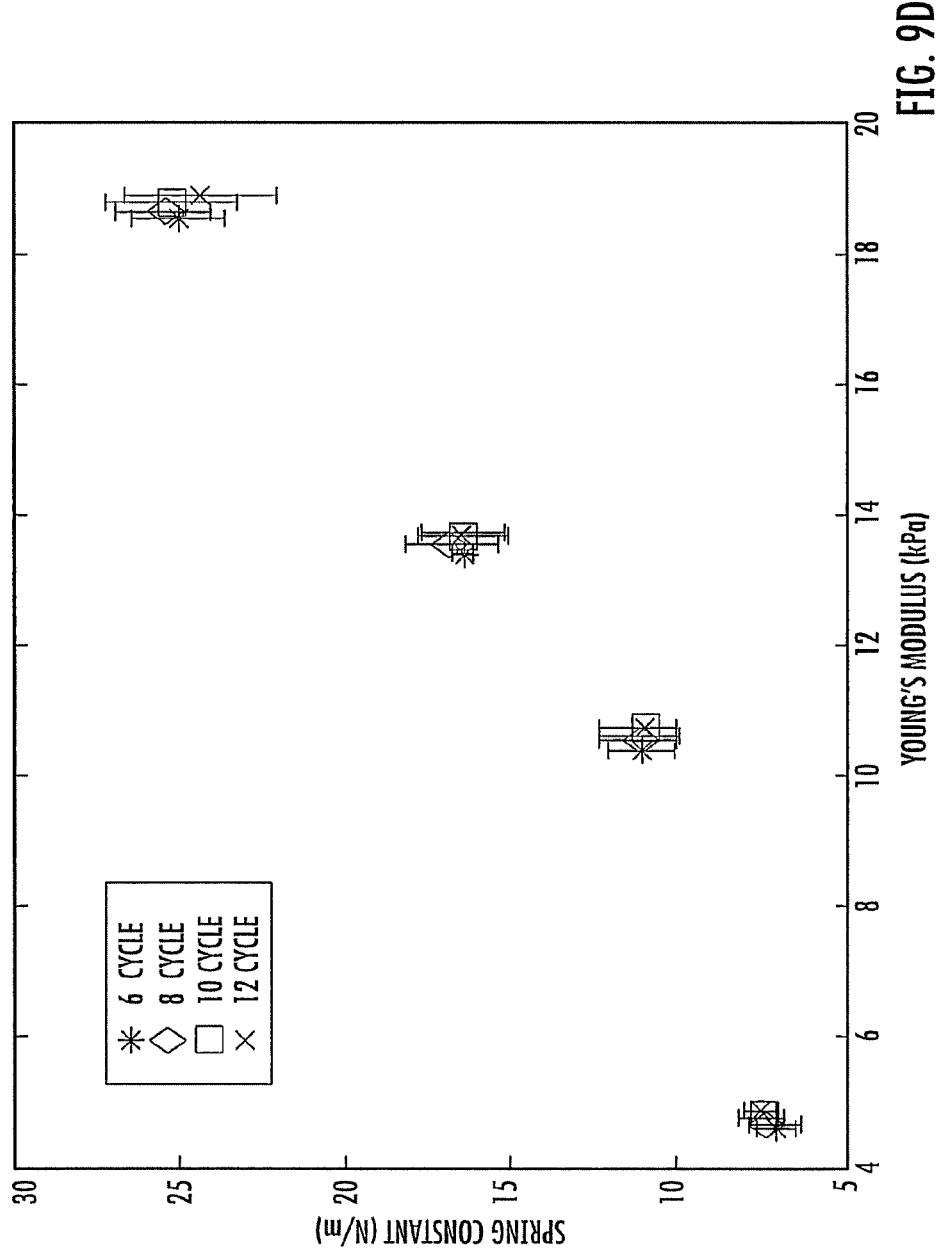

Mean correlation coefficient values with standard deviations for the representative displacement profiles are displayed in FIG. 7. Values are plotted versus elastic modulus of the gelatin phantom samples. The duration of MSSER pushing pulse is shown in open symbols.

In FIG. 8, parametric images of gelatin phantoms are rendered from spatially registered SWEI and 12-cycle pushing pulse MSSER imaging data with an imaging focus of 20 mm. Columns are labeled with the viscoelastic parameter of interest while rows have figure numbers that include the name of gelatin sample. For example, the row labeled FIG. 8A corresponds to imaging data from gelatin phantom Sample A. In the first column, elastic modulus images are depicted from SWEI data spatially registered to the lateral span of MSSER imaging. As described above, the lateral span and spacing between lateral beams in SWEI were twice as much as in MSSER imaging. Using the SWEI measures of the elastic modulus, the Voigt model fits to the MSSER displacement profiles, and Equations (9) and (14), parametric images of mechanical parameters are shown depicting force magnitude A [N] (second column), spring constant $\mu$ [N/m] (third column), coefficient of viscosity $\eta$ [kg/s] (fourth column), and relaxation time constant for constant stress $\tau_\sigma$ [s] (fifth column). It is important to note that quantitative numeric values are determined for the mechanical parameters. Unlike conventional techniques which determine mechanical properties of samples qualitatively (e.g., relative to those of other samples), the values computed using the methods described herein are in absolute or non-relative terms. By performing the curve fitting from the displacement data and estimating the applied force magnitude described above, the equations for the viscoelastic model can be solved for viscoelastic parameters, such as elasticity (spring constant) and viscosity coefficient.

FIGS. 9A-9D respectively illustrate average values for relaxation time constants for constant stress $\tau_\sigma$ [s], force magnitude A [N], coefficients of viscosity $\eta$ [kg/s], and spring constants $\mu$ [N/m] as a function of the elastic modulus and number of cycles used for pushing pulses in MSSER. Average values are shown in open symbols with error bars representing standard deviation. Values were computed over the same 2.5 mm range directly above the imaging focus as used in determining representative displacement profiles from FIG. 4.

B. Excised Pig Muscle

Figure 10:
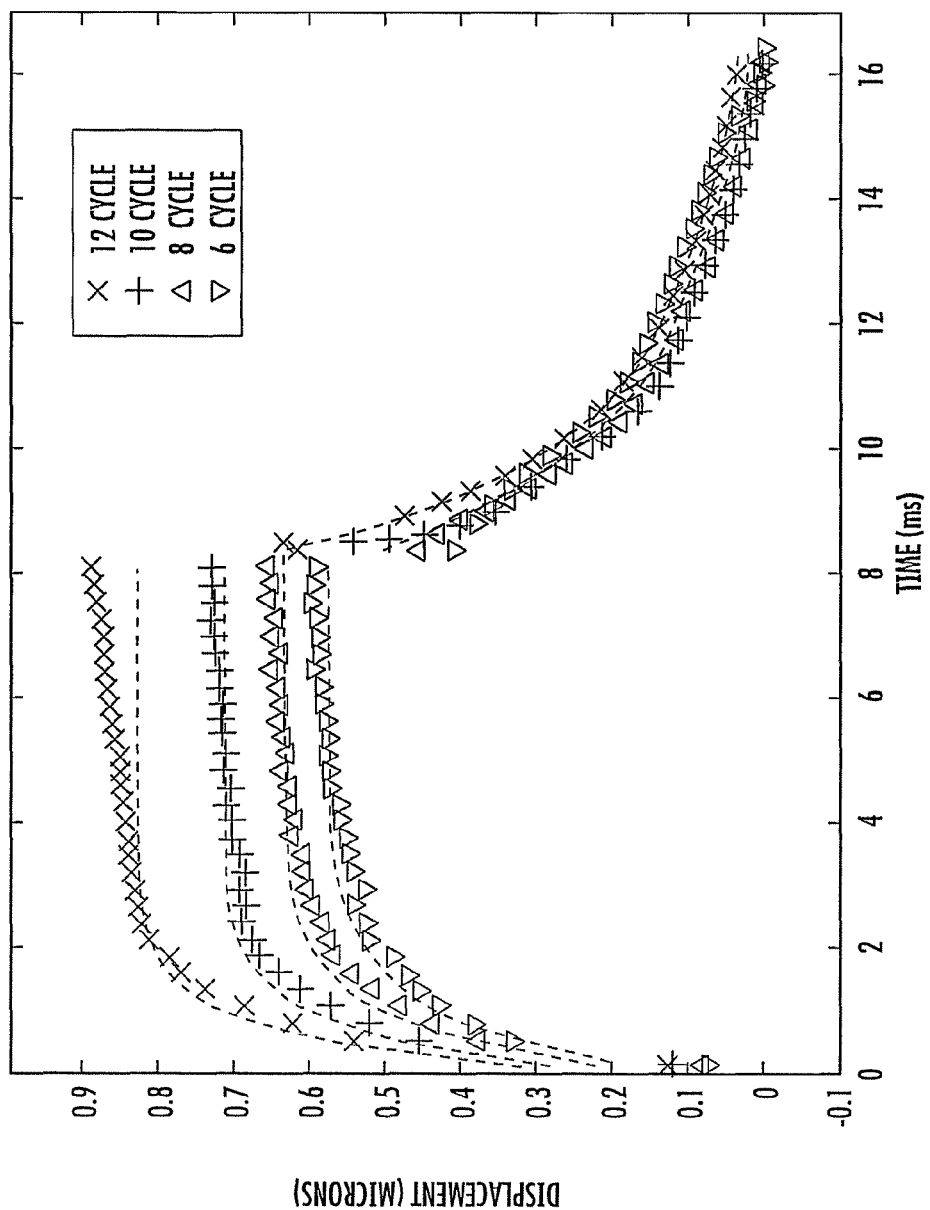
FIG. 10 is a graph illustrating representative displacement profiles with fitted standard linear model for excised pig muscle sample from different pushing pulse MSSER beam sequences according to embodiments of the presently disclosed subject matter.

Representative displacement profiles from MSSER imaging of excised pig muscle are shown in FIG. 10. Displacement data are in open symbols while the dashed lines represent a nonlinear least-squared fit to the Standard Linear model. As described above, the same correction coefficient C determined from the gelatin samples (FIG. 6) was used to calculate an estimated elastic modulus $\tilde{E}$ from the excised pig muscle sample. The mechanical testing elastic modulus, SWEI average elastic modulus, and MSSER estimated elastic modulus $\tilde{E}$ are listed in Table III.

TABLE III

Comparison of Elastic Modulus Values from Mechanical Testing and Radiation Force Methods

| Material | Enduratec E (kPa) | SWEI E (kPa) | MSSER $\tilde{E}$ (kPa) |
|---|---|---|---|
| Porcine Muscle | 129.3 ± 10.6 | 106.8 ± 18.7 | 122.4 ± 5.0 |

Figures 11A, 11B, 11C:
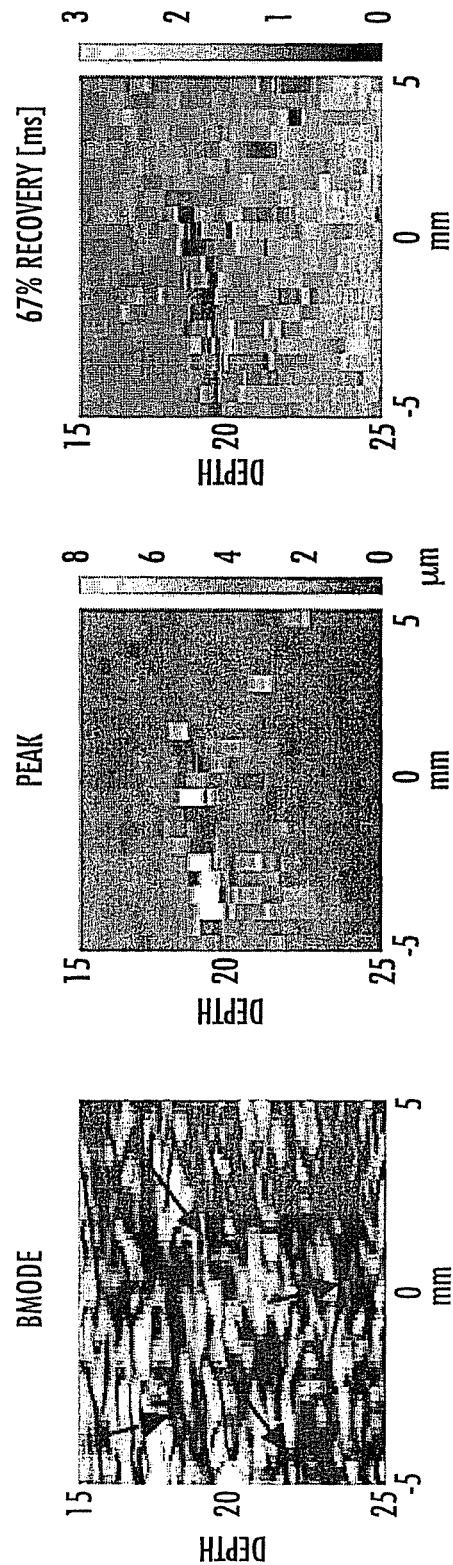

FIG. 11 illustrates (in FIG. 11A) a B-mode, and (in FIGS. 11B and 11C) conventional ARFI peak displacement and time to 67% recovery images of the excised pig tissue sample. MSSER and SWEI displacement data were fit to the standard linear model to render parametric images of (in FIG. 11D) force magnitude A, (in FIG. 11E) time constant for constant stress $\tau_\sigma$, (in FIG. 11F) time constant for constant strain $\tau_\epsilon$, and (in FIGS. 11G-11I) both spring constants $\mu_0$ and $\mu_1$ and the coefficient of viscosity $\eta_1$.

Discussion

In regard to the correction factor C in Equation (14), steady-state displacement underestimation, as well as errors in estimating $L_{Axial}$ and $L_0$ from Equations (12) and (13), can be accounted for in the estimation of the elastic modulus. It has been observed that the magnitude of displacement underestimation can be larger than 50% for the focal configurations and other imaging parameters used according to the systems and methods disclosed herein, although less than 50% displacement underestimation can be expected in the steady-state condition. In addition, discrete viscoelastic approximations do not account for distributed loads, which can reduce the overall displacement achieved at a given point. The FWHM of the radiation force footprint may not accurately represent the axial span over which the applied body force acts or the original length of tissue that displaces in response to radiation force excitation. These error sources are largely system dependent, and relative displacement underestimation can be estimated as constant for a given applied force.

Another source of error that may affect C to a smaller extent is the comparison method used for measuring I, which can overestimate the true focal intensity [31], [38]. Further, there may be a small amount of displacement relaxation that occurs between force cessation and the initiation of the tracking pulse. Elastodynamic models of tissue response to radiation force excitation [30], [31], [37] and typical relaxation time constants measured in the experimental analyses discussed above imply a worst case of 9% displacement relaxation. Because it is known that the material samples of interest are viscoelastic rather than purely elastic, a larger delay in force propagation can be expected, which can result in less relaxation before displacement tracking. Accordingly, C can be predominantly an imaging-system-dependent parameter and can be considered consistent across all imaging samples. In the experimental configurations discussed above. C was determined by using a least-squared linear fit between measured elastic modulus values $\tilde{E}$ and estimated stress versus estimated strain values $\Delta\tilde{\sigma}/\Delta\tilde{\epsilon}$ for each gelatin sample. The same C value is used consistently for all reported elastic modulus estimations $\tilde{E}$ and parametric images for both gelatin and excised pig muscle samples.

Using planar wave assumptions, the magnitude of acoustic radiation force can be proportional to temporal average intensity, attenuation, and the speed of sound (Equation (10)). Based on hydrophone experiments, it has been found that the attenuation of the gelatin phantoms used in the experiments discussed above was dependent primarily on the concentration of additive graphite, which was held constant in all samples. Because the speed of sound and attenuation were constant in all 4 gelatin samples, the effective magnitude of the mimicked temporal unit step force in MSSER imaging was proportional to the number of cycles (or temporal duration) transmitted per pushing pulse. Data in FIG. 4 depicted the response of gelatin phantom samples with different elastic modulus values (Table I) to an increasing number of pushing pulse cycles. The Voigt model shown in dashed lines fit the displacement data well, which indicated that the model is appropriate.

There are two trends that were apparent from this data. First, an increase in force magnitude applied to a given gelatin sample can result in increased steady-state displacement. This trend was apparent when displacement profiles from the same sample were compared from FIG. 4A (smallest force magnitude) to FIG. 4D (largest force magnitude). Second, for the same applied force magnitude, stiffer phantoms can exhibit a smaller steady-state displacement than more compliant gelatin phantoms, which was in agreement with our model at equilibrium (Equation (4)). These trends were further expressed in FIG. 5 where the force magnitude was expressed as an estimated stress $\tilde{\sigma}$, and steady-state displacement was scaled by an original length constant $L_0$, to be expressed as an estimated strain $\tilde{\epsilon}$. As phantom stiffness increased, the slope of estimated stress versus estimated strain became steeper.

Furthermore, the slope of the least-squared linear fits in FIG. 5 can generally be proportional to the mechanically tested elastic modulus values by a constant correction factor, C. The least squared solution for C was calculated from the gelatin phantom data and was displayed in FIG. 6. From FIG. 6, it was evident that data points from samples A, B, and D fell either above or below the linear regression. These errors were further reflected in Table II, where estimated elastic modulus values from MSSER imaging data (third column) for Samples A, B, and D did not exactly match the measured elastic modulus values from mechanical testing (first column). Although these values did not exactly match, they were generally consistent. Standard deviations for these measurements overlapped for all samples except for Sample D, and maximum error between estimated elastic modulus and measured elastic modulus was 1.6 kPa. Furthermore, when comparing MSSER elastic modulus estimates to those obtained from SWEI (column II), MSSER elastic modulus estimates were generally comparable. Although SWEI provided substantially more accurate elastic modulus estimates in Samples A and D, MSSER estimates were much more accurate in Sample C and were within 0.1 kPa of error for estimated elastic modulus for Sample B.

Equations and numerical results of the experimental configurations discussed herein are based on the approximation that MSSER imaging mimics unconfined, uniaxial mechanical testing. The agreement between MSSER elastic modulus values and mechanical testing values suggested that these assumptions are appropriate in the experimental context. Furthermore, the agreement between SWEI elastic modulus values and mechanical testing values suggested that SWEI can provide an accurate estimation for this mechanical parameter and supported the use of a combined SWEI and MSSER imaging technique.

Discrepancies between estimated MSSER elastic modulus values and measured elastic modulus values for Sample A can be attributed to larger amounts of decorrelation in displacement estimation. Signal decorrelation generally became more prevalent in the MSSER data with stiffer material and less force. To illustrate this claim, data in FIG. 7 present the mean correlation coefficients from the representative displacement profiles to the Voigt model for each gelatin phantom. As a result of larger amounts of signal decorrelation, the trend in data from FIG. 7 showed that the correlation coefficients decreased with increased elastic modulus and decreased force magnitude. Signal decorrelation was also evident in FIG. 8 where decorrelation resulted in larger amounts of spatial discontinuity in the mechanical parameters being imaged. The discontinuity was much more prevalent in parametric images from stiffer phantoms (row A and B) than parametric images for more compliant phantoms (row C and D).

Despite some signal decorrelation present in the data, trends in parametric images displayed in FIG. 8 agreed with expected results. In the first column, elastic modulus data from SWEI are presented. As anticipated, elastic modulus values decreased from Sample A to Sample D, which was consistent with mechanical testing results. In the second column, parametric images of force magnitude were presented. It was apparent from these images that for all samples, force magnitude was highest around the focus (20 mm) and decreased gradually with increased axial distance.

Furthermore, despite the apparent signal decorrelation that was present primarily in Sample A and Sample B, force magnitude appeared to be constant for all samples. This visual analysis was confirmed in FIG. 9B where average force magnitude was displayed for each gelatin sample. For each sample, the average force magnitude showed the expected trend of increasing force magnitude with increasing number of cycles per pushing pulse. Furthermore, for each gelatin sample, force magnitude at 12-cycle pushing pulse was roughly twice as large as force magnitude at 6-cycle pushing pulses.

The apparent increase in force magnitude for a given MSSER beam sequence for Samples A and B was likely the result of artifacts in the steady-state displacement values from signal decorrelation. Other trends visually apparent in FIG. 8 included increased spring constant values with increased elastic modulus, increased coefficient of viscosity with increased elastic modulus, and stable relaxation time constant values across all gelatin phantom samples. Again these trends are confirmed from the plots in FIG. 9. It is also apparent from FIGS. 9A, C, and D that standard deviation increased for the Voigt parameters with increased elastic modulus and decreased number of cycles per pushing pulse. These trends are in agreement with the trends from correlation coefficient data in FIG. 7.

Representative displacement profiles were depicted in FIG. 10 and described the response of pig tissue to radiation force excitation. The initial deflection at the first time point along with the immediate deflection following force cessation suggested that pig tissue was better characterized by the Standard Linear model. Although displacement data from MSSER were fit to the Standard Linear model rather than the Voigt model, the estimated elastic modulus values in Table III were calculated by the same methods as described for the gelatin phantoms. The same 0.4859 value for the correction coefficient C was used to compute the estimated elastic modulus from MSSER. As shown in Table III, the estimated elastic modulus from MSSER agreed well with the mechanically tested elastic modulus values and with SWEI. Although the estimated mean elastic modulus from MSSER was closer in value to the mean Enduratec measurement than the value obtained from SWEI, all elastic modulus values overlapped in standard deviation. The variance in elastic modulus values reported in Table III was much larger than the variance reported in Table II and was a result of the more inhomogeneous composition of the pig tissue structure. As shown in the B-mode image in FIG. 11A, there appeared to be thin fibrous structures that ran diagonally across homogeneous muscle tissue, which are located by arrows. These structures became more apparent in the conventional ARFI images in FIGS. 11B and C for peak displacement and time to 67% recovery. Using the parametric data from SWEI, it was possible to fit MSSER displacement data to the Standard Linear model, and Equations (9) and (14) were used to solve for all mechanical components of the model along with force magnitude. These parametric images in FIGS. 11D-I showed the same delineation of thin fibrous structures from the surrounding muscular tissue (arrows). As predicted, the values of force magnitude shown in FIG. 11D are much larger than the values depicted in the gelatin phantoms due to a much larger attenuation. Local areas of higher force magnitude [shown as bright areas in FIG. 11D] may be the result of focused acoustic radiation force at 20 mm and local areas of increased attenuation and/or decreased speed of sound. This area corresponded with the thin fibrous structure in other parametric images. With the exception of the parametric image for $\mu_0$ in FIG. 11G, images displaying other Standard Linear parameters showed additional delineation of tissue structure that was not apparent from conventional ARFI images.

The presently disclosed subject matter presents a fully quantitative method for acoustic radiation-force imaging by taking advantage of discrete viscoelastic models to exploit tissue mechanical properties. Previous works in this area of research have generally involved two different approaches to modeling the mechanical response of tissue to acoustic radiation force. Finite element models based on weak-form elastodynamics [30], [31], [37] have been employed to provide comprehensive models of tissue response in three dimensions. Although these models neglect force dissipation, they offer the primary advantage of taking shear wave propagation and the interconnection of tissue elements into account. By modeling force distribution in three dimensions, finite element models can account for the load placed on a volume of tissue rather than a single point of interest. Although the discrete models used herein explain the relaxation of tissue through viscoelastic creep, it is likely that there is an "apparent" relaxation of tissue due to finite propagation speeds of shear waves. Although discrete viscoelastic approaches neglect these effects, they offer readily realizable equations and computational efficiency, and they take into account the dissipation of force by offering a viscous component to the model.

Conclusions

The systems and methods presented herein attempt to solve fully for all parameters characterizing viscoelastic tissue response to acoustic radiation force. The beam sequences can mimic a materials creep test, which can be referred to as mechanical steady-state excitation and recovery imaging (MSSER). When applied force magnitude was known through experimental characterization of the imaging system, estimates of elastic modulus values were obtained from gelatin tissue phantoms and pig muscle. Results were in agreement with values obtained from mechanical testing of the samples, which supports the principle that the approximation of MSSER imaging as uniaxial mechanical compression is valid in the experimental context. With force magnitude considered unknown but elastic modulus data provided through SWEI, parametric images of mechanical parameters can be rendered. Results can generally be expected to improve with higher intensity pushing forces in more compliant tissue, higher tissue echogenicity, and more homogeneous tissue samples. Estimates of elastic modulus can be expected to suffer when MSSER imaging is singly applied to inhomogeneous tissue samples because it is unable to detect local changes in attenuation and speed of sound for force magnitude estimations.

However, when elastic modulus data are provided through a combined imaging approach with SWEI, quantitative results from MSSER can be expected to perform well in viscoelastic, echogenic tissue samples, independent of applied radiation force magnitude. From the results presented hereinabove, it is apparent that MSSER can provide valuable information about the mechanical properties of tissue that are not obtained in previously described radiation force imaging techniques.

Exemplary Hardware and Software Implementation

Figure 12:
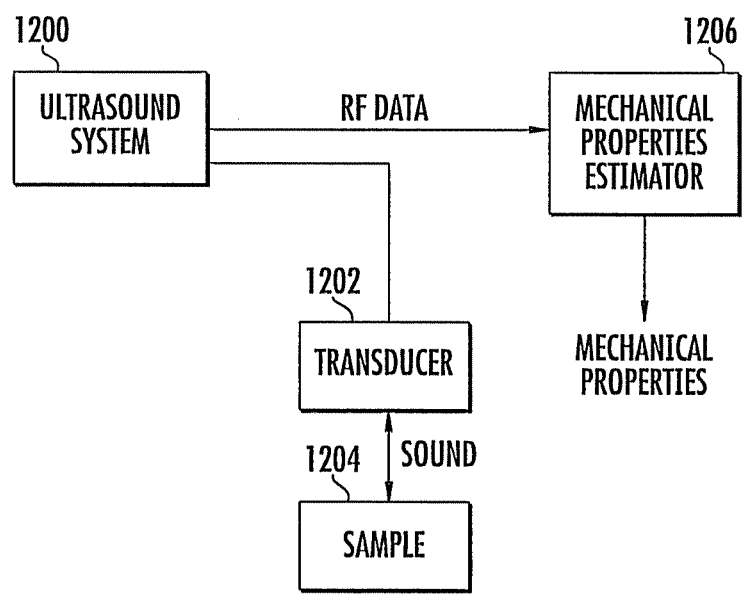
FIG. 12 is a block diagram of an exemplary system for determining mechanical properties of a sample according to an embodiment of the presently disclosed subject matter.

As stated above in the Methods section, the subject matter described herein can be implemented using a commercially available scanner equipped with a transducer and a computer programmed to perform the mechanical property parameter value estimations described herein. FIG. 12 is a block diagram of an exemplary system for determining mechanical properties of a sample according to an embodiment of the subject matter described herein. Referring to FIG. 12, the system includes an acoustic monitor 1200 and an acoustic transducer 1202 for applying acoustic energy to a sample 1204 to apply mechanical force to the sample and for measuring displacements of the sample resulting from the application of the acoustic energy and timings of the displacements. In one example, acoustic monitor 1200 and acoustic transducer 1202 can be implemented using the above-described ultrasound scanner and linear array transducer. Sample 1204 can be any material for which mechanical properties are desired to be determined, whose response to applied force can be modeled using a mechanical model, and whose displacement in response to the applied force can settle to an equilibrium value. For example, sample 1204 may be a biological tissue sample, such as a human tissue sample, or a non-biological sample, such as a textile material sample. In addition, although the term "sample" is used herein to describe the viscoelastic material being tested, this term is intended to include both in vivo and ex vivo biological materials.

In FIG. 12, the system further includes a mechanical properties estimator 1206 for using a mechanical model to model a mechanical response of the sample to applied force. The model may model a steady state response of the sample during application of the acoustic energy and a recovery response that occurs after cessation of the application of the acoustic energy. Mechanical properties estimator 1206 may determine quantitative values of mechanical property parameters of the model using the displacements and the timings of the displacements (illustrated as RF data in FIG. 12. For example, mechanical properties estimator 1206 may estimate the elastic modulus of sample 1204 using either of the techniques described above. Mechanical properties estimator 1206 may use the estimated elastic modulus and determine the applied force magnitude using Equations (9) and (14) described above. Mechanical properties estimator 1206 may then used the applied force magnitude and the monitored displacement values and timings to determine quantitative values for at least one or all of the mechanical property parameters in each of the models described above or in other models that model mechanical properties of a system.

In FIG. 12, mechanical properties estimator 1206 is shown as being separate from acoustic transducer 1202. However, the subject matter described herein is not limited to such an implementation. In an alternate implementation, mechanical properties estimator 1206 may be integrated within an acoustic scanner, such as an ultrasound scanner.

Figure 13:
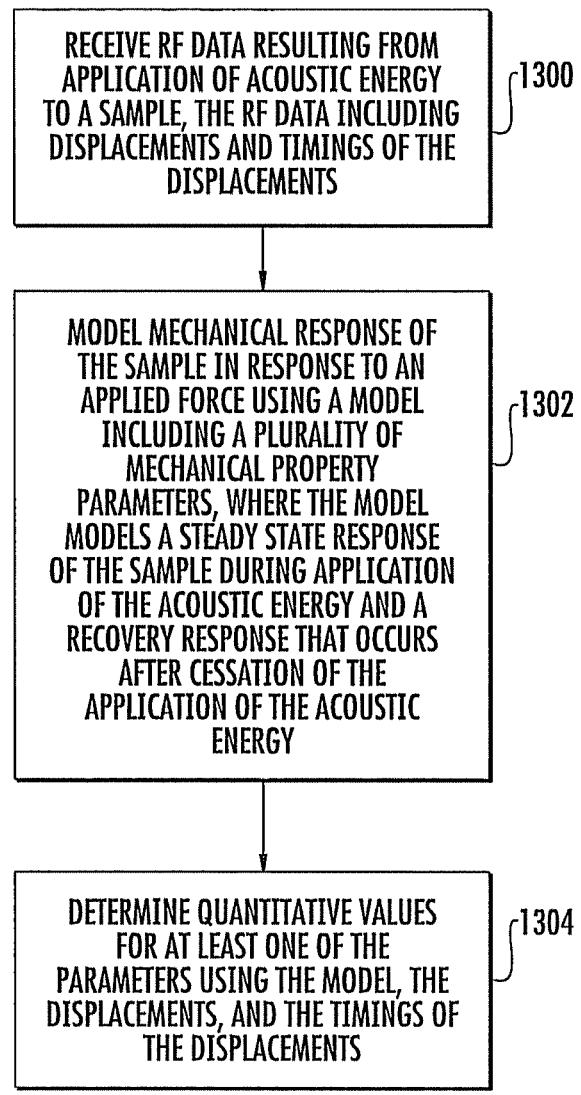
FIG. 13 is a flow chart illustrating an exemplary process for determining mechanical properties of a sample from radio frequency (RF) data resulting from application of acoustic energy to the sample according to an embodiment of the presently disclosed subject matter.

FIG. 13 is a flow chart illustrating an exemplary process that may be implemented by mechanical properties estimator 1206 to determine mechanical mechanical properties of a sample using received RF data according to an embodiment of the subject matter described herein. Referring to FIG. 13, in step 1300, radio frequency data resulting from application of acoustic energy to a sample is received. The radio frequency data includes displacements of the sample caused by the application of the acoustic energy and timings of the displacements. In step 1302, a mechanical response of the sample to applied force is modeled using a model including a plurality of mechanical property parameters, wherein the model models a steady state response of the sample during application of the acoustic energy and a recovery response that occurs after cessation of the application of the acoustic energy. For example, mechanical properties estimator 1206 may use any mechanical model, such as the Voigt or standard linear model described above, to model behavior of the system. In step 1304, a quantitative value is determined for at least one of the parameters using the model, the displacements, and the timings of the displacements. For example, mechanical properties estimator 1206 may estimate the elastic modulus of the sample using any of the techniques described above, calculate the applied force magnitude using Equations (9) and (14), and determine quantitative values for the parameters in the model using the applied force magnitude and the displacement and time values.

Applications

The subject matter described herein for determining mechanical properties of materials may be used for diagnostic medical applications, non-diagnostic basic science applications, and non-medical, non-basic-science applications. Examples of diagnostic medical applications include tissue differentiation based on differences in mechanical properties, monitoring disease progression or response to therapeutic treatment based on changes in mechanical properties of tissue over time in response to disease progression or therapeutic treatment, etc.

By way of specific example, MSSER imaging as described herein can be used to detect atherosclerotic plaques and describe their composition and structure. In this manner, MSSER can improve cardiovascular risk assessment and support proper administration of therapeutic interventions, including drug therapies and/or procedures. MSSER imaging can also be used to detect malignant tumors and distinguish them from benign lesions. MSSER is also relevant to describing tumor size, shape, structure, and composition, and the systems, methods, and computer readable media described herein can be implemented to monitor response to therapy or progression over time (i.e. changes in tumor size, shape, or composition). Similarly, MSSER imaging can be used to detect changes in liver tissue composition consistent with cirrhosis, cancer, or other diseases. In addition, MSSER imaging can be used to monitor transplant kidney status, predict causes of graft failure, and detect and characterize kidney disease in native kidneys. In yet another example, MSSER can be used to assess the mechanical properties of muscle in regard to monitoring musculoskeletal diseases such as Duchenne muscular dystrophy and to establishing the efficacy of treatments. MSSER can similarly be applied to monitor changes in muscular properties associated with physical or drug therapies, or to changes in the mechanical properties of tendons, ligaments, or bones. In still another example, MSSER imaging can be used to monitor ablation procedures in regard to defining the location and size of the ablated tissue region.

Further, an example of a non-diagnostic basic science application for which the subject matter described herein can be used is non-destructive testing of the mechanical properties of engineered tissue. For instance, MSSER imaging can be used to measure the mechanical properties of engineered tissues to assess the impact of various environmental factors, including chemical, thermal, electrical, magnetic, and mechanical environments. Engineered tissue can be formed by subjecting stem cells to environmental conditions that cause the stem cells to differentiate into bone cells, nerve cells, muscle cells, etc. Current techniques for testing the mechanical properties of engineered tissue samples are destructive, preventing successive tests involving the same sample and requiring destruction of multiple samples to determine mechanical properties of samples at different stages of tissue differentiation. Because the techniques described herein can determine the mechanical properties of tissue non-destructively, plural tests can be performed for the same sample to test the mechanical properties of that sample. As a result, the same engineered tissue sample can be repeatedly used to determine how the mechanical properties of engineered tissue change over time or in response to a sequence of different mechanical tests.

In another example, MSSER imaging can be implemented to assess the mechanical properties of excised tissue samples, both human and animal, for mechanical property assessment to delineate disease pathophysiology, natural history, response to therapy, etc. Again, because MSSER is a non-destructive approach, the same sample may be examined serially by MSSER imaging.

Examples of non-medical, non-basic-science samples that can be tested using the subject matter described herein include any materials for which it is desirable to non-destructively determine its mechanical properties. Specifically, for example, MSSER can be used to nondestructively test the mechanical properties of textiles, rubbers, polymers, and other non-biological materials.

As stated above, the subject matter described herein may be used to determine mechanical properties of viscoelastic and other types of materials, such as purely elastic materials whose mechanical behavior in response to applied mechanical force can be accurately modeled using a mechanical model that models a mechanical response of the material when excited by a forcing function and whose displacement can settle to an equilibrium value under application of the forcing function. In order to determine the mechanical properties of purely elastic materials, it would be necessary to model the mechanical behavior of such materials in response to applied mechanical force using a mathematical model. MSSER would then be used to apply mechanical force to the materials using acoustic energy. The resulting displacements and timings of the displacements would then be recorded. From the displacements and timings of the displacements, quantitative values for the parameters in the model could be determined.

For non-viscous elastic materials, an elastic model may be used. The term "elastic model" varies greatly across the literature. It can be as simple as a phenomenological experimental approach such as taking the instantaneous slope of the measured/applied force versus displacement response, and calling this slope a "modulus". At the other end of the spectrum, more elaborate finite element method (FEM) simulations are conducted on the domain with boundary conditions that model the specific experimental loading set-up. The resulting numerical simulations then generate a force-displacement curve that is curve-fit to the measured experimental force-displacement response, thus yielding the material's intrinsic elastic properties (e.g. Young's modulus, Poisson's ratio for linear isotropic elasticity) via optimization.

Of course, it is to be understood that the examples listed are but a small sampling of the many uses for the systems, methods, and computer readable media described herein. In this regard, the examples listed above are intended to be representative of the types of applications for the disclosed technology and not limiting.

Introduction to Non-Steady-State and Partial Recovery Techniques

Physicians have long used palpation as a simple diagnostic tool for detecting differences in the mechanical properties of tissue and identifying abnormalities. The mechanical properties of tissue vary widely among different physiological and pathological states [21] and thus have significant diagnostic potential. For instance, the relative hardness of malignant tumors is the basis for the use of palpation to detect breast cancer [39]. However, palpation is only applicable to superficial organs and pathologies and is subjective and limited to the touch sensitivity of the practitioner. In recent decades, significant effort has been directed towards producing techniques for non-invasive characterization of the mechanical properties of tissue. Elastography methods are generally based on inducing tissue deformation or displacement and detecting the response [1] [40].

As described above, one established ultrasonic method for noninvasively interrogating the mechanical properties of tissue is Acoustic Radiation Force (ARF) Impulse imaging. In ARF Impulse imaging a short duration, and relatively high intensity acoustic impulse is used to generate localized displacements in the region of excitation [27] [30]. An extensive body of literature documents the wide relevance of ARF based methods in clinical diagnostic imaging; however these applications have primarily focused on the elastic properties of tissue and have neglected tissue viscosity. The omission of viscosity can cause error in the estimation of tissue elasticity [41]; moreover, important information about the physiological state of the tissue may be lost [42].

Duchenne muscular dystrophy (DMD) is an X-linked recessive disorder in which the absence of the protein dystrophin from myofiber membranes causes progressive degeneration of skeletal and cardiac muscle. Muscle degeneration is accompanied by myofiber necrosis and subsequent progressive replacement of muscle by fibrous tissue and fat. Fibrous and fatty deposition, together with ongoing myofiber regeneration, can lead to initial muscle enlargement (hypertrophy), generally followed by severe and progressive loss of muscle mass (atrophy) and function. Recent biomechanical studies in livers have shown that fibrotic livers exhibit higher elasticity and viscosity that control livers in both humans and rats [42-44]. Livers with steatohepatitis (inflammation of the liver with concurrent fat accumulation) were also shown to exhibit higher elasticity and viscosity than the control, while in livers with steatosis (fat accumulation alone) elasticity was unchanged but viscosity was higher relative to control [44]. To the best of our knowledge, no similar testing has been completed in dystrophic muscles; however, we speculate that similar alterations in muscular viscoelastic properties will be associated with DMD. Because dystrophic muscle undergoes changes in viscoelasticity associated with fibrosis and fatty deposition, it is a relevant model for viscoelastic imaging.

Viscoelastic properties may be assessed by a variety of acoustic methods. Some approaches relate viscoelastic properties to shear wave propagation characteristics. In transient elastography an external vibrator is used to generate shear waves at several frequencies [45]. Tissue elasticity and viscosity can be reconstructed using an inversion algorithm. The use of an external vibrator in this technique limits its in vivo applications. Shearwave Dispersion Ultrasound Vibrometry (SDUV) extracts the shear modulus and viscosity by generating ARF-induced shear waves at multiple frequencies and measuring the frequency dispersion of the shear-wave propagation speed [46, 47]. This technique, however, requires the assumption of local homogeneity and provides only a single-point measurement. Another shearwave method termed supersonic shear imaging (SSI) applies an ultra-fast ultrasound scanner to generate a supersonic moving source as well as to image the resulting shear waves [26]. Supersonic shear imaging has the potential to quantitatively solve for both tissue elasticity and viscosity [26] and has been used to study the viscoelastic properties of breast lesions [48] and liver [49]. However, this technique requires super-fast imaging (with a frame rate up to 5000 frames per second), which is not compatible with current commercial ultrasound scanners. Additionally, because these techniques rely on shear wave propagation, they lack the ability to access the viscoelastic properties in the region of excitation.

Other approaches to viscoelastic property assessment apply sustained mechanical force to induce displacements and solve for elastic and viscous parameters using established viscoelastic models. In quasi static elastography, viscoelastic features can be recovered from time-varying strain [50]. A compression-hold-release stress stimulus can be used to form images of elastic strain and strain delay times. However, very long acquisition times (>100 s) are necessary to get this information, making the in vivo relevance limited. Kinetic Acoustic Vitreoretial Examination (KAVE)n and Monitored Steady-State Excitation and Recovery (MSSER) [51] both use successive ARF impulses to fully displace tissue and solve for viscoelastic properties by fitting experimental displacement to the Voigt and standard linear viscoelastic models, respectively. Because these methods require that tissue achieve steady-state displacement, KAVE and MSSER suffer from slow frame rate and/or tissue heating from the amplitude and duration of ARF excitations necessarily in physiologically relevant conditions.

This section describes novel beam sequences and signal processing approaches for interrogating the viscoelastic properties of tissue using Multi-Push Acoustic Radiation Force (MP ARF) imaging. These methods have been demonstrated in custom viscoelastic tissue mimicking materials as well as in canine muscle, in vivo, with validation by spatially matched immunohistochemistry. We hypothesize that Acoustic Radiation Force ultrasound can be exploited to describe the viscoelastic properties of tissue.

Theory

Figure 14C:
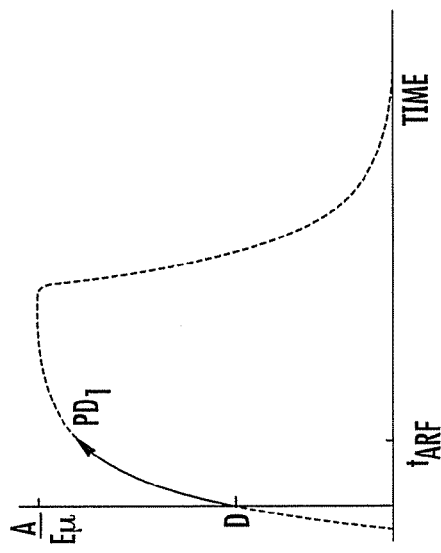
FIG. 14 illustrates graphs of displacement versus time in a viscoelastic material as described by the Voigt model immediately following the first ARL push (a), x milliseconds after the first ARF push (b), and immediately following the second ARF push (c)
Figure 14B:
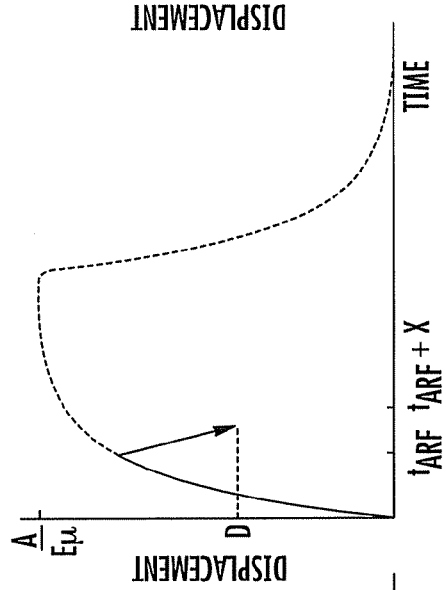
Figure 14A:
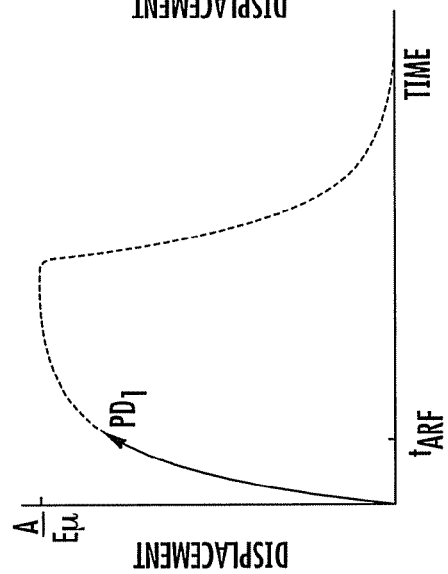

MP ARF uses displacements from two successive ARF excitation impulses to measure viscoelastic properties. We can calculate the marginal peak displacement (MPD) achieved by the second ARF push as (FIG. 14):

$$MPD = 1 - \frac{PD_2 - D}{PD_1} \quad (16)$$

where $PD_1$, is peak displacement (PD) achieved by the first push, $PD_2$ is the PD achieved by the second push, and D is the partial relaxation of the tissue from the first push at the time of the second push. Using MP ARF, tissues that recover nearly fully from the first excitation before the second excitation is administered will have a small D, and $PD_2$ will approximately equal PD1, yielding MPD≈1. This response is expected for normal muscle. Tissues with relatively low elasticity and high viscosity, such as fat, will have experienced little recovery by the time of the second push, yet still be far from steady state, resulting in a large difference between $PD_2$ and D relative to $PD_1$ and an MPD that is <1. In tissues with both relevantly high elasticity and high viscosity, such as in collagen-rich tissue like fibrotic tissue, will be at or nearing steady-state following the first push. Since this tissue will have experienced little recovery by the time of the second push, the difference between $PD_2$ and D will be small relative to $PD_1$, yielding a small MPD.

While MPD provides discrimination of viscoelastic tissue properties, it is not quantitative. By applying the Voigt or other suitable mechanical model, we can quantitatively describe the viscoelastic response of soft tissue to multi-push ARF. Considering our ARF excitation as a temporal unit step function of force magnitude A and duration $t_{ARF}$, tissue displacement in the direction of force is (FIG. 14(a)):

$$PD_1 = \frac{A}{E\mu}(1 - e^{-t_{ARF}/\tau_\sigma}) \quad (17)$$

$$PD_2 = \frac{A}{E\mu} - \left(\frac{A}{E\mu} - D\right)e^{-t_{ARF}/\tau_\sigma} \quad (18)$$

Subtracting $PD_1$ from $PD_2$ and solving for the relaxation time constant (RTC) for constant stress, $\tau_\sigma$, yields:

$$\tau_\sigma = \frac{-t_{ARF}}{\ln\left(\frac{PD_2 - PD_1}{D}\right)} \quad (19)$$

RTC provides a direct descriptor of the viscoelastic response of the material. Unlike MPD measurements and conventional acoustic radiation force impulse (ARFI) imaging, RTC measurements are independent of variations in the applied ARF magnitude.

Figure 15:
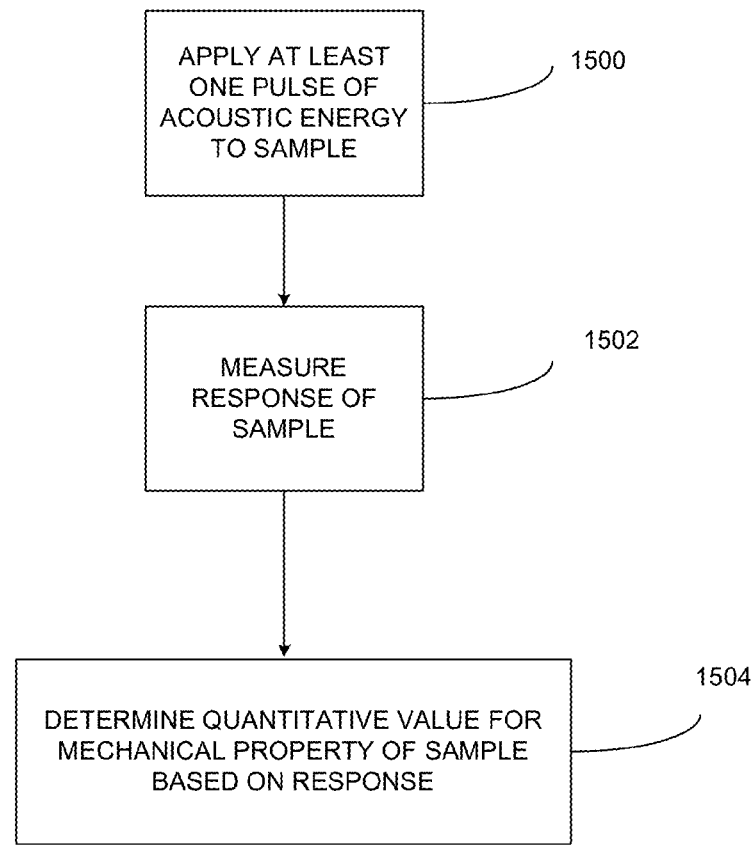
FIG. 15 is a flow chart illustrating an exemplary method for using multi-push ARF to characterize mechanical properties of tissue according to an embodiment of the presently disclosed subject matter.

FIG. 15 is a flow chart illustrating an exemplary method for using multi-push ARF to characterize mechanical properties of tissue. Referring to FIG. 15, in step 1500, a plurality of pulses of acoustic energy is applied to a sample. In one embodiment, successive pulses may be applied with a magnitude and duration such that the tissue is not driven to steady state displacement. Such application may be performed using ultrasound system 1200 and ultrasound transducer 1202 illustrated in FIG. 12. The sample may be a tissue sample or any other sample type, including those described herein, for which it may be desirable to quantitatively determine mechanical property values.

Returning to FIG. 15, in step 1502, a response of the sample is monitored while displacement is induced in the sample caused by the application of the mechanical force. In one example, a single transducer 1202 is used for both excitation and monitoring. The single transducer 1202 may apply acoustic energy to the sample, which results in displacement of the sample in the direction of applied force. Transducer 1202 may be switched to the monitor mode while the sample is being displaced in the direction of applied force caused by a first pulse of acoustic energy. A recovery response may also be monitored as the sample begins to recover by displacing itself in a direction opposite the direction of applied force when the application of acoustic energy by one pulse has ceased. The recovery response monitored may be a partial recovery that occurs between successive applications of acoustic energy. In an alternate example, monitoring of the recovery response may be omitted. Whether the recovery response is monitored or not, transducer 1202 may be used to apply a second pulse of acoustic energy, where the second pulse likewise does not induce steady state displacement in the sample. The response of the sample may be monitored by switching transducer 1202 to the monitor mode to monitor displacement of the sample while the sample is being displaced in the direction of the applied force.

In the preceding paragraph, a single transducer is used for acoustic energy application and response monitoring. In an alternate implementation, separate transducers may be used for acoustic energy application and response monitoring. For example, one transducer 1202 may be used to apply successive pulses of acoustic energy and another transducer 1202 may be used to monitor the displacement of the sample during the application of acoustic energy and also the recovery response between successive applications of acoustic energy.

Again referring to FIG. 15, in step 1504, a mechanical property of the sample is determined quantitatively based on the response. For example, if the recovery response is monitored, mechanical properties estimator 1206 may receive as input the non-steady state displacement versus time while the sample is being displaced in a direction of force caused by the application of each pulse of acoustic energy and the partial recovery of the sample versus time between successive force applications. In an alternate implementation, monitoring of the recovery response may be omitted and the input to mechanical properties estimator 1206 may be the displacement that occurs during the application of acoustic energy if separate force application and monitoring transducers are used or the displacement that occurs in the direction of applied force before recovery starts if a single force application and monitoring transducer is used. Mechanical properties estimator 1206 inputs the measurements of $PD_1$, D, and $PD_2$ into Equation 19 and solves for $\tau_\sigma$ if the Voigt model is used. If the standard linear model is used, peak displacements measured during successive non-steady-state displacements $PD_1$ and $PD_2$ for successive pulses and the partial relaxation D between the pulses can be used to calculate the relaxation time constant for constant stress and/or the relaxation time constant for constant strain. If the Maxwell model is used, the values for $PD_1$, $PD_2$, and D can be used to calculate the coefficient of viscosity and/or the elastic modulus.

According to another aspect of the subject matter described herein, the relaxation time constant for constant stress may be used to estimate the steady state displacement of the sample without pushing the sample to steady state during application of mechanical force. For example, mechanical properties estimator 1206 may use one of the mechanical models described herein to solve for $x_{ss}$, the steady state displacement of the sample, given the relaxation time constant for constant stress. For example, in the Voigt model where $x_{ss}$ is equal to $A/E\mu$, equation 17 can be rearranged to solve for $A/E\mu$ using $PD_1$ and $\tau\sigma$.

According to yet another aspect of the subject matter described herein, mechanical properties estimator 1206 may be used to estimate the shear wave velocity (SWV) using shear wave dispersion ultrasound vibrometry (SDUV), to calculate an elastic modulus of a sample. The elastic modulus can then be used to calculate the coefficient of viscosity from the relaxation time constant for constant stress calculated using multi-push, non-steady-state acoustic excitation and monitoring using Equation 4.

Results

All imaging was performed with a Siemens ACU SON Antares™ imaging system specially equipped for research purposes and a VF7-3 transducer (Siemens Medical Solutions USA, Inc. Ultrasound Division). Applicable procedures and protocols were in accordance with institutional guidelines and approved by the UNC-IACUC.

Five homogeneous, agar/gelatin tissue mimicking phantoms were prepared with different concentrations of gelation to vary elasticity and different concentrations of xanthan gum to alter viscosity [52]. A structured agar/gelatin phantom was also constructed with a background of high elasticity and low viscosity and a lesion of comparable elasticity and increased viscosity.

Tissue Mimicking Materials

TABLE 1

RTC measurements in tissue mimicking phantoms

| RTC (ms) | SDVU (ms) |
|---|---|
| 0.062 ± 0.019 | 0.068 ± 0.013 |
| 0.074 ± 0.018 | 0.074 ± 0.006 |
| 0.076 ± 0.032 | 0.076 ± 0.003 |
| 0.081 ± 0.028 | 0.088 ± 0.005 |
| 0.091 ± 0.015 | 0.121 ± 0.016 |

Figure 16:
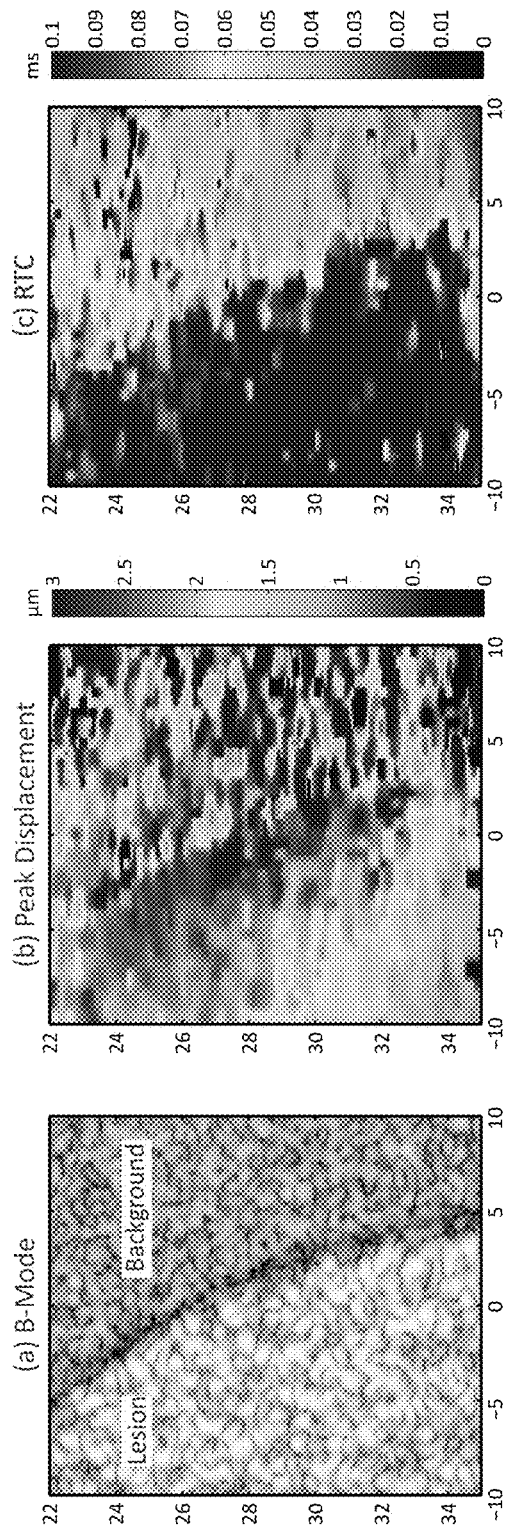
FIG. 16 illustrates images of B-Mode (a), peak displacement (b), and RTC images (c) of a structured phantom. The background (noted in panel (a)) was constructed with high elasticity and no viscosity. The lesion was constructed with high elasticity comparable to the background and high viscosity.

MP-ARF was implemented using two 300-cycle ARF excitations administered to the same region of excitation and separated by 0.8 ms in time. For each homogenous phantom RTC was calculated, and elasticity and viscosity were characterized using SDUV [53] and corroborated with Shear Wave Spectroscopy [54]. Average RTC values and the corresponding reference value calculated by SDUV are reported in Table 1. Results showed good agreement of RTC values calculated from MP-ARF with those calculated with SDUV and demonstrate the validity of the RTC calculations. The parametric image of RTC in the structured phantom (FIG. 16) discriminated the viscous lesion with a contrast-to-noise (CNR) of 1.2, whereas conventional ARFI peak displacement showed poor contrast of the lesion from the background with a CNR of 0.09.

Muscle, In Vivo

ARF imaging was performed in vivo on the rectus femoris (RF) and cranial sartorius (CS) muscles, in planes transverse and parallel to muscle fibers, of 3 golden retriever-whippet cross littermates with the following genotypes: (1) GRMD normal/myostatin normal (control), (2) GRMD/myostatin heterozygote null (Mstn+/−), and (3) GRMD/myostatin normal (Mstn+/+). Myostatin, a member of the TGF-β family, is a negative regulator of muscle growth. It has been proposed that reduction or elimination of myostatin could indirectly compensate for muscle degradation in DMD [55-57]. We focused our investigation on the RF and CS because these muscles undergo dramatically different responses to dystrophin deficiency. The RF undergoes early necrosis and fibrous deposition while the CS undergoes early true hypertrophy with an increase in contractile tissue [58]. Imaging results were correlated to MRI and morphometric data.

Figure 17:
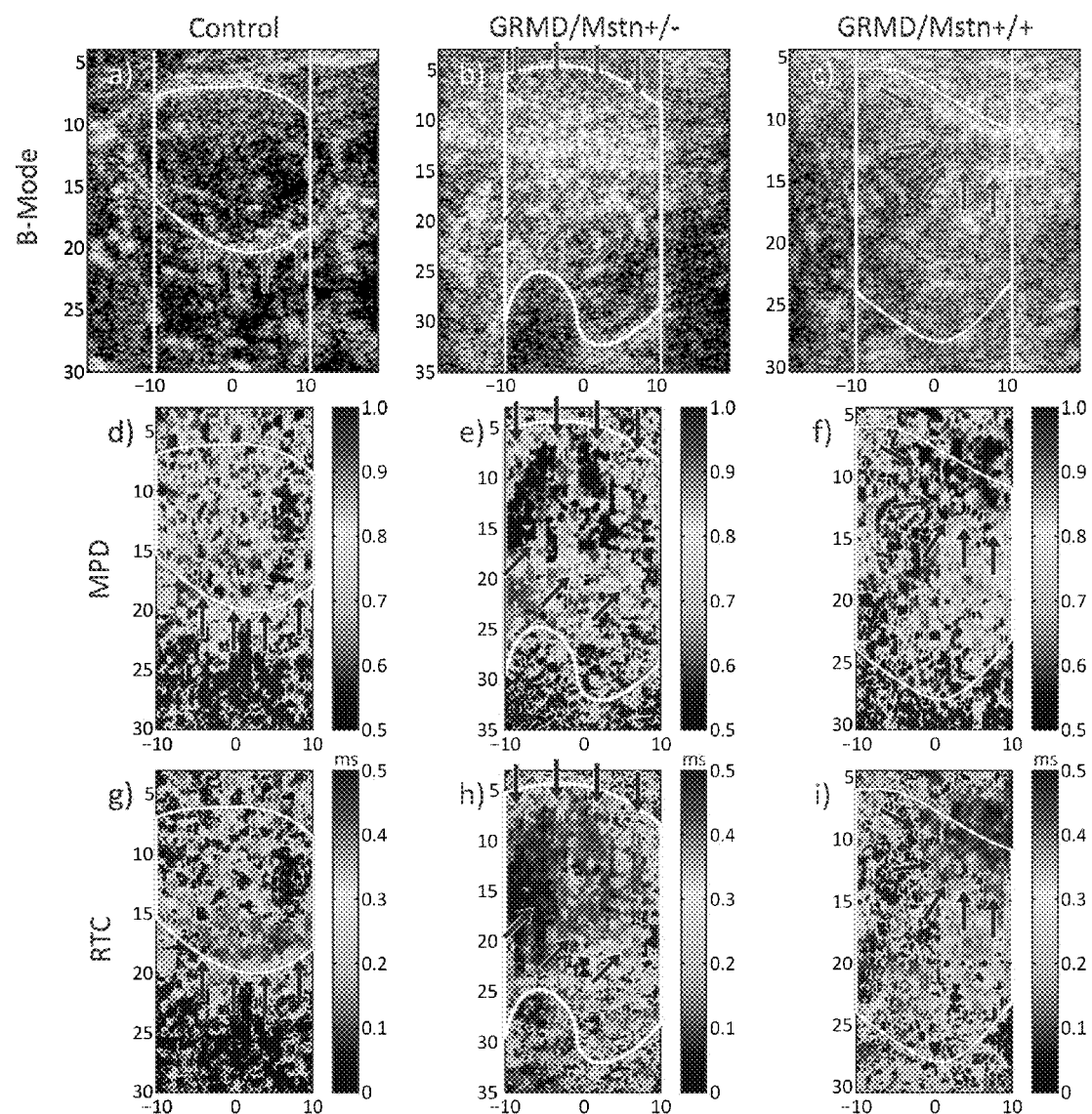
FIG. 17 illustrates images of B-Mode, MPD, and RTC in the transverse imaging plane for the RF muscle of a GRMD littermate triplet with myostatin variation.

Matched B-Mode (top row), MPD (middle row), and RTC (bottom row) images generated using MP ARF for the RF muscle in the transverse imaging plane in the 7 mo-old GRMD littermate triplet are shown in FIG. 17. The B-Mode image of the control RF (panel (a)) shows that the muscle generally exhibits relatively low echogenicity, with a small region of high echogenicity located at the base of the muscle, likely correspond to fascia (arrows). This region also exhibits low MPD and low RTC as shown in the corresponding MPD and RTC images (panels (d) and (g), arrows), which is consistent with higher stiffness. Higher stiffness is expected for fascia because it is mostly composed of collagen.

The B-Mode image of the GRMD/Mstn+/− dog qualitatively shows relatively high echogenicity and large scatterers in the upper two-thirds of the muscle (region inside the arrows). The corresponding region in the matched MPD and RTC images (panels (e) and (h)) exhibits low MPD and low RTC (black arrows), consistent with higher stiffness. This result suggests that the region is one of fibrous (rather than fatty) deposition. The B-Mode image of the GRMD/Mstn+/+ dog (panel (c)) shows an oblong structure with regions of relatively high echogenicity in the upper right portion of the muscle (arrows). The corresponding region exhibits low MPD (panel (f), arrows) and low RTC (panel (i)), consistent with high stiffness fibrous deposition. Comparable results were achieved in the parallel imaging plane, but the data is not shown for brevity. In the control RF 0.93% and 2.40% of values fell below an empirically calculated MPD threshold of 0.7, in the transverse and parallel planes respectively, while 8.76% and 12.80% of values in the GRMD/Mstn+/+ and 18.88% and 14.97% of values in the GRMD/Mstn+/− were below the threshold. These results suggest a larger proportion of stiffening in dystrophic RF with myostatin inhibition than without. Similar calculations have not yet been performed for RTC results.

Figure 18:
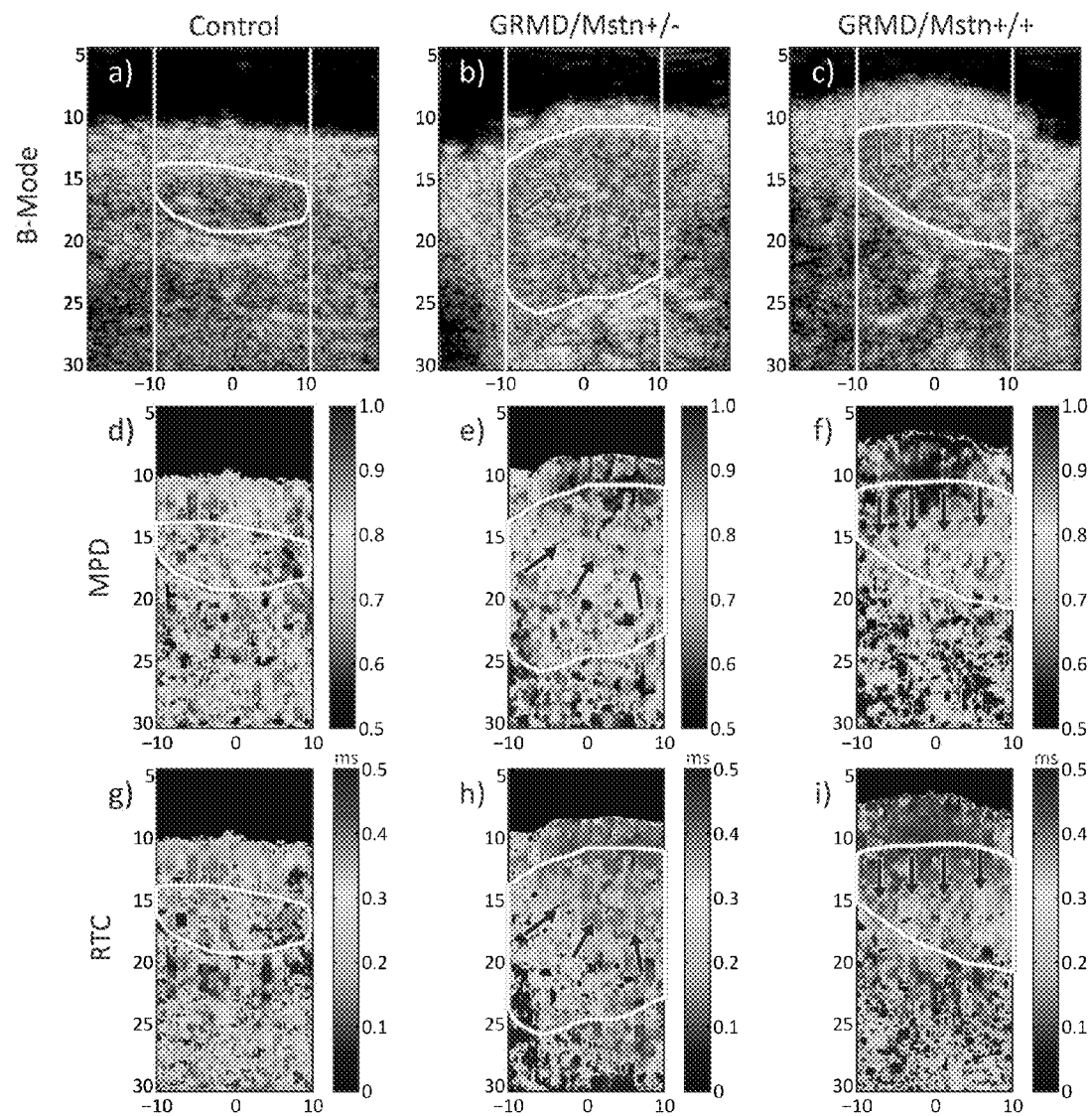
FIG. 18 illustrates matched B-Mode and MPD images in the transverse imaging plane for the CS muscle of a GRMD littermate triplet with myostatin variations.
Figure 19:
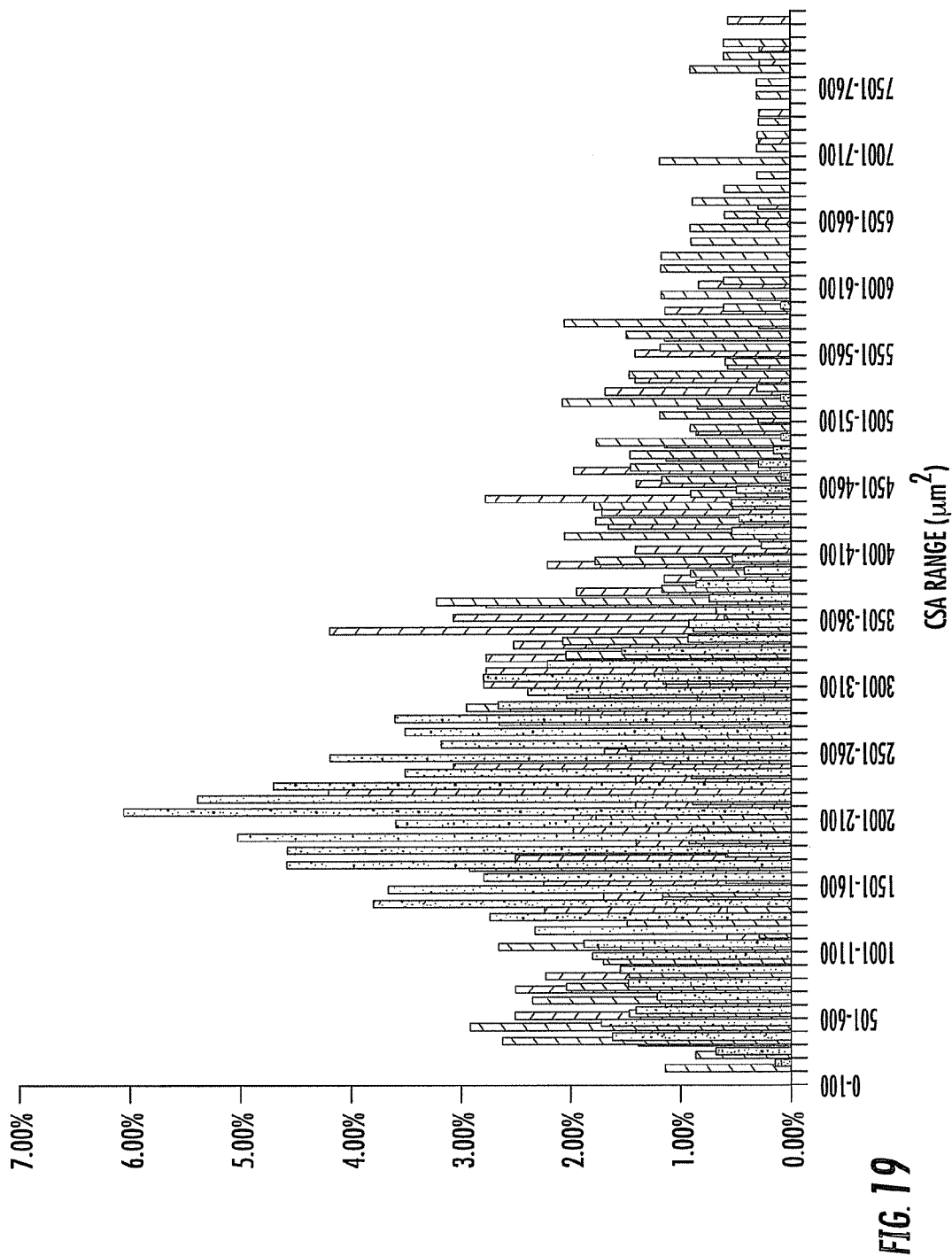
FIG. 19 is a histogram of myofiber CSA in the control (green), GRMD/Mstn+/+(blue) and GRMD/Mstn+/−CS.

FIG. 18 illustrates B-Mode (top row), MPD (middle row), and RTC (bottom row) images for the CS in the transverse imaging plane. The CS muscle is generally hypoechoic in the control B-Mode image (panel (a)), and the corresponding MPD and RTC images (panels (d) and (g)) have no notable structural features. The GRMD/Mstn+/− CS B-Mode image (panel (b)) does not show obvious differences in echogenicity, as was observes in the GRMD RF muscles, but a border to a structure is apparent (arrows). The corresponding images show both MPD (panel (e)) and RTC (panel (h)) values are relatively low within the structure (arrows), suggesting that it is stiffer than the surrounding CS muscle tissue. The fact that this region is not hyperechoic suggests that the increase in stiffness is not due to collagen deposition, per se, but perhaps due to variations in myofiber mechanical properties with hypertrophic muscle enlargement (see FIG. 19). Similarly, the GRMD/Mstn+/+ CS B-Mode image (panel (c)) does not include obvious areas of hyperechogenicity, but a structural border is discernible (arrows). The corresponding MPD in this area (panel (f), arrows) is low as is the corresponding RTC (panel (i)), suggesting increased tissue stiffness relative to the surrounding CS muscle. Once again, the fact that the low MPD region remains relatively hypoechoic suggests that the increase in muscle stiffness is not due to collagen deposition, but perhaps to myofiber mechanical property variation with hypertrophy. Comparable results were obtained by imaging the CS muscle in the parallel imaging plane, which are not shown for brevity. In the CS transverse and parallel imaging planes, 0.84% and 0.05% of values in the control, 10.78% and 4.43% in the GRMD/Mstn+/+, 2.12% and 3.45% of values in the GRMD/Mstn+/− were below the MPD threshold of 0.7. These results suggest a lower proportion of stiffening in dystrophic CS with myostatin inhibition than without. Similar calculations have not yet been performed for RTC results.

Table 2 summarizes the signal intensity and percent fat of RF, CS, VL and ST muscles in T2 FS and fat percentage images, respectively, for the littermate triplet at 7 mos.

TABLE 2

MRI Fat Saturated (FS) Signal Intensity and Fat % of RF and CS Muscles in the Littermate Triplet

|    | Control | | GRMD/Mstn+/− | | GRMD/Mstn+/+ | |
| --- | --- | --- | --- | --- | --- | --- |
|    | FS Signal Intensity | Fat % | FS Signal Intensity | Fat % | FS Signal Intensity | Fat % |
| RF | 147.61 ± 53.70 | 9.64 ± 5.96 | 312.41 ± 81.53 | 10.21 ± 7.61 | 186.79 ± 91.05 | 6.51 ± 4.93 |
| CS | 127.95 ± 34.86 | 14.51 ± 11.38 | 199.21 ± 87.86 | 10.03 ± 6.79 | 157.75 ± 50.05 | 8.86 ± 6.87 |

Given that the fat signal has been saturated in FS images, signal intensity should be due largely to fluid, presumably reflecting edema/inflammation associated with muscle necrosis. Note that fibrous deposition is not directly measured. Although the reported MRI results are an average over the entire muscle while DP ARF results represent a single 2D cross-sectional plane, the MRI results are generally consistent with our MPD results. In the RF (bolded), 44% and 35% higher FS signal intensity in the GRMD/Mstn+/− and GRMD/Mstn+/+ versus control, respectively, coupled with comparable (GRMD/Mstn+/−) or 62% lower (GRMD/Mstn+/+) fat % suggests fibrous rather than fatty deposition. Recall that the RF MPD images showed large areas of high MPD, consistent with predominantly fibrous deposition. In the CS (bolded), FS signal intensity was comparable in the control and GRMD/Mstn+/+ and 27% higher in the GRMD/Mstn+/−. Coupled with 48% and 33% lower fat % in the GRMD/Mstn+/− and GRMD/Mstn+/+ versus control, respectively, this suggests that CS hypertrophy is not due to fat, consistent with MPD results.

Muscle biopsies were taken from the CS, vastus lateralis (VL), long digital extensor, and lateral head of the gatrocnemius muscles of the triplet at age 7 months. The dystrophic dogs had histological features previously described in the GRMD (data not shown), with increased variability in fiber size, degenerating and regenerating fibers and endomysial fibrosis. Muscles from dystrophic dogs with or without myostatin mutation had similar histologic features, but the GRMD/Mstn+/− had slightly larger myofiber cross section area (CSA) in all four muscles. A CSA histogram for the CS muscle (FIG. 19) shows that the dystrophic dogs (diagonal hatching) had larger myofiber CSA than control, with the largest myofiber CSA in the GRMD/Mstn+/− (data generated by Kathryn Wagner, Johns Hopkins). This result is consistent with hypoechoic areas of lower MPD observed in the CS muscle of dystrophic dogs, which suggests that larger myofibers may impact CS mechanical properties.

MP ARF imaging was also performed in the ST muscle of a normal dog. The imaging plane was marked with a methylene blue injection and the corresponding cross-section was removed following necropsy. FIG. 6 shows the B-Mode image, spatially matched gross anatomy, RTC image, and histology. The RTC image (panel (e)) shows an area with high RTC (circled) suggesting low elasticity or high viscosity. The oil red o stained section (panel (j)) indicates that this area corresponds to a fat deposit; which supports high RTC. The RTC images also shows alignment of echogenic structures with lower RTC indicating high elasticity or low viscosity. The Masson's trichrome stained section (panel (i)) shows that highlighted tissue structures are composed of collagen; which supports lower RTC values.

Figure 20:
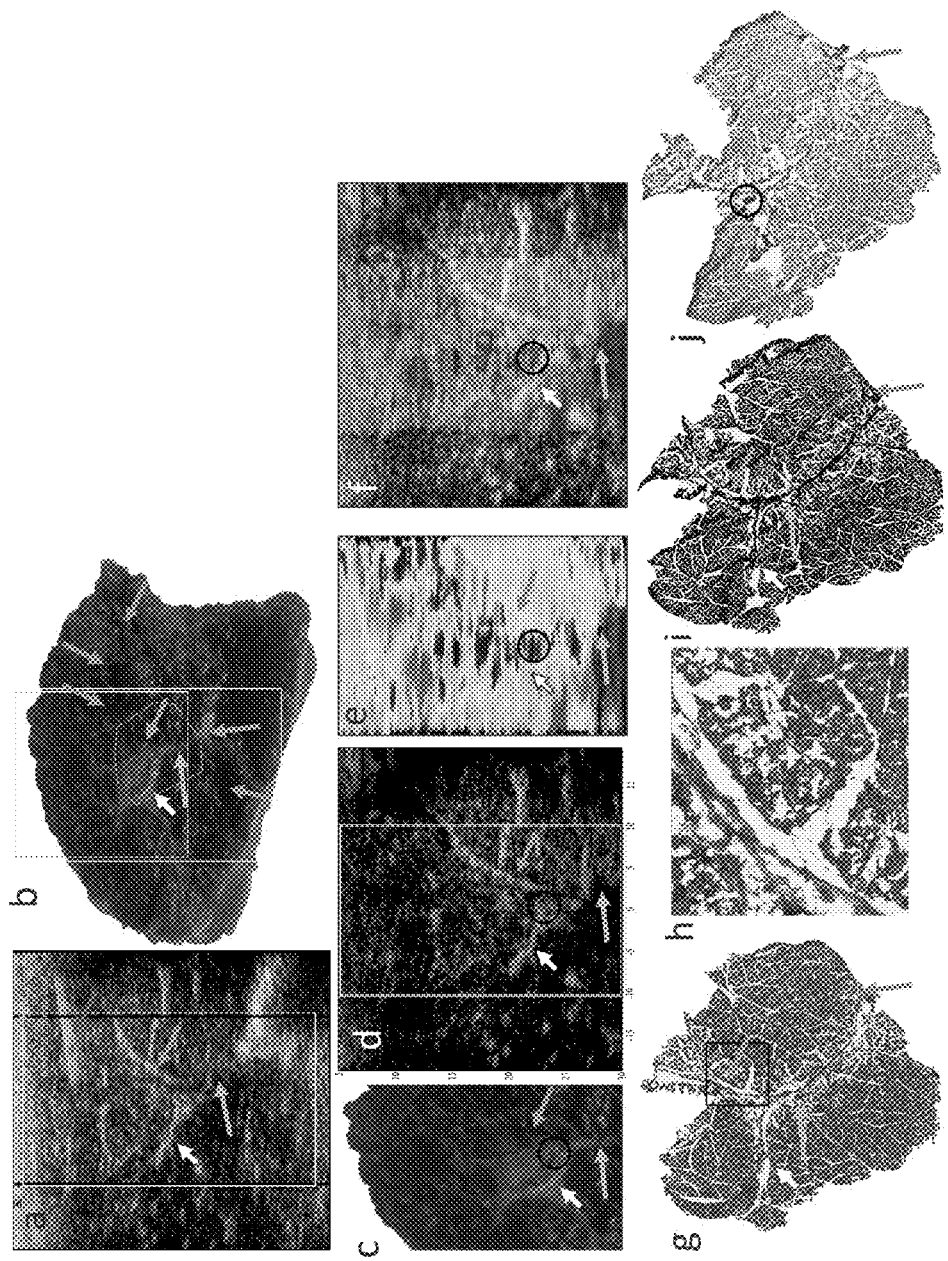
FIG. 20 illustrates alignment of B-Mode, gross anatomy, RTC, and histology images in control dog ST.

FIG. 20 illustrates images of alignment of B-Mode, gross anatomy, RTC, and histology images in control dog ST. Panel (a) in FIG. 20 is a screen-grab of a B-Mode image with echogenic tissue structures and injection needle highlighted by arrows. Panel (b) in FIG. 20 illustrates a gross image of an ST cross-section aligned to a B-Mode image with tissue structures appearing in the B-Mode image highlighted and macroscopically visible methylene blue stain (gray arrows). The MP ARF imaging (box) and histological (polygon) fields of view. Panel (c) in FIG. 20 illustrates a gross image zoomed to the MP ARF imaging field of view. Panel (d) in FIG. 20 illustrates the B-Mode imagery reconstructed from MP ARF data, with MP ARF field of view (lines) and tissue structures highlighted (arrows). Panel (e) in FIG. 20 illustrates the corresponding RTC image. Panel (f) in FIG. 20 illustrates a B-Mode with transparent RTC. Panels (g) through (j) in FIG. 20 illustrate matched histochemistry of H&E (g) with higher magnification to show methylene blue (h), Masson's trichrome (i) and oil red o (j).

CONCLUSIONS

We have introduced MP ARF, a new noninvasive ultrasound method for qualitatively (MPD) and quantitatively (RTC) evaluating the mechanical properties of tissue in viscoelastic tissue mimicking materials and in muscle in vivo. RTC results in tissue mimicking materials were in agreement with values obtained from SDUV, which suggested that our model was valid in our experimental context. Our in vivo preliminary results indicate that MP ARF differentiates focal regions of low MPD and low RTC consistent with fibrous deposits, edema/inflammation, and/or disordered muscle regeneration in the RF and CS muscles of dystrophic GRippet dogs with and without myostatin inhibition. MP ARF results were corroborated by MRI and histological processing. These preliminary data substantiate further investigation of MP ARF in dystrophic muscles and other viscoelastic tissue imaging applications.

REFERENCES

The disclosure of each of the references listed below is hereby incorporated herein by reference in its entirety.
1. J. F. Greenleaf, M. Fatemi, and M. Insana, "Selected methods for imaging elastic properties of biological tissues," *Annu. Rev. Biomed. Eng.*, vol. 5, pp. 57-78, 2003.
2. A. Samani and D. Plewes, "An inverse problem solution for measuring the elastic modulus of intact ex vivo breast tissue tumours," *Phys. Med. Biol.*, vol. 52, no. 5, pp. 1247-1260, 2007.
3. M. Bilgen and M. F. Insana, "Elastostatics of a spherical inclusion in homogeneous biological media."*Phys. Med. Biol.*, vol. 43, no. 1, pp. 1467-1473, 2002.
4. T. Varghese, J. Zagzebski, and F. Lee, "Elastographic imaging of thermal lesions in the liver in vivo following radiofrequency ablation: Preliminary results," *Ultrasound Med. Biol.*, vol. 28, pp. 1467-1473, 2002.
5. M. Sridhar, J. Liu, and M. F. Insana, "Viscoelasticity imaging using ultrasound: Parameters and error analysis," *Phys. Med. Biol.*, vol. 52, pp. 2425-2443, 2007.
6. J. Ophir, S. K. Alam, B. Garra, F. Kallel, E. Konofagou, T. Krouskop, and T. Varghese, "Elastography: Ultrasonic estimation and imaging of the elastic properties of tissue," in *Proc. Inst. Mech. Eng. [H]*, vol. 213, 1999, pp. 203-233.
7. D. Fu, S. Levinson, S. Gracewski, and K. Parker, "Noninvasive quantitative reconstruction of tissue elasticity using an iterative forward approach," *Phys. Med. Biol.*, vol. 45, no. 6, pp. 1495-1509, 2000.
8. D. Plewes, J. Bishop, A. Samani, and J. Sciarretta, "Visualization and quantification of breast cancer biomechanical properties with magnetic resonance elastography," *Phys. Med. Biol.*, vol. 45, no. 1, pp. 1591-1610, 2000.
9. R. Sinkus, J. Lorenzen, D. Schrader, M. Lorenzen, M. Dargatz, and D. Holz, "High-resolution tensor MR elastography for breast tumor detection," *Phys. Med. Biol.*, vol. 45, no. 6, pp. 1649-1664, 2000.
10. D. Steele, T. Chenevert, A. Skovoroda, and S. Emelianov, "Three-dimensional static displacement, stimulated echo NMR elasticity imaging," *Phys. Med. Biol.*, vol. 45, no. 1, pp. 1633-1648, 2000.
11. S. Park, S. R. Aglyamov, W. G. Scott, and S. Y. Emelianov, "Strain imaging using conventional and ultrafast ultrasound imaging: Numerical analysis," *IEEE Trans. Ultrason., Ferroelect., Freq. Contr.*, vol. 54, no. 5, pp. 987-995, 2007.
12. L. Taylor, B. Porter, D. Rubens, and K. Parker, "Three-dimensional sonoelastography: Principles and practices," *Phys. Med. Biol.*, vol. 45, pp. 1477-1494, 2000.
13. E. W. Van Houten, J. B. Weaver, M. I. Miga, F. E. Kennedy, and K. D. Paulsen, "Elasticity reconstruction from experimental MR displacement data: Initial experience with an overlapping subzone finite element inversion process," *Med. Phys.*, vol. 27, no. 1, pp. 101-107, 2000.
14. T. E. Oliphant, A. Manduca, R. L. Ehman, and J. F. Greenleaf, "Complex-valued stiffness reconstruction from magnetic resonance elastography by algebraic inversion of the differential equation," *Magn. Reson. Med.*, vol. 45, pp. 299-310, 2001.
15. A. L. McKnight, J. L. Kugel, P. J. Rossman, A. Manduca, L. C. Hartmann, and R. L. Ehman, "MR elastography of breast cancer: Preliminary results,"*AJR Am. J. Roentgenol.*, vol. 178, no. 6, pp. 1411-1417, 2002.
16. T. J. Hall, Y. N. Zhu, and C. S. Spalding, "In vivo real-time freehand palpation imaging," *Ultrasound Med. Biol.*, vol. 29, no. 3, pp. 427-435, 2003.
17. R. A. Baldewsing, F. Mastik, J. A. Schaar, P. W. Serruys, and A. F. W. van der Steen, "Young's modulus reconstruction of vulnerable atherosclerotic plaque components using deformable curves," *Ultrasound Med. Biol.*, vol. 32, no. 2, pp. 201-210, 2006.
18. R. A. Baldewsing, J. A. Schaar, F. Mastik, and A. F. van der Steen, "Local elasticity imaging of vulnerable atherosclerotic coronary plaques," *Adv. Cardiol.*, vol. 44, pp. 35-61, 2007.
19. R. L. Maurice, M. Daronat, J. Ohayon, E. Stoyanova, F. S. Foster, and G. Cloutier, "Non-invasive high-frequency vascular ultrasound elastography," *Phys. Med. Biol.*, vol. 50, pp. 1611-1628, 2005.
20. M. Fatemi and J. Greenleaf, "Ultrasound-stimulated vibroacoustic spectrography," *Science*, vol. 280, pp. 82-85, 1998.
21. A. Sarvazyan, O. Rudenko, S. Swanson, J. Fowlkes, and S. Emelianov, "Shear wave elasticity imaging: A new ultrasonic technology of medical diagnostics," *Ultrasound Med. Biol.*, vol. 24, no. 9, pp. 1419-1435, 1998.
22. W. F. Walker, F. J. Fernandez, and L. A. Negron, "A method of imaging viscoelastic parameters with acoustic radiation force," *Phys. Med. Biol.*, vol. 45, no. 6, pp. 1437-1447, 2000.
23. F. Viola and W. F. Walker, "Radiation force imaging of viscoelastic properties with reduced artifacts," *IEEE Trans. Ultrason., Ferroelect., Freq. Contr.*, vol. 50, no. 6, pp. 736-742, 2003.
24. E. Konofagou, J. Thierman, and K. Hynynen, "A focused ultrasound method for simultaneous diagnostic and therapeutic applications—A simulation study," *Phys. Med. Biol.*, vol. 46, no. 11, pp. 2967-2984, 2001.
25. K. Nightingale, R. Bentley, and G. E. Trahey, "Observations of tissue response to acoustic radiation force: Opportunities for imaging," *Ultrason. Imag.*, vol. 24, pp. 100-108, 2002.
26. J. Bercoff, M. Tanter, and M. Fink, "Supersonic shear imaging: A new technique for soft tissue elasticity mapping," *IEEE Trans. Ultrason., Ferroelect., Freq. Contr.*, vol. 51, no. 4, pp. 396-409, 2004.
27. K. Nightingale, M. Soo, R. Nightingale, and G. Trahey, "Acoustic radiation force impulse imaging: In vivo demonstration of clinical feasibility," *Ultrasound Med. Biol.*, vol. 28, no. 2, pp. 227-235, 2002.
28. K. Nightingale, S. McAleavey, and G. Trahey, "Shear wave generation using acoustic radiation force: In vivo and ex vivo results,"*Ultrasound Med. Biol.*, vol. 29, no. 12, pp. 1715-1723, 2003.
29. G. E. Trahey, M. L. Palmeri, R. C. Bentley, and K. R. Nightingale, "Acoustic radiation force impulse imaging of the mechanical properties of arteries: In vivo and ex vivo results," *Ultrasound Med. Biol.*, vol. 30, no. 9, pp. 1163-1171, 2004.
30. M. L. Palmeri, S. A. McAleavey, K. L. Fong, G. E. Trahey, and K. R. Nightingale, "Dynamic mechanical response of elastic spherical inclusions to impulsive acoustic radiation force excitation," *IEEE Trans. Ultrason., Ferroelect., Freq. Contr.*, vol. 53, no. 11, pp. 2065-2079, 2006.
31. M. L. Palmeri, A. C. Sharma, R. R. Bouchard, R. W. Nightingale, and K. R. Nightingale, "A finite-element method model of soft tissue response to impulsive acoustic radiation force," *IEEE Trans. Ultrason., Ferroelect., Freq. Contr.*, vol. 52, no. 10, pp. 1699-1712, 2005.
32. K. R. Nightingale, L. Zhai, J. J. Dahl, K. D. Frinkley, and M. L. Palmeri, "Shear wave velocity estimation using acoustic radiation force impulsive excitation in liver in vivo," in *Proc. IEEE Ultrason. Symp.*, vol. 1, 2006, pp. 1156-1160.
33. Y. C. Fung, *Biomechanics: Mechanical Properties of Living Tissues*. 2nd ed. New York: Springer, 1993.
34. W. Nyborg, "Acoustic streaming," in *Physical Acoustics*. vol. IIB, W. Mason, Ed. New York: Academic, 1965, ch. 11, pp. 265-331.
35. E. L. Madsen, J. A. Zagzebski, R. A. Banjavie, and R. E. Jutila, "Tissue mimicking materials for ultrasound phantoms," *Med. Phys.*, vol. 5, no. 5, pp. 391-394, 1978.
36. M. F. Insana, J. A. Zagzebski, and E. L. Madsen, "Acoustic backscattering from ultrasonically tissuelike media," *Med. Phys.*, vol. 9, no. 6, pp. 848-855, 1982.
37. M. L. Palmeri, S. A. McAleavey, G. E. Trahey, and K. R. Nightingale, "Ultrasonic tracking of acoustic radiation force-induced displacements in homogeneous media," *IEEE Trans. Ultrason., Ferroelect., Freq. Contr.*, vol. 53, no. 7, pp. 1300-1313, 2006.
38. "Exposure criteria for medical diagnostic ultrasound: II. Criteria based on all known mechanisms," National Council on Radiation Protection and Measurements, Bethesda, Md., NCRP Publications, Report No. 140, 2002.
39. Barton M B, Harris R, and Fletcher S W, "The rational clinical examination. Does this patient have breast cancer? The screening clinical breast examination: Should it be done? How?," JAMA: the Journal of the American Medical Association 282, 1270-1280 (1999).
40. Goo L. Parker K J, Lerner R M, et al., "Imaging of the elastic properties of tissue—a review," Ultrasound in medicine & biology 22, 959-977 (1996).
41. Bercoff J, Tanter M, Muller M, et al., "The role of viscosity in the impulse diffraction field of elastic waves induced by the acoustic radiation force," IEEE transactions on ultrasonics, ferroelectrics, and frequency control 51, 1523-1536 (2004).
42. Huwart L. Peeters F. Sinkus R, et al., "Liver fibrosis: Non-invasive assessment with mr elastography," NMR in biomedicine 19, 173-179 (2006).
43. Asbach P. Klatt D. Hamhaber U. et al., "Assessment of liver viscoelasticity using multifrequency mr elastography," Magnetic resonance in medicine: official journal of the Society of Magnetic Resonance in Medicine/Society of Magnetic Resonance in Medicine 60, 373-379 (2008).
44. Salameh N, Larrat B, Abarca-Quinones J, et al., "Early detection of steatohepatitis in fatty rat liver by using mr elastography," Radiology 253, 90-97 (2009).
45. Catheline S, Gennisson J L, Delon G, et al., "Measurement of viscoelastic properties of homogeneous soft solid using transient elastography: An inverse problem approach," J Acoust Soc Am 116, 3734-3741 (2004).
46. Chen S G, Fatemi M, and Greenleaf J F., "Quantifying elasticity and viscosity from measurement of shear wave speed dispersion," J Acoust Soc Am 115, 2781-2785 (2004).
47. Chen S, Urban M W, Pislaru C, et al., "Shearwave dispersion ultrasound vibrometry (sduv) for measuring tissue elasticity and viscosity," IEEE transactions on ultrasonics, ferroelectrics, and frequency control 56, 55-82 (2009).
48. Tanter M, Bercoff J, Athanasiou A, et al., "Quantitative assessment of breast lesion viscoelasticity: Initial clinical results using supersonic shear imaging," Ultrasound in medicine & biology 34, 1373-1386 (2008).
49. Muller M, Gennisson J L, Deffieux T, et al., "Quantitative viscoelasticity mapping of human liver using supersonic shear imaging: Preliminary in vivo feasability study," Ultrasound in Medicine and Biology 35, 219-229 (2009).
50. Insana M F, Pellot-Barakat C, Sridhar M, et al., "Viscoelastic imaging of breast tumor microenvironment with ultrasound," J Mammary Gland Biol 9, 393-404 (2004).
51. Mauldin F W, Jr., Haider M A, Loboa E G, et al., "Monitored steady-state excitation and recovery (msser) radiation force imaging using viscoelastic models," IEEE transactions on ultrasonics, ferroelectrics, and frequency control 55, 1597-1610 (2008).
52. Vappou J. Maleke C, and Konofagou E E., "Quantitative viscoelastic parameters measured by harmonic motion imaging," Phys Med Biol 54, 3579-3594 (2009).
53. Mitri F G, Urban M W, Fatemi M, et al., "Shear wave dispersion ultrasonic vibrometry for measuring prostate shear stiffness and viscosity: An in vitro pilot study," IEEE transactions on bio-medical engineering 58, 235-242 (2011).
54. Deffieux T, Montaldo G, Tanter M, et al., "Shear wave spectroscopy for in vivo quantification of human soft tissues visco-elasticity," IEEE Trans Med Imaging 28, 313-322 (2009).
55. Wagner K R, Fleckenstein J L, Amato A A, et al., "A phase i/iitrial of myo-029 in adult subjects with muscular dystrophy," Annals of neurology 63, 561-571 (2008).
56. Mendias C L, Bakhurin K I, and Faulkner J A., "Tendons of myostatin-deficient mice are small, brittle, and hypocellular," Proceedings of the National Academy of Sciences of the United States of America 105, 388-393 (2008).
57. Hoffman E P and Escolar D., "Translating mighty mice into neuromuscular therapeutics: Is bigger muscle better?," The American journal of pathology 168, 1775-1778 (2006).
58. Kornegay J N, Cundiff D D, Bogan D J, et al., "The cranial sartorius muscle undergoes true hypertrophy in dogs with golden retriever muscular dystrophy," Neuromuscular disorders: NMD 13, 493-500 (2003).

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter.

What is claimed is:
1. A method for determining a quantitative value for a mechanical property of a sample, the method comprising:
    applying a plurality of pulses of acoustic energy to a sample to apply a mechanical force to the sample and induce a non-steady-state displacement in the sample;
    monitoring a response of the sample caused by the application of the mechanical force; and
    determining a quantitative value for a mechanical property of the sample based on the response.
2. The method of claim 1 wherein applying a plurality of pulses of acoustic energy includes applying first and second successive pulses of acoustic energy to the sample.

3. The method of claim 2 wherein monitoring a response of the sample includes monitoring a response of the sample while the sample is being displaced in a direction of the application of the mechanical force and monitoring a displacement in a direction opposite the direction of the application of the mechanical force caused by recovery of the sample after application of the first pulse and before application of the mechanical force by the second pulse.

4. The method of claim 3 wherein applying the first and second successive pulses includes spacing the first and second successive pulses in time such that only partial recovery of the sample is achieved after application of the first pulse and before application of the second pulse.

5. The method of claim 1 wherein applying a plurality of pulses includes applying the pulses using a first transducer and wherein monitoring the response includes monitoring the response using a second transducer separate from the first transducer.

6. The method of claim 1 wherein applying a plurality of pulses includes applying the pulses using the same transducer used to measure the response.

7. The method of claim 1 wherein determining a quantitative value for a mechanical property parameter includes determining the quantitative value using a mechanical model for viscoelasticity.

8. The method of claim 7 wherein the mechanical model comprises the Voigt model, the standard linear model or the Maxwell model.

9. The method of claim 1 wherein the mechanical property comprises at least one relaxation time constant.

10. The method of claim 9 comprising determining a steady state displacement of the sample from the at least one relaxation time constant and an observed displacement from at least one excitation.

11. The method of claim 1 wherein the mechanical property comprises a coefficient of viscosity or an elastic modulus.

12. A system for determining a quantitative value for a mechanical property of a sample, the system comprising:
 at least one acoustic transducer for applying a plurality of pulses of acoustic energy to a sample to apply a mechanical force to the sample and induce a non-steady-state displacement in the sample and for monitoring a response of the sample caused by the application of the mechanical force; and
 a mechanical properties estimator for determining a quantitative value for a mechanical property of the sample based on the response.

13. The system of claim 12 wherein the at least one acoustic transducer is configured to apply first and second successive pulses of acoustic energy to the sample.

14. The system of claim 13 wherein the at least one acoustic transducer is configured to monitor a response of the sample while the sample is being displaced in a direction of the mechanical force and to monitor a displacement in a direction opposite the direction of the mechanical force caused by recovery of the sample after application of the first pulse and before application of the second pulse.

15. The system of claim 14 wherein the at least one acoustic transducer is configured to space the first and second successive pulses in time such that only partial recovery of the sample is achieved after application of the first pulse and before application of the second pulse.

16. The system of claim 15 wherein the at least one acoustic transducer is configured to monitor a partial recovery response of the sample after application of the first pulse and before application of the second pulse.

17. The system of claim 12 wherein the at least one acoustic transducer comprises a single acoustic transducer use for applying the mechanical force and performing the monitoring.

18. The system of claim 12 wherein the at least one acoustic transducer comprises a first acoustic transducer for applying the mechanical force and a second acoustic transducer separate from the first acoustic transducer for performing the monitoring.

19. The system of claim 12 wherein the mechanical properties estimator is configured to determine the quantitative value for the mechanical property using a mechanical model for viscoelasticity.

20. The system of claim 19 wherein the mechanical model comprises the Voigt model, the standard linear model, or the Maxwell model.

21. The system of claim 12 wherein the mechanical property comprises at least one relaxation time constant.

22. The system of claim 21 wherein the mechanical properties estimator is configured to determine a steady state displacement of the sample from the at least one relaxation time constant and an observed displacement from at least one excitation.

23. The system of claim 1 wherein the mechanical property comprises a coefficient of viscosity or an elastic modulus.

24. A non-transitory computer readable medium having stored thereon executable instructions that when executed by the processor of a computer control the computer to perform steps comprising:
 applying a plurality of pulses of acoustic energy to a sample to apply a mechanical force to the sample and induce a non-steady-state displacement in the sample;
 monitoring a response of the sample caused by the application of the mechanical force; and
 determining a quantitative value for a mechanical property of the sample based on the response.

* * * * *